United States Patent
Hu et al.

(10) Patent No.: US 9,492,301 B2
(45) Date of Patent: *Nov. 15, 2016

(54) CIRCUMFERENTIAL WALKER

(71) Applicant: OSSUR HF, Reykjavik (IS)

(72) Inventors: Irving Hu, Irvine, CA (US); Jane Lee, Fullerton, CA (US)

(73) Assignee: OSSUR HF, Reykjavik (IS)

(*) Notice: Subject to any disclaimer, the term of this patent is extended or adjusted under 35 U.S.C. 154(b) by 0 days.

This patent is subject to a terminal disclaimer.

(21) Appl. No.: 13/951,933

(22) Filed: Jul. 26, 2013

(65) Prior Publication Data

US 2013/0310721 A1 Nov. 21, 2013

Related U.S. Application Data

(63) Continuation of application No. 12/563,386, filed on Sep. 21, 2009, now Pat. No. 8,506,510, which is acontinuation of application No. 12/466,577, filed on May 15, 2009, now Pat. No. 8,002,724.

(Continued)

(51) Int. Cl.
*A61F 5/01* (2006.01)

(52) U.S. Cl.
CPC .............. *A61F 5/012* (2013.01); *A61F 5/01* (2013.01); *A61F 5/0111* (2013.01); *A61F 5/0127* (2013.01); *A61F 5/0195* (2013.01)

(58) Field of Classification Search
CPC .... A61F 5/0111; A61F 13/04; A61F 5/0127; A61F 5/0193; A61F 5/019; A61F 5/0585; A43B 7/20

USPC ........ 128/882; 602/5, 16, 23, 25–27; 36/116, 36/117.1, 140, 154–155
See application file for complete search history.

(56) References Cited

U.S. PATENT DOCUMENTS

| 975,576 A | 11/1910 | Sexton |
|---|---|---|
| 1,012,017 A | 12/1911 | Salt |

(Continued)

FOREIGN PATENT DOCUMENTS

| DE | 2 341 658 A1 | 3/1974 |
|---|---|---|
| DE | 32 28 753 A1 | 2/1984 |

(Continued)

OTHER PUBLICATIONS

Nextep™ Contour Walker, product information sheet from Internet search results, www.djortho.com, Jan. 1, 2008, 1 page.

(Continued)

*Primary Examiner* — Ophelia A Hawthorne
(74) *Attorney, Agent, or Firm* — Workman Nydegger

(57) ABSTRACT

An orthopedic device in the form of a circumferential walker includes a first member (posterior shell) and a second member (dorsal shell) corresponding to the first member. An outsole or plantar shell portion is attached to, or formed on or with the posterior shell. A hinge mechanism is provided between the posterior and dorsal shells to allow the dorsal shell to be swung away from the posterior shell in order to accommodate an anatomical limb therein. Inflatable bladders having perspiration wicking channels and/or openings are provided within a liner for insertion between the posterior and dorsal shells. Quick-connecting buckle and retaining assemblies can be provided to allow a user to quickly don and doff the orthopedic device.

9 Claims, 29 Drawing Sheets

Related U.S. Application Data

(60) Provisional application No. 61/071,747, filed on May 15, 2008, provisional application No. 61/071,829, filed on May 20, 2008, provisional application No. 61/099,017, filed on Sep. 22, 2008.

(56) References Cited

U.S. PATENT DOCUMENTS

| | | |
|---|---|---|
| 2,200,849 A | 5/1940 | Margolin |
| 2,236,367 A | 3/1941 | Gruber |
| 2,292,297 A | 8/1942 | Sherlock |
| 2,444,640 A | 7/1948 | Epstein |
| 2,868,191 A | 1/1959 | Juhasz |
| 2,885,797 A | 5/1959 | Chrencik |
| 2,888,016 A | 5/1959 | De Lamater |
| 2,909,854 A | 10/1959 | Edelstein |
| 2,913,837 A | 11/1959 | Geuder |
| 2,917,844 A | 12/1959 | Scholl |
| 2,928,193 A | 3/1960 | Kristan |
| 2,979,835 A | 4/1961 | Scholl |
| 2,979,836 A | 4/1961 | Scholl |
| 3,270,358 A | 9/1966 | Milner |
| 3,464,126 A | 9/1969 | Sarkissian |
| 3,548,420 A | 12/1970 | Spence |
| 3,580,248 A | 5/1971 | Larson |
| 3,681,860 A | 8/1972 | Bidegain |
| 3,685,176 A | 8/1972 | Rudy |
| 3,730,169 A | 5/1973 | Fiber |
| 3,735,758 A | 5/1973 | Novotney |
| 3,760,056 A | 9/1973 | Rudy |
| 3,786,805 A | 1/1974 | Tourin |
| 3,792,537 A | 2/1974 | Plank et al. |
| 3,814,088 A | 6/1974 | Raymond |
| 3,834,377 A | 9/1974 | Lebold |
| 3,859,740 A | 1/1975 | Kemp |
| 3,922,800 A | 12/1975 | Miller et al. |
| 3,955,565 A | 5/1976 | Johnson, Jr. |
| 4,045,888 A | 9/1977 | Oxenberg |
| 4,057,056 A | 11/1977 | Payton |
| 4,095,353 A | 6/1978 | Foldes |
| 4,100,686 A | 7/1978 | Sgarlato et al. |
| 4,142,307 A | 3/1979 | Martin |
| 4,177,583 A | 12/1979 | Chapman |
| 4,184,273 A | 1/1980 | Boyer et al. |
| 4,217,706 A | 8/1980 | Vartanian |
| 4,217,893 A | 8/1980 | Payton |
| 4,232,459 A | 11/1980 | Vaccari |
| 4,237,626 A | 12/1980 | Brown |
| 4,267,649 A | 5/1981 | Smith |
| 4,300,294 A | 11/1981 | Riecken |
| 4,333,248 A | 6/1982 | Samuels |
| 4,370,818 A | 2/1983 | Simoglou |
| 4,408,402 A | 10/1983 | Looney |
| 4,414,965 A | 11/1983 | Mauldin et al. |
| D272,281 S | 1/1984 | Alush |
| 4,446,856 A | 5/1984 | Jordan |
| 4,494,536 A | 1/1985 | Latenser |
| 4,505,269 A | 3/1985 | Davies et al. |
| 4,550,721 A | 11/1985 | Michel |
| 4,565,017 A | 1/1986 | Ottieri |
| 4,571,853 A | 2/1986 | Medrano |
| 4,572,169 A | 2/1986 | Mauldin et al. |
| 4,587,962 A | 5/1986 | Greene et al. |
| 4,598,484 A | 7/1986 | Ma |
| 4,599,811 A | 7/1986 | Rousseau |
| 4,608,768 A | 9/1986 | Cavanagh |
| 4,620,378 A | 11/1986 | Sartor |
| 4,633,598 A | 1/1987 | Moronaga et al. |
| 4,633,599 A | 1/1987 | Morell et al. |
| 4,633,877 A | 1/1987 | Pendergast |
| 4,660,300 A | 4/1987 | Morell et al. |
| 4,669,202 A | 6/1987 | Ottieri |
| 4,674,204 A | 6/1987 | Sullivan et al. |
| 4,674,205 A | 6/1987 | Anger |
| 4,677,767 A | 7/1987 | Darby |
| 4,680,878 A | 7/1987 | Pozzobon et al. |
| 4,689,898 A | 9/1987 | Fahey |
| 4,719,710 A | 1/1988 | Pozzobon |
| 4,727,661 A | 3/1988 | Kuhn |
| 4,741,115 A | 5/1988 | Pozzobon |
| 4,748,726 A | 6/1988 | Schoch |
| 4,760,653 A | 8/1988 | Baggio |
| 4,771,768 A | 9/1988 | Crispin |
| 4,773,170 A | 9/1988 | Moore et al. |
| 4,793,078 A | 12/1988 | Andrews |
| D299,787 S | 2/1989 | Bates |
| 4,805,321 A | 2/1989 | Tonkel |
| 4,805,601 A | 2/1989 | Eischen, Sr. |
| 4,811,504 A | 3/1989 | Bunke |
| 4,869,001 A | 9/1989 | Brown |
| 4,872,273 A | 10/1989 | Smeed |
| 4,879,822 A | 11/1989 | Hayes |
| 4,893,418 A | 1/1990 | Ogden |
| 4,934,355 A | 6/1990 | Porcelli |
| 4,947,838 A | 8/1990 | Giannetti |
| 4,974,583 A | 12/1990 | Freitas |
| 5,065,481 A | 11/1991 | Walkhoff |
| 5,065,531 A | 11/1991 | Prestridge |
| 5,078,128 A | 1/1992 | Grim et al. |
| 5,123,180 A | 6/1992 | Nannig et al. |
| 5,125,400 A | 6/1992 | Johnson, Jr. |
| D329,527 S | 9/1992 | Cohen |
| 5,143,058 A | 9/1992 | Luber et al. |
| D330,109 S | 10/1992 | Hatfield |
| 5,152,038 A | 10/1992 | Schoch |
| 5,154,682 A | 10/1992 | Kellerman |
| 5,154,695 A | 10/1992 | Farris et al. |
| 5,157,813 A | 10/1992 | Carroll |
| 5,176,623 A | 1/1993 | Stetman et al. |
| 5,176,624 A | 1/1993 | Kuehnreich |
| 5,183,036 A | 2/1993 | Spademan |
| 5,197,942 A | 3/1993 | Brady |
| D334,646 S | 4/1993 | Dissinger |
| D337,876 S | 8/1993 | Kilbey |
| 5,233,767 A | 8/1993 | Kramer |
| 5,242,379 A | 9/1993 | Harris et al. |
| 5,249,377 A | 10/1993 | Walkhoff |
| 5,277,695 A | 1/1994 | Johnson, Jr. et al. |
| D344,589 S | 2/1994 | Kilbey |
| 5,288,286 A | 2/1994 | Davis et al. |
| 5,325,613 A | 7/1994 | Sussmann |
| 5,329,705 A | 7/1994 | Grim et al. |
| D352,191 S | 11/1994 | Zorian |
| D352,784 S | 11/1994 | Cohen et al. |
| 5,359,791 A | 11/1994 | Prahl et al. |
| 5,368,549 A | 11/1994 | McVicker |
| 5,368,551 A | 11/1994 | Zuckerman |
| 5,370,133 A | 12/1994 | Darby et al. |
| 5,378,223 A | 1/1995 | Grim et al. |
| 5,399,152 A | 3/1995 | Habermeyer et al. |
| 5,407,421 A | 4/1995 | Goldsmith |
| 5,425,701 A | 6/1995 | Oster et al. |
| 5,426,872 A | 6/1995 | Hayes |
| 5,429,588 A | 7/1995 | Young et al. |
| 5,433,695 A | 7/1995 | Drennan |
| 5,435,009 A | 7/1995 | Schild et al. |
| 5,438,768 A | 8/1995 | Bauerfeind |
| 5,441,015 A | 8/1995 | Farley |
| D363,780 S | 10/1995 | Darby et al. |
| 5,464,385 A | 11/1995 | Grim |
| 5,477,593 A | 12/1995 | Leick |
| D365,919 S | 1/1996 | Chen |
| 5,483,757 A | 1/1996 | Frykberg |
| 5,496,263 A | 3/1996 | Fuller, II et al. |
| 5,548,848 A | 8/1996 | Huybrechts |
| D373,548 S | 9/1996 | Losi, II |
| D375,191 S | 11/1996 | Tonkel et al. |
| 5,577,998 A | 11/1996 | Johnson, Jr. et al. |
| D376,429 S | 12/1996 | Antar |
| 5,617,650 A | 4/1997 | Grim |
| D379,258 S | 5/1997 | Cheng |
| 5,641,322 A | 6/1997 | Silver et al. |
| 5,647,104 A | 7/1997 | James |
| 5,656,226 A | 8/1997 | McVicker |

(56) References Cited

U.S. PATENT DOCUMENTS

| | | |
|---|---|---|
| D383,250 S | 9/1997 | Amico |
| D384,746 S | 10/1997 | Varn |
| D390,345 S | 2/1998 | Aird et al. |
| 5,717,996 A | 2/1998 | Feldmann |
| D391,748 S | 3/1998 | Koh |
| 5,761,834 A | 6/1998 | Grim et al. |
| 5,778,563 A | 7/1998 | Ahlbaumer |
| 5,778,565 A | 7/1998 | Holt et al. |
| 5,797,862 A | 8/1998 | Lamont |
| D398,142 S | 9/1998 | Benoit |
| D398,439 S | 9/1998 | McDonald |
| 5,819,378 A | 10/1998 | Doyle |
| 5,827,210 A | 10/1998 | Antar et al. |
| 5,827,211 A | 10/1998 | Sellinger |
| D401,042 S | 11/1998 | Davis |
| 5,833,639 A * | 11/1998 | Nunes .................. A61F 5/0111 128/882 |
| 5,836,902 A * | 11/1998 | Gray ................................. 602/5 |
| 5,846,063 A | 12/1998 | Lakic |
| 5,853,380 A | 12/1998 | Miller |
| 5,857,987 A | 1/1999 | Habermeyer |
| D404,895 S | 2/1999 | Rosato |
| 5,868,690 A | 2/1999 | Eischen, Sr. |
| 5,913,841 A | 6/1999 | Lamont |
| 5,934,599 A | 8/1999 | Hammerslag |
| 5,961,477 A | 10/1999 | Turtzo |
| 5,993,404 A | 11/1999 | McNiel |
| 6,000,148 A | 12/1999 | Cretinon |
| D418,967 S | 1/2000 | Stengel |
| 6,021,780 A | 2/2000 | Darby |
| 6,027,468 A | 2/2000 | Pick |
| 6,044,578 A | 4/2000 | Kelz |
| 6,098,315 A | 8/2000 | Hoffmann, III |
| 6,202,953 B1 | 3/2001 | Hammerslag |
| 6,205,685 B1 | 3/2001 | Kellerman |
| 6,228,044 B1 | 5/2001 | Jensen et al. |
| 6,267,742 B1 | 7/2001 | Krivosha et al. |
| RE37,338 E | 8/2001 | McVicker |
| 6,289,558 B1 | 9/2001 | Hammerslag |
| 6,334,854 B1 | 1/2002 | Davis |
| 6,338,768 B1 | 1/2002 | Chi |
| 6,361,514 B1 * | 3/2002 | Brown .................. A61F 5/0111 128/882 |
| 6,377,178 B1 | 4/2002 | DeToro et al. |
| 6,409,691 B1 | 6/2002 | Dakin et al. |
| 6,432,073 B2 | 8/2002 | Pior et al. |
| D467,708 S | 12/2002 | Portzline |
| D473,654 S | 4/2003 | Iglesias et al. |
| D473,704 S | 4/2003 | Wilson |
| 6,572,571 B2 | 6/2003 | Lowe |
| D476,799 S | 7/2003 | Fuerst |
| 6,589,194 B1 | 7/2003 | Calderon et al. |
| 6,682,497 B2 | 1/2004 | Jensen et al. |
| 6,755,798 B2 | 6/2004 | McCarthy et al. |
| 6,792,699 B2 | 9/2004 | Long et al. |
| D500,855 S | 1/2005 | Pick et al. |
| 6,866,043 B1 | 3/2005 | Davis |
| D505,727 S | 5/2005 | Krahner et al. |
| 6,945,944 B2 | 9/2005 | Kuiper et al. |
| 6,976,972 B2 | 12/2005 | Bradshaw |
| 6,991,613 B2 | 1/2006 | Sensabaugh |
| 7,010,823 B2 | 3/2006 | Baek |
| 7,018,351 B1 | 3/2006 | Iglesias et al. |
| D528,214 S | 9/2006 | Binet |
| 7,198,610 B2 | 4/2007 | Ingimundarson et al. |
| 7,281,341 B2 | 10/2007 | Reagan et al. |
| 7,288,076 B2 | 10/2007 | Grim et al. |
| D554,835 S | 11/2007 | Peydro |
| D555,343 S | 11/2007 | Bettencourt |
| 7,303,538 B2 | 12/2007 | Grim et al. |
| 7,311,686 B1 | 12/2007 | Iglesias et al. |
| 7,354,411 B2 | 4/2008 | Perry et al. |
| RE40,363 E | 6/2008 | Grim et al. |
| 7,384,584 B2 | 6/2008 | Jerome et al. |
| D575,039 S | 8/2008 | Amado et al. |
| 7,418,755 B2 | 9/2008 | Bledsoe et al. |
| D583,956 S | 12/2008 | Chang et al. |
| 7,493,706 B2 | 2/2009 | Cho et al. |
| 7,524,295 B1 * | 4/2009 | Peters .................. A61F 5/0127 602/23 |
| D592,755 S | 5/2009 | Chang et al. |
| D592,756 S | 5/2009 | Chang et al. |
| D596,301 S | 7/2009 | Campos et al. |
| D596,386 S | 7/2009 | Brambilla |
| 7,591,050 B2 | 9/2009 | Hammerslag |
| D603,155 S | 11/2009 | Della Valle et al. |
| D614,775 S | 4/2010 | Snively |
| D615,285 S | 5/2010 | Martin |
| D616,556 S | 5/2010 | Hu |
| 7,717,869 B2 | 5/2010 | Eischen, Sr. |
| 7,727,174 B2 | 6/2010 | Chang et al. |
| D622,494 S | 8/2010 | Warren |
| 7,838,717 B2 | 11/2010 | Haggstrom et al. |
| D634,438 S | 3/2011 | Hu |
| D634,852 S | 3/2011 | Hu |
| D636,157 S | 4/2011 | Nascimento |
| D636,159 S | 4/2011 | Petrie |
| 7,964,766 B2 | 6/2011 | Blott et al. |
| D642,363 S | 8/2011 | Rajmohan et al. |
| D642,775 S | 8/2011 | Raysse |
| 8,002,724 B2 | 8/2011 | Hu et al. |
| 8,012,112 B2 | 9/2011 | Barberio |
| 8,021,347 B2 | 9/2011 | Vitaris et al. |
| D648,113 S | 11/2011 | Chang |
| D651,381 S | 1/2012 | Simms |
| 8,158,844 B2 | 4/2012 | McNeil |
| D661,887 S | 6/2012 | Petrie |
| 8,308,705 B2 | 11/2012 | Lin et al. |
| 8,313,449 B2 | 11/2012 | Hardman et al. |
| D675,421 S | 2/2013 | Petrie |
| D677,866 S | 3/2013 | Vestuti et al. |
| D680,728 S | 4/2013 | Stryjak |
| D682,517 S | 5/2013 | Taylor |
| D683,214 S | 5/2013 | McAdam |
| 8,506,510 B2 | 8/2013 | Hu et al. |
| 8,574,181 B2 | 11/2013 | Bird et al. |
| D696,499 S | 12/2013 | Lehtinen |
| D696,785 S | 12/2013 | Weaver, II et al. |
| D698,074 S | 1/2014 | Hargreaves |
| D698,338 S | 1/2014 | Ingham et al. |
| D701,032 S | 3/2014 | Leleu |
| D701,033 S | 3/2014 | Leleu |
| D703,335 S | 4/2014 | Bird et al. |
| D712,639 S | 9/2014 | Spring |
| D714,042 S | 9/2014 | Petrie |
| 9,333,106 B2 * | 5/2016 | Hu ........................ A61F 5/0111 |
| 2002/0095105 A1 | 7/2002 | Jensen |
| 2002/0095750 A1 | 7/2002 | Hammerslag |
| 2002/0128574 A1 * | 9/2002 | Darby .................. A61F 5/0111 602/23 |
| 2003/0093882 A1 | 5/2003 | Gorza et al. |
| 2003/0171703 A1 | 9/2003 | Grim et al. |
| 2003/0204938 A1 | 11/2003 | Hammerslag |
| 2004/0010212 A1 | 1/2004 | Kuiper et al. |
| 2004/0019307 A1 | 1/2004 | Grim et al. |
| 2004/0167453 A1 | 8/2004 | Peters |
| 2005/0131324 A1 | 6/2005 | Bledsoe |
| 2005/0145256 A1 | 7/2005 | Howard et al. |
| 2005/0165338 A1 | 7/2005 | Iglesias et al. |
| 2005/0171461 A1 * | 8/2005 | Pick ............................... 602/27 |
| 2005/0172517 A1 | 8/2005 | Bledsoe et al. |
| 2005/0274046 A1 | 12/2005 | Schwartz |
| 2006/0084899 A1 | 4/2006 | Verkade et al. |
| 2006/0135899 A1 | 6/2006 | Jerome et al. |
| 2006/0135902 A1 | 6/2006 | Ingimundarson et al. |
| 2006/0156517 A1 | 7/2006 | Hammerslag et al. |
| 2006/0189907 A1 | 8/2006 | Pick et al. |
| 2006/0217649 A1 | 9/2006 | Rabe |
| 2006/0229541 A1 | 10/2006 | Hassler et al. |
| 2007/0167884 A1 | 7/2007 | Mangrum et al. |
| 2007/0169378 A1 | 7/2007 | Sodeberg et al. |
| 2007/0185425 A1 | 8/2007 | Einarsson et al. |
| 2007/0191749 A1 | 8/2007 | Barberio |
| 2007/0282230 A1 | 12/2007 | Valderrabano et al. |

(56) References Cited

U.S. PATENT DOCUMENTS

| | | |
|---|---|---|
| 2007/0293798 A1 | 12/2007 | Hu et al. |
| 2008/0060167 A1 | 3/2008 | Hammerslag et al. |
| 2008/0060168 A1 | 3/2008 | Hammerslag et al. |
| 2008/0066272 A1 | 3/2008 | Hammerslag et al. |
| 2008/0066345 A1 | 3/2008 | Hammerslag et al. |
| 2008/0066346 A1 | 3/2008 | Hammerslag et al. |
| 2008/0083135 A1 | 4/2008 | Hammerslag et al. |
| 2008/0294082 A1 | 11/2008 | Chang et al. |
| 2008/0294083 A1 | 11/2008 | Chang et al. |
| 2009/0012482 A1 | 1/2009 | Pinto et al. |
| 2009/0099495 A1* | 4/2009 | Campos ............... A61F 5/0127 602/27 |
| 2009/0270820 A1 | 10/2009 | Johnson et al. |
| 2009/0287127 A1 | 11/2009 | Hu et al. |
| 2009/0287128 A1 | 11/2009 | Ingimundarson et al. |
| 2010/0069808 A1 | 3/2010 | Mitchell |
| 2010/0100020 A1 | 4/2010 | Fout et al. |
| 2010/0234782 A1 | 9/2010 | Hu et al. |
| 2010/0324461 A1 | 12/2010 | Darby, II et al. |
| 2011/0009791 A1 | 1/2011 | Hopmann |
| 2011/0015555 A1 | 1/2011 | Anderson et al. |
| 2012/0035560 A1 | 2/2012 | Eddy et al. |
| 2012/0078148 A1 | 3/2012 | Hu et al. |
| 2012/0220960 A1 | 8/2012 | Ruland |
| 2012/0238924 A1 | 9/2012 | Avni |
| 2013/0066247 A1 | 3/2013 | Bird et al. |
| 2013/0310721 A1 | 11/2013 | HU et al. |
| 2014/0171837 A1 | 6/2014 | Harcourt |
| 2014/0276310 A1 | 9/2014 | Grim et al. |

FOREIGN PATENT DOCUMENTS

| | | |
|---|---|---|
| EP | 0 095 396 | 11/1983 |
| EP | 0 201 051 | 11/1986 |
| EP | 0770368 A1 | 5/1997 |
| EP | 2468323 A1 | 6/2012 |
| FR | 2 399 811 A1 | 3/1979 |
| FR | 2634988 A1 | 2/1990 |
| FR | 2 681 516 A1 | 3/1993 |
| GB | 2 124 473 A | 2/1984 |
| GB | 2 178 940 A | 2/1987 |
| JP | 2005211626 A | 8/2005 |
| WO | 93/13685 A1 | 7/1993 |
| WO | 9324081 | 12/1993 |
| WO | 94/18863 A1 | 9/1994 |
| WO | 97/36507 A1 | 10/1997 |
| WO | 2004/021817 A1 | 3/2004 |
| WO | 2006035469 A2 | 4/2006 |
| WO | 2006045079 A1 | 4/2006 |
| WO | 2007078845 A2 | 7/2007 |
| WO | 2010104824 A1 | 9/2010 |
| WO | 2013/084213 A1 | 6/2013 |
| WO | 2015006766 A1 | 1/2015 |

OTHER PUBLICATIONS

Nextep Contour w/Air Walker, product information sheet from Internet search results, www.djortho.com, Jan. 1, 2008, 1 page.
XP Achilles Walker (EU ony), product information sheet from Internet search results, www.aircast.com, Jan. 1, 2008, 4 pages.
XP Achilles Walker™, product information sheet from Internet search results, www.aircast.com, Jan. 1, 2008, 4 pages.
SP Walker™ (short pneumatic), product information sheet from Internet search results, www.aircast.com, Jan. 1, 2008, 4 pages.
FP Walker™ (foam pneumatic), product information sheet from Internet search results, www.aircast.com, Jan. 1, 2008, 4 pages.
XP Walker™ (extra pneumatic), product information sheet from Internet search results, www.aircast.com, Jan. 1, 2008, 4 pages.
International Search Report for INternational Application No. PCT/US2009/003018, mailed Jul. 24, 2009.
Office Action from corresponding U.S. Appl. No. 12/563,386, Sep. 1, 2011.
Final Office Action from corresponding U.S. Appl. No. 12/563,386, Mar. 13, 2012.
Office Action from corresponding U.S. Appl. No. 12/563,386, Jul. 12, 2012.
Final Office Action from corresponding U.S. Appl. No. 12/563,386, Dec. 15, 2012.
Notice of Allowance from corresponding U.S. Appl. No. 12/563,386, Apr. 15, 2013.
International Search Report and Written Opinion for international Application No. PCT/US2014/056201, Dec. 5, 2014.
International Search Report and Written Opinion from International Application No. PCT/US2014/057421, Dec. 8, 2014.
International Search Report and Written Opinion from International Application No. PCT/US2014/069686, Mar. 13, 2015.
International Search Report from PCT Application No. PCT/US2016/014816, Apr. 28, 2016.
European Search Report from corresponding European Application No. EP 15 20 0198.8, May 20, 2016.

* cited by examiner

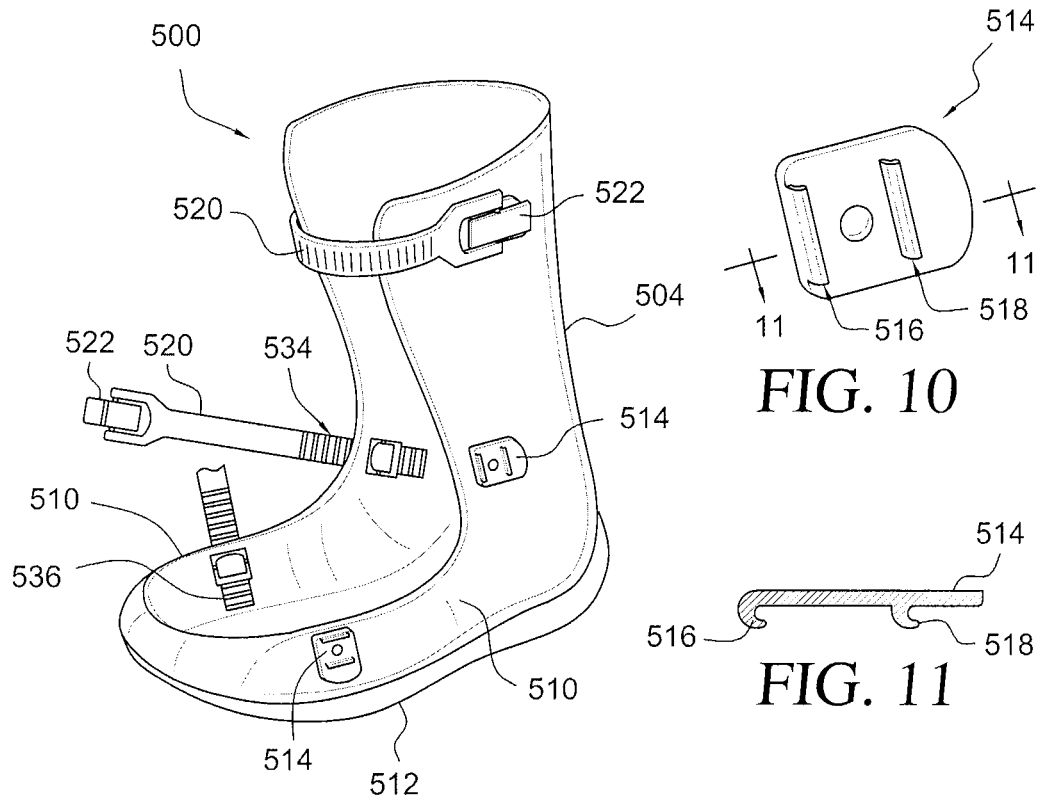
FIG. 9
FIG. 10
FIG. 11
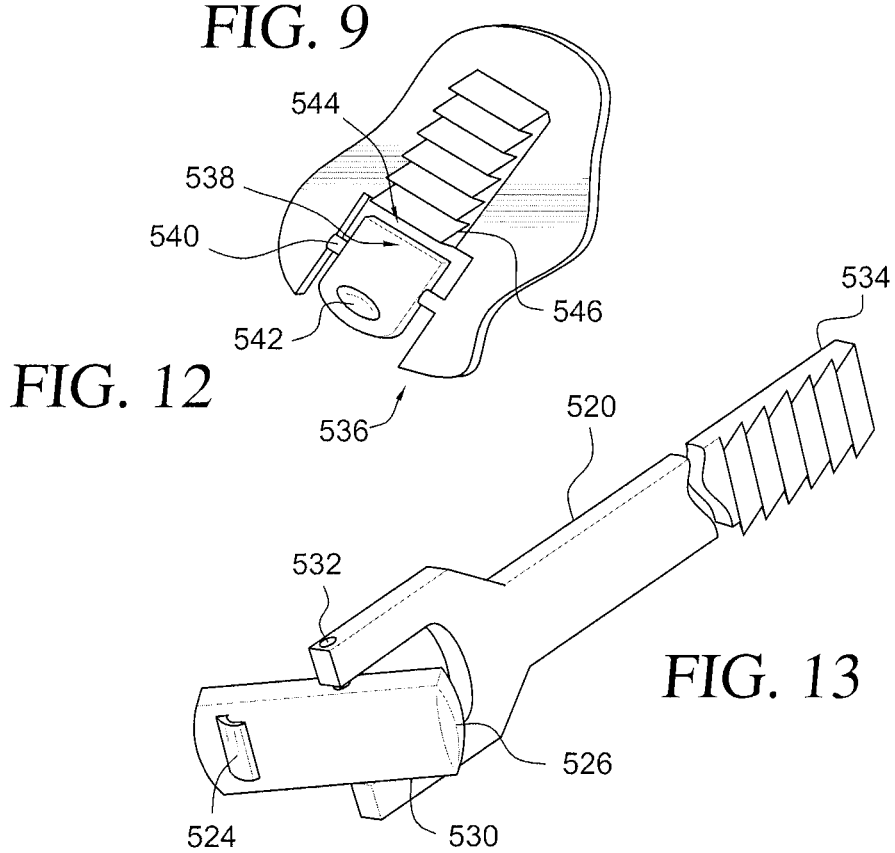
FIG. 12
FIG. 13

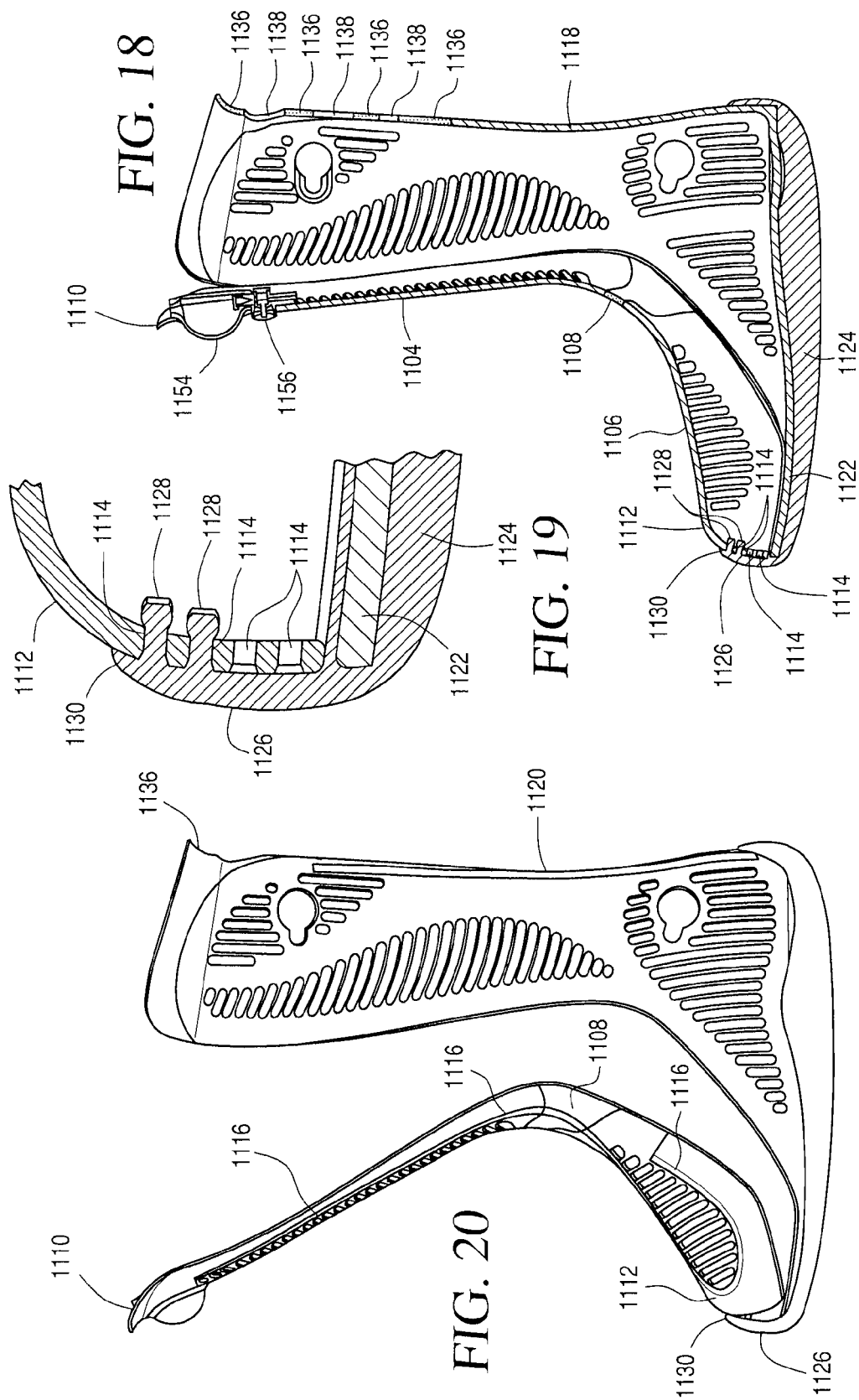

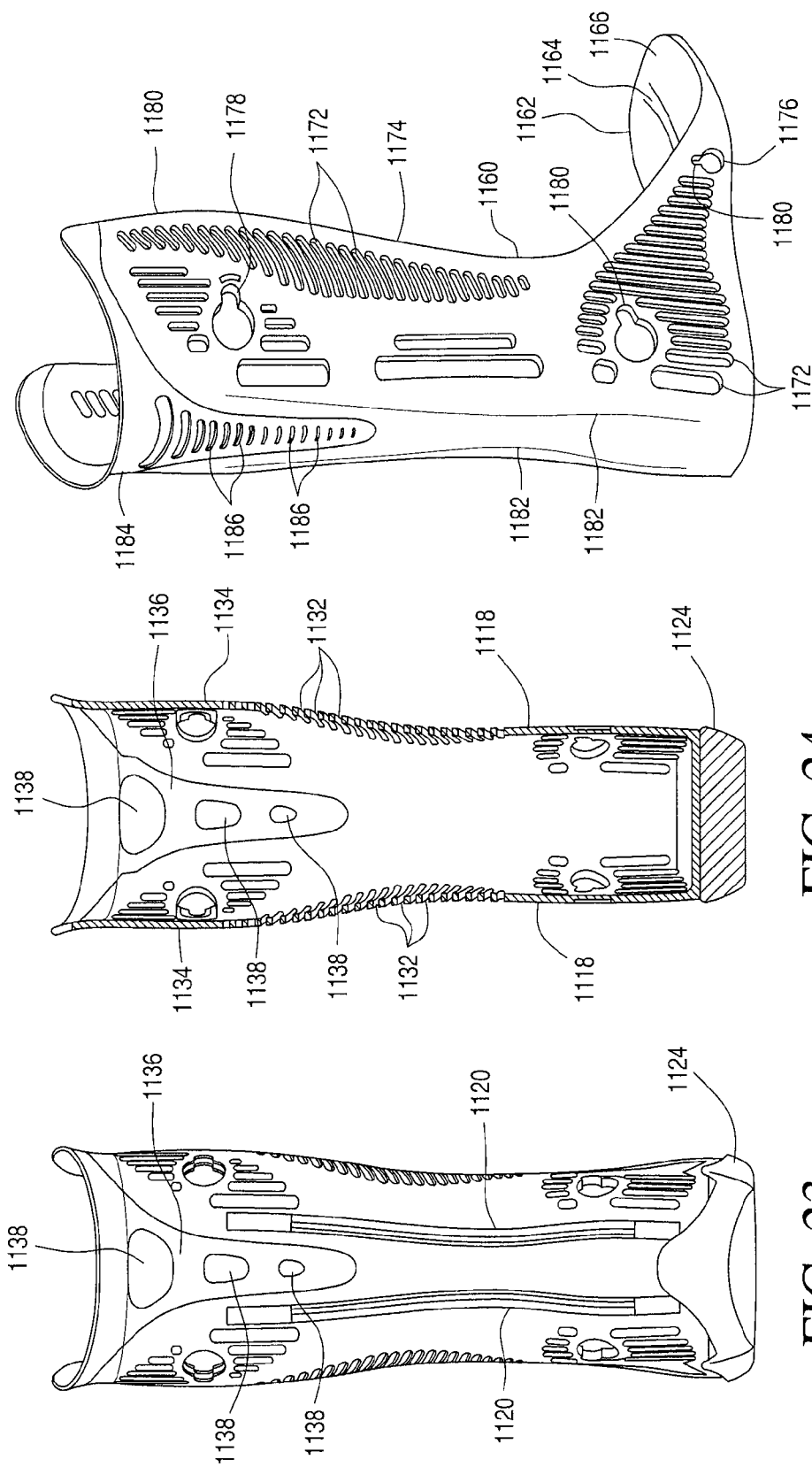

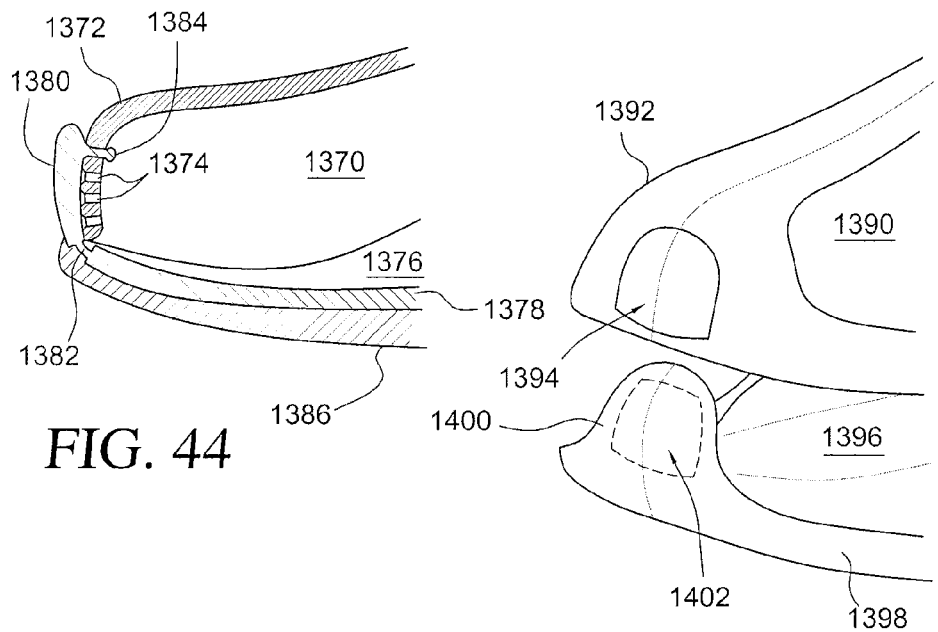
FIG. 44
FIG. 45
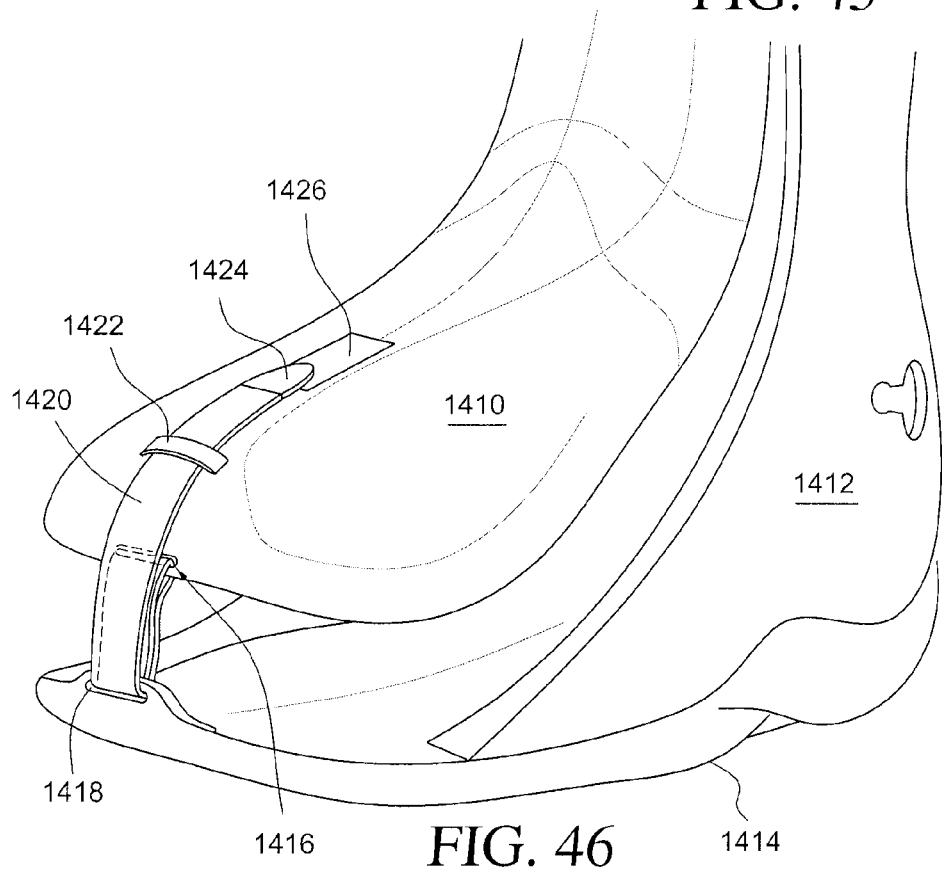
FIG. 46

CIRCUMFERENTIAL WALKER

FIELD OF THE INVENTION

The present invention relates generally to the field of orthopedic or prosthetic devices and more specifically to a circumferential orthopedic device that provides ease of donning, doffing, and adjusting with the benefits of circumferential or wrap-around support and stabilization of the supported limb. In particular, exemplary circumferential lower leg walkers are disclosed that provide support and stabilization to the lower leg, ankle, and foot with improved donning, removal, and tightening of the circumferential walkers around the lower leg.

BACKGROUND

It is common that people, especially physically active and frail elderly people, experience a variety of lower leg, ankle and foot injuries. For example, sprains to the calcaneofibular and anterior tabofibular ligaments often afflict a number of professional and amateur athletes. Other injuries can include moderate to severe ankle sprains, stable foot and ankle fractures or other trauma, such as surgery.

To aid in the proper healing and treatment of these and other lower leg and foot injuries, or for post-operative and/or rehabilitation purposes, it is necessary that the affected areas, as well as the surrounding tissue, be stabilized and immobilized.

Physicians traditionally have treated, and still currently treat, injuries affecting lower leg extremities and the foot by fitting the injured patient with the well-known, molded plaster or resin cast, which is set around an inner cotton or gauze lining. The placement of this type of cast around the lower leg is time consuming, heavy, and costly. Further, this type of cast must not come into contact with water, which makes patient bathing difficult and time consuming. Additionally, if the cast needs to be removed for any reason, for example inspection or physical therapy, a whole new cast must be prepared and applied.

Alternatively, lower leg walkers provide stabilization and support of the lower leg, including the ankle and foot, such that at least partial mobility may be maintained while an injury to the lower leg, ankle, and/or foot is in the process of healing. Further, in contrast to the molded plaster or resin cast, a lower leg walker can be removed by the patient in order to bathe or for inspection of the injured limb by a physician or practitioner.

Existing wrap-around or circumferential walkers can be bulky and difficult and time consuming to don and doff. In particular, numerous straps must be properly threaded through retaining rings and each strap individually tightened in order to properly support and immobilize the limb.

Further, existing circumferential walkers do not provide a mechanism for accommodating different sized lower legs, ankles, and feet of different users. Thus, many different sized walkers are needed to accommodate different sized users.

Alternatively, existing walkers may be of the one size fits all type, such that the walkers are designed for an average sized lower leg, ankle, and foot, but do not provide a comfortable fit for users that have larger or smaller than average lower legs, ankles, and feet. Particularly, hard edges and surfaces of existing walkers can cause pressure points that can cause users pain and discomfort, and may also cause injury to a user.

Accordingly, exemplary embodiments of a circumferential lower leg walker that alleviate or eliminate the above mentioned drawbacks are described herein.

SUMMARY

The orthopedic device described herein may be, in exemplary embodiments, a lightweight, offloading, lower leg walker. It is also contemplated that other orthopedic devices may utilize similar configurations as described below.

The exemplary embodiments of a lower leg walker described herein typically take the form of a circumferential type walker, which provides support and stabilization to the lower leg by surrounding the lower leg, ankle, and foot with an appropriate supporting superstructure. It will be recognized that the features described herein may have applicability to other lower leg walker configurations or other types of orthopedic devices.

In exemplary embodiments, various configurations of quick connect tightening mechanisms are utilized to provide quick and easy adjustment of the walkers in order to provide the desired amount of support and stabilization to the lower leg.

Further exemplary embodiments of a lower leg walker described herein may take the form of a hinged circumferential type walker, which provides support and stabilization to the lower leg by surrounding the lower leg, ankle, and foot with an appropriate supporting superstructure. It will be recognized that the features described herein may have applicability to other lower leg walker configurations or other types of prosthetic or orthopedic devices.

In the exemplary embodiments, various configurations of an adjustable hinge arrangement, expansion arrangements, and a quick connecting arrangement are utilized to provide quick and easy adjustment of the walker in order to provide the desired amount of support and stabilization to the lower leg and to accommodate numerous different users or wearers having different sized lower legs, ankles, and feet.

For example, an orthopedic device may include a first member (posterior shell) and a second member (dorsal shell) corresponding to the first member. An outsole portion may be attached or integrated with a plantar shell portion of the posterior shell. The outsole may include one or more hinge projections configured to engage one or more of a predetermined number of correspondingly shaped receiving openings in a toe cover portion of the dorsal shell in order to provide an adjustable hinge mechanism for the orthopedic device.

The posterior shell may include wing portions extending along the medial and lateral sides thereof. A flexible or resilient expansion joint may be positioned in the posterior of the posterior shell between the wing portions or between the wing portions and the posterior of the shell to provide a mechanism to allow the wing portions to expand to accommodate larger sized calves and lower legs. The expansion joint may also include flexible or resilient edge portions that extend along the proximal terminal edges of the posterior shell wing portions to reduce the likelihood of a pressure point or to further accommodate users having larger sized lower legs.

The dorsal shell may also include a flexible or resilient edge portion along the proximal terminal edge thereof to reduce the likelihood of a pressure point or to further accommodate users having larger sized lower legs. Alternatively, a living hinge may be formed along the edge portion of the dorsal shell to allow the edge of the dorsal shell to flex to accommodate users having larger sized lower legs and to reduce or eliminate pressure points.

The dorsal shell may also include a flexible or resilient portion or a hinge positioned between a proximal and distal portion of the dorsal shell in order to accommodate users having larger ankles and feet and to reduce or eliminate the formation of a pressure point along the dorsal shell.

Quick-connecting buckle assemblies may be provided to allow a user to quickly don and doff the orthopedic device. The quick-connecting buckle assemblies may be utilized with traditional hook and loop fastener straps. The user need only adjust the straps at the time of first use (or infrequently to accommodate swelling or reduction of swelling of tissues), and henceforth, each donning and doffing of the orthopedic device can be achieved via the use of the quick-connecting buckle assemblies, thus eliminating time consuming adjustment of numerous straps.

The numerous other advantages, features and functions of embodiments of a circumferential walker having the features discussed herein will become readily apparent and better understood in view of the following description and accompanying drawings. The following description is not intended to limit the scope of the orthopedic device, but instead merely provides exemplary embodiments for ease of understanding.

BRIEF DESCRIPTION OF THE DRAWINGS

These and other features, aspects, and advantages of the present invention will become better understood with regard to the following description, appended claims, and accompanying drawings where:

FIG. 9 is a side perspective view of another variation of the embodiment of FIG. 1 utilizing an alternate quick connecting strap configuration;

FIG. 10 is a side perspective view of a locking element of FIG. 9;

FIG. 11 is a cross-sectional view along plane 11-11 of the locking element of FIG. 8;

FIG. 12 is a close-up isolated perspective view of a connecting assembly of FIG. 9;

FIG. 13 is a perspective view of a strap of FIG. 9;

FIG. 18 is a side cross-sectional view of the posterior shell shown in FIGS. 14 and 15 with the straps removed;

FIG. 19 is a partial side cross-sectional view of an embodiment of the hinge between the dorsal shell and posterior shell of the walker of FIGS. 14 and 15;

FIG. 20 is a side view showing the hinge action between the dorsal shell and posterior shell of the walker of FIGS. 14 and 15 with the straps removed;

FIG. 23 is a rear view of the walker of FIGS. 14 and 15 with the straps removed;

FIG. 24 is a rear cross-sectional view of the walker of FIGS. 14 and 15 with the straps removed;

FIG. 25 is a perspective view of a variation of the posterior shell of FIG. 14;

FIG. 44 is a partial cross-sectional view of another variation of a hinge for use with a hinged circumferential walker in accordance with the present disclosure;

FIG. 45 is a partial perspective view of another variation of a hinge for use with a hinged circumferential walker in accordance with the present disclosure;

FIG. 46 is a partial perspective view of another variation of a hinge for use with a hinged circumferential walker in accordance with the present disclosure;

Figure 1:
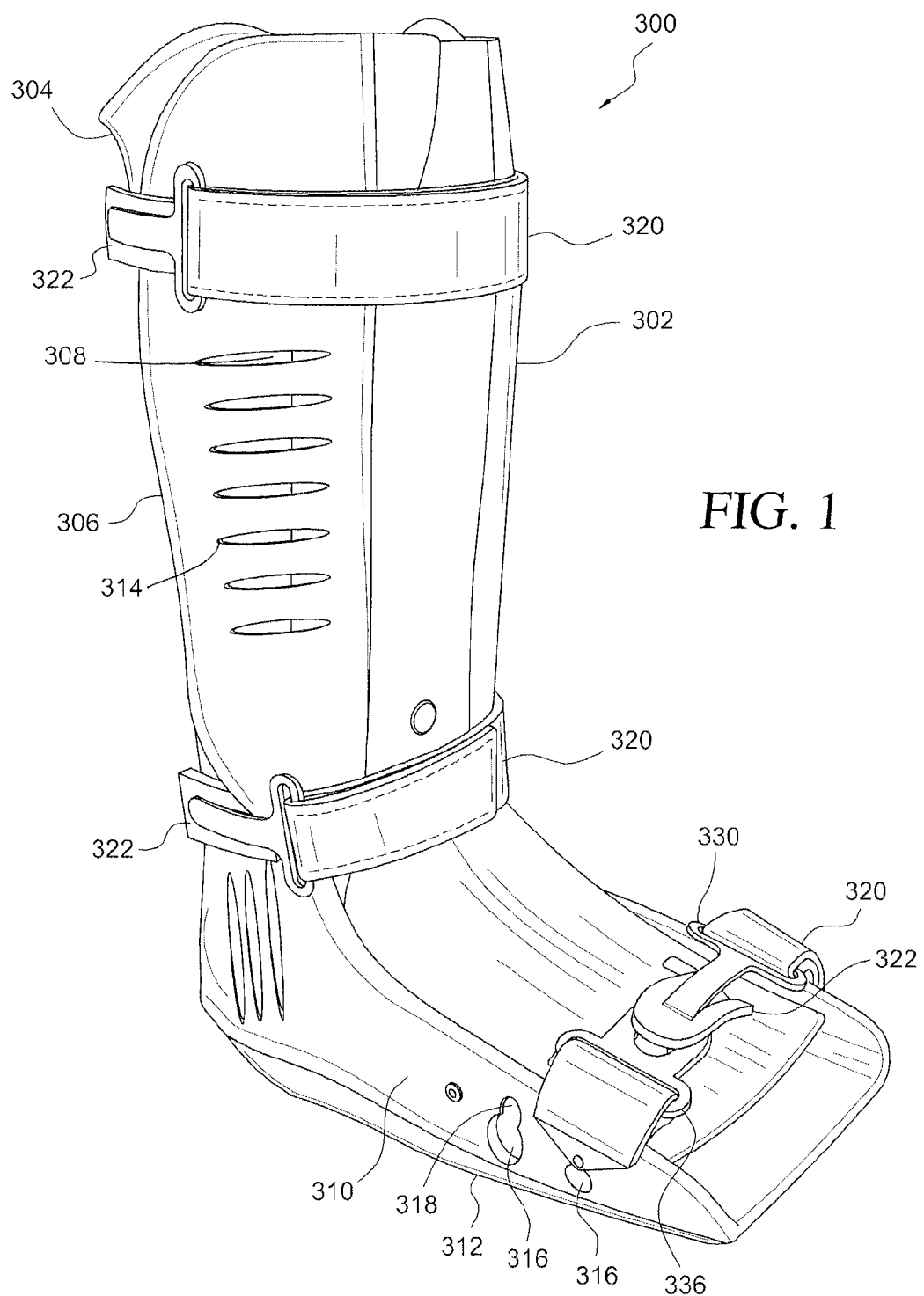
FIG. 1 is a front side perspective view of an embodiment of a circumferential walker according to the present disclosure.

It should be noted that the drawing figures are not necessarily drawn to scale, but instead are drawn to provide a better understanding of the components thereof, and are not intended to be limiting in scope, but rather to provide exemplary illustrations. It should further be noted that the figures illustrate exemplary embodiments of a circumferential walker and the components thereof, and in no way limit the structures or configurations of a circumferential walker and components thereof according to the present disclosure.

DETAILED DESCRIPTION

A. Environment and Context

Exemplary embodiments of an orthopedic device are provided for use in stabilizing and supporting the lower leg, foot, and ankle. Features that are provided on one side of the device can easily be provided on the other side of the device. In this manner, it is intended that the exemplary embodiments of the orthopedic device described herein may be used on either right or left lower legs, with any appropriate reconfiguration of components that is deemed necessary for the proper fit and function of the device for the purpose of supporting and stabilizing either the left or right lower leg.

In the exemplary embodiments of the orthopedic device described herein, quick release strap mechanisms may be used to provide ease of tightening the device. Exemplary quick release strap mechanisms are described in U.S. Pat. No. 7,198,610, granted April 2007, commonly owned, and herein incorporated in the entirety by reference.

The exemplary embodiments of the disclosure are adapted for supporting and stabilizing the lower leg of human beings, and may be dimensioned to accommodate different types, shapes and sizes of human joints and appendages.

Exemplary materials and configurations for components of the orthopedic device, such as sole portions and shell portions, are described in detail in U.S. Pat. No. 5,078,128, granted January 1992, U.S. Pat. No. 5,329,705, granted July 1994, U.S. Pat. No. 5,378,223, granted Jan. 3, 1995, U.S. Pat. No. 5,464,385, granted November 1995, and U.S. Pat. No. 5,761,834, granted June 1998, all assigned to Royce Medical Co. and all incorporated herein in the entirety by reference. Additional exemplary configurations and materials are described in detail in U.S. Pat. No. 7,303,538, granted December 2007, assigned to Össur hf, and incorporated herein in the entirety by reference.

For further ease of understanding the exemplary embodiments of an orthopedic device as disclosed herein, a description of a few terms is necessary. As used herein, the term "dorsal" has its ordinary meaning and refers to the top surfaces of the foot, ankle and foreleg or shin. As used herein, the term "plantar" has its ordinary meaning and refers to a bottom surface, such as the bottom of a foot. As used herein, the term "proximal" has its ordinary meaning and refers to a location that is closer to the heart than another location. Likewise, the term "distal" has its ordinary meaning and refers to a location that is further from the heart than another location. The term "posterior" also has its ordinary meaning and refers to a location that is behind or to the rear of another location. Lastly, the term "anterior" has its ordinary meaning and refers to a location that is ahead of or to the front of another location.

The terms "rigid," "flexible," and "resilient" may be used herein to distinguish characteristics of portions of certain features of the orthopedic device. The term "rigid" is intended to denote that an element of the device is generally devoid of flexibility. Within the context of support members or shells that are "rigid," it is intended to indicate that they do not lose their overall shape when force is applied, and in fact they may break if bent with sufficient force. On the other hand, the term "flexible" is intended to denote that features are capable of repeated bending such that the features may be bent into retained shapes or the features do not retain a general shape, but continuously deform when force is applied. The term "resilient" is used to qualify such flexible features as generally returning to an initial general shape without permanent deformation. As for the term "semi-rigid," this term is used to connote properties of support members or shells that provide support and are free-standing, however such support members or shells may have some degree of flexibility or resiliency.

B. Detailed Description of Various Embodiments of a Circumferential Walker

Figure 2:
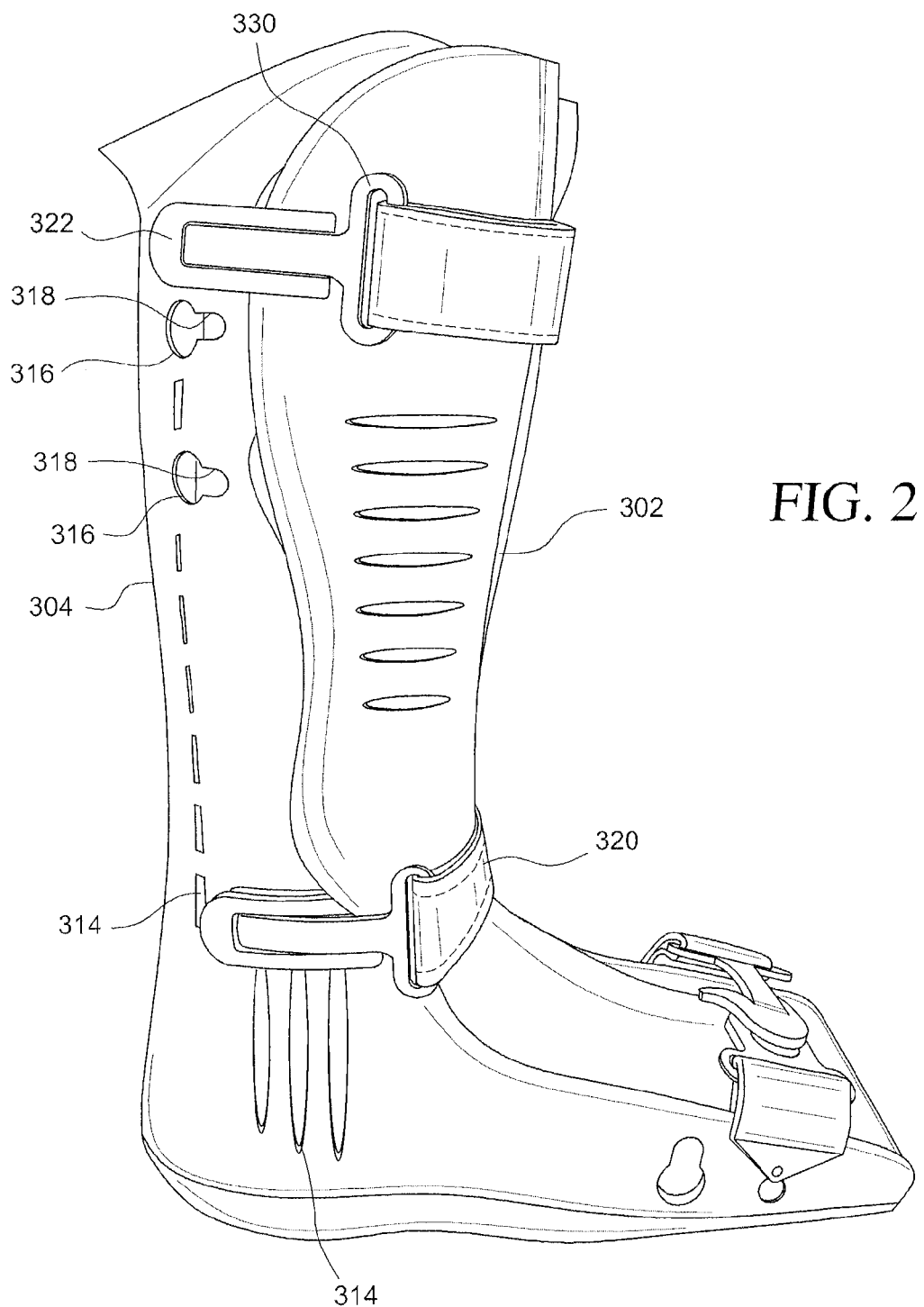
FIG. 2 is a side view of the embodiment of FIG. 1.
Figure 3:
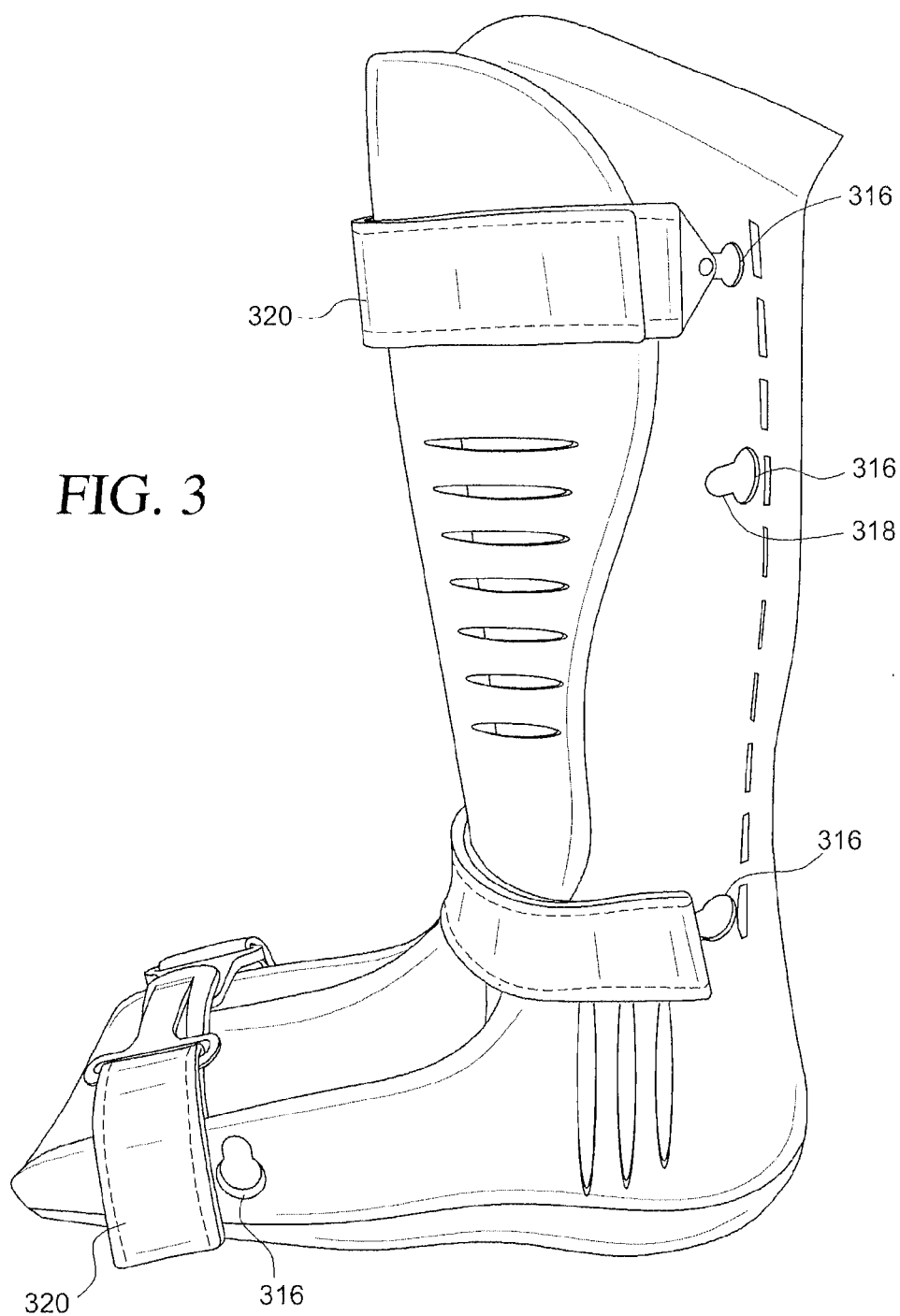
FIG. 3 is an alternate side view of the embodiment of FIG. 1.

An exemplary embodiment of a circumferential lower leg walker 300 is shown in FIGS. 1-3. As can be seen from the figures, this embodiment includes complementary dorsal 302 and posterior 304 shells that are selectively engageable with each other in order to provide easy access to the interior of the device for ease of donning and doffing the device, in particular for donning and doffing the device onto an injured limb.

The walker 300 is configured in an essentially two-piece or one-piece construction to provide a sleek and low profile device for use in stabilizing and supporting the lower leg and includes quick connect tightening mechanisms that provide tightening of the walker about the lower leg. Numerous advantages are obtained from such a configuration, such as lower weight, and less opportunity for the device to catch on external objects or clothing. Any weight savings will be a substantial benefit, as a user must swing the mass of the walker, along with the leg, through the gait cycle. Additionally, the ease with which the tightening mechanisms tighten the walker will aid users who may have trouble manipulating numerous and more complicated strap arrangements which require individual straps to be threaded through D-rings or other similar retention members. In particular, elderly or infirm persons will be able to properly tighten the walker with ease.

The walker 300 includes a semi-rigid, or substantially rigid shell configuration that is formed to support and surround the lower leg, foot, and ankle of a user. The shell configuration can extend from the foot and ankle up along the shin and tibia of the lower leg to a desired point below the knee joint. Exemplary suitable materials for forming the shells can include metals, such as aluminum, carbon, composite materials, such as carbon fiber/epoxy composites, glass fiber/epoxy composites, or suitable plastic materials, such as thermoplastic or thermosetting polymers, fiber reinforced plastic, molded chopped fibers, or any other suitable material. Other exemplary materials include, but are not limited to, nylons, glass filled nylon, polypropylenes, vinyls, polyvinyl chlorides, high density polyethylene, epoxies, urethanes, and polyesters.

The shell configuration includes a unitary dorsal shell 302, a posterior shell 304, and side shell portions 310 extending along the lateral and medial sides of an outsole 312. The side shell portions 310 may extend around the anterior of the walker 300 to define a toe protector portion. The outsole 312 can be formed with suitable tread or other friction enhancing characteristics, and to provide the appropriate rocker sole type response associated with lower leg walkers. Any suitable material may be utilized to form the outsole 312.

In order to further reduce the weight of the walker 300, and/or to provide ventilation, material can be removed from areas of the shell portions to provide clearance holes 314. The clearance holes 314 can be formed in any of the shell portions and have any suitable size and/or shape.

In a variation, some or all of the clearance holes can be filled with a liner or spacer fabric to provide aerated cushioning for the foot within the walker. Exemplary spacer materials are described in detail in U.S. publication nos. 2006/0135902, published June 2006, and 2007/0185425, published August 2007, both incorporated herein in the entirety by reference. Such a spacer fabric can provide additional comfort and a proper fit of the walker 1.

In the exemplary configuration of the walker 300 shown in FIGS. 1-3, each of the dorsal and posterior shells 302, 304 includes wing portions 306, 308 that extend from the respective shell portions towards the opposed shell portion. The wing portions 306, 308 wrap around the leg in order to enclose and support the leg. The dorsal shell wing portions 306 extend generally towards the posterior of the walker 300 and the posterior shell wing portions 308 generally extend towards the anterior of the walker 300, such that corresponding dorsal and posterior wing portions generally overlap each other when the shells are brought together in a closed configuration. The wing portions 306, 308 can also serve as anchor points for quick connect straps.

As can be seen in FIGS. 1-4 eyelets 316 are formed in the wing portions 308 of the posterior shell 304 and in the side shell portions 310 for selectively receiving and retaining a protruding portion of a strap 320 or buckle assembly 322. The eyelets 316 have a larger sized section for receiving a head 326 of a protruding portion 324 of a strap or buckle assembly, and a reduced size section that forms a seat 318. The seat 318 can be in the form of a slot for engaging a reduced size section 328 of a protruding portion 324 of a strap or buckle assembly.

The buckle assemblies 322 can be constructed in a similar configuration and function in a similar manner as described in U.S. Pat. No. 7,198,610, incorporated by reference above.

As can be seen in particular in FIGS. 1-4, one end of a strap 320 is selectively securable to the posterior shell 304 via engagement of a protruding portion 324 on the strap end with an eyelet 316 and seat 318 formed in the dorsal shell. A similar protruding portion 324 is formed on a buckle assembly 322 for selective engagement with an eyelet 316 and seat 318 formed in the opposed side of the posterior shell 304. Multiple eyelets 316 can be formed along the posterior shell 304 and/or the side shell portions 310 for either use with additional straps 320 or to provide alternative locations for the existing straps 320. Exemplary connectors and receiver portions are described in detail in U.S. publication nos. 2006/0135902, published June 2006, and 2007/0185425, published August 2007, both previously incorporated herein by reference. It will be recognized that in place of the protruding portion and eyelet, other suitable connection mechanisms, such as snap fasteners or hook and loop fasteners, can be utilized.

The second end of the strap 320 includes a hook portion 332 and a loop portion 334 for selective engagement with each other in a manner understood by a skilled artisan. Specifically, the hook portion 332 and the loop portion 334 are configured such that the hooks of the hook portion 332 can releasably engage the loops of the loop portion 334. Thus, the second end of the strap 320 can be inserted through a receiving loop 330 on the buckle assembly 322 and folded over and releasably secured to itself in order to set the strap length.

Figure 4:
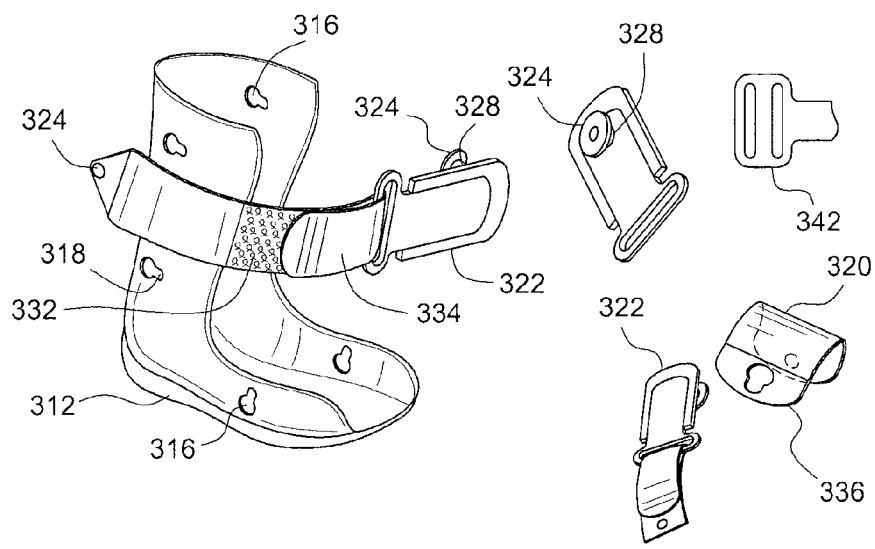
FIG. 4 is a partially exploded schematic view of the embodiment of FIG. 1.
Figure 7:
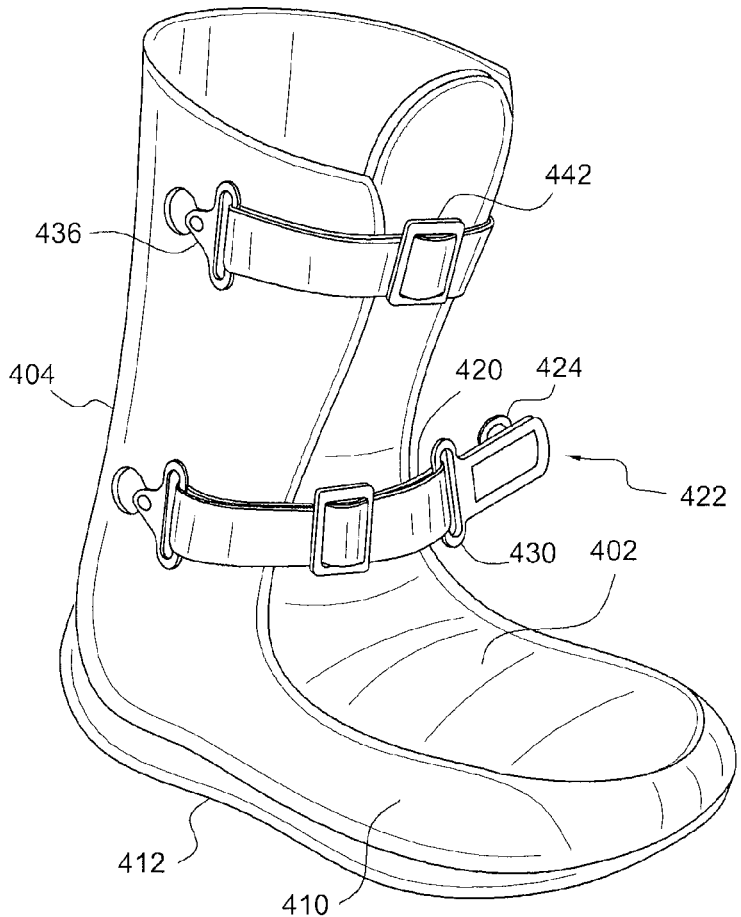
FIG. 7 is side perspective view of a variation of the embodiment of FIG. 1 utilizing the multi-loop strap adjuster shown in FIG. 4.
Figure 8:
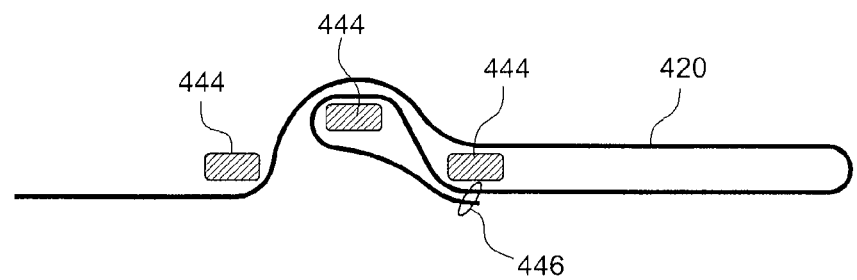
FIG. 8 is a partial sectional view of one of the straps shown in FIG. 7.

As an alternative to the hook 332 and loop 334 portions, a multi-loop strap adjuster 342, shown in isolation in FIG. 4, and in FIGS. 7 and 8, can be used to provide the desired length adjustment of the straps.

The setting of the strap length is done with both the strap 320 and the buckle assembly 322 engaged with the respective seats 318 and the buckle closed. In this manner, the length of the strap need only be set once, and from this initial setting, the strap can be tightened and loosened via opening and closing of the buckle assembly 322, and/or disengaging the protruding portions 324 of the strap 320 and/or buckle assembly 322 from the respective seat 318 and/or eyelet 316. Thus, a quick adjusting strapping system is achieved that allows for quick tightening and loosening of the straps for entry and removal of the lower leg, ankle, and foot from the walker 300.

As shown in FIGS. 1-3, at least two straps 320 are arranged to cross from opposed sides of the posterior shell 304 over the dorsal shell 302 for bringing the two shells closer together for tightening the walker around the lower leg, ankle, and foot.

An additional strap 320, having a slightly different configuration, is shown in FIGS. 1-4 as crossing over the dorsal aspect of the foot and dorsal shell 302 in the region of the toes of the foot.

The strap 320 in the toe region of the foot is similar to the other straps, with the exception of an additional eyelet 316 and seat 318 formed in a connecting element 336. The protruding portion 324 of the buckle assembly 322 is selectively engaged with the eyelet 316 and seat 318 formed in the connecting element 336 to provide an additional quick release connection to aid with tightening and loosening of the straps. It will be recognized that any of the disclosed strap configurations can be substituted for any other disclosed strap configuration. It will also be recognized that the eyelets 316 and the protruding portions 324 can all be made to be interchangeably sized such that the orientation of the straps 320 can be alternated from a leftward to a rightward orientation, and vice versa.

Figure 5:
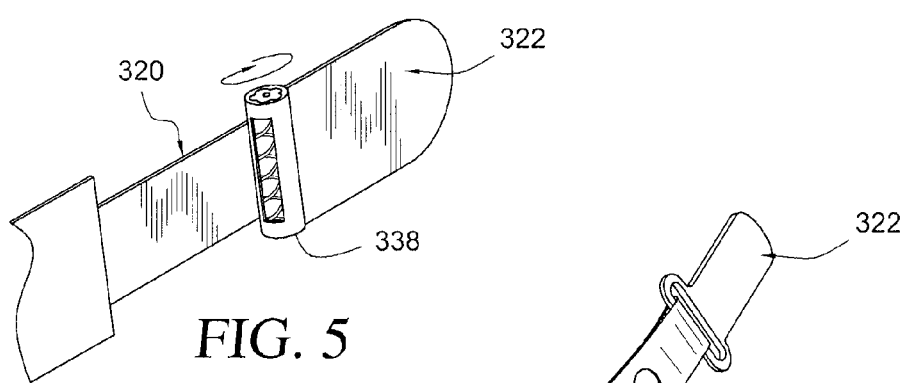
FIG. 5 is a schematic view of an alternate strap configuration for use with the embodiment of FIG. 1.

In a variation shown in FIG. 5, in place of either the hook 332 and loop 334 portions or the multi-loop strap adjuster 342, a manual or automatic self winding element 338 can be provided in order to take up excess strap length prior to closing the buckle assembly 322. Such an automatic self winding mechanism can include a spring loaded element that is tensioned to draw in the excess strap length prior to closing the buckle assembly 322. In this manner, the additional step of manually adjusting the strap length, as described above, can be eliminated, thus further easing the donning and doffing of the walker, and the tightening of the straps.

Figure 6:
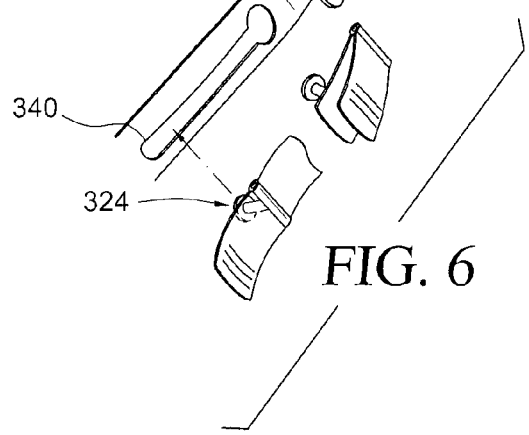
FIG. 6 is a schematic view of an alternate strap configuration for use with the embodiment of FIG. 1.

In yet another variation, as shown in FIG. 6, a protruding portion 324 can be attached to the second end of the strap for selective engagement with an excess strap retention slot 340 formed in the dorsal 302 or posterior 304 shells. Once the length of the strap has been adjusted, the excess strap length at the second end of the strap can be prevented from excessive movement or flapping by engaging the protruding portion 324 attached to the second end of the strap with the excess strap retention slot 340. Thus, inadvertent loosening of the strap can be prevented.

As briefly mentioned above, a further variation of a circumferential walker 400 utilizing a multi-loop strap adjuster 442 in place of hook and loop portions on the strap 420 is shown in FIGS. 7 and 8.

The walker 400 is constructed in the manner discussed above with a dorsal shell 402, a posterior shell 404, side shell portions 410, and an outsole portion 412.

In a variation from the embodiment discussed above, each of the straps 420 are anchored at a first end to the walker 400 along the posterior shell 404 via connecting elements 436, which can be permanently fixed to, or integrally molded with the posterior shell 404. Of course, the straps may alternatively be removably attached in a manner discussed above or below.

As shown in FIGS. 7 and 8, the second ends 446 of the straps 420 are looped through a receiving loop 430 of a buckle assembly 422, wound around the segments 444 of the multi-loop strap adjuster 442, and secured to the strap 420 itself via threading, ultrasonic welding, or any other suitable permanent or non-permanent attachment method.

In use, a protruding portion 424 of the buckle assembly 422 is removably secured to an eyelet and seat formed in the posterior shell 404, as shown in FIGS. 1-4 and discussed in detail above. Of course, the buckle assembly 422 can be removably attached to the posterior shell 404 in any suitable manner previously discussed. Once the buckle assembly is secured to the posterior shell 404, the multi-loop strap adjuster 442 can be manipulated via sliding along the main portion of the strap 420 to adjust the overall strap length, similarly to the methods previously discussed.

Thus, as discussed above in detail, the length of the straps 420 need only be adjusted once, and subsequent engagement and disengagement of the straps 420 to tighten the walker 400 around the lower leg, ankle, and foot are accomplished via the quick connect structure of the buckle assemblies 422, which are removably connected to the posterior shell 404. This configuration provides quicker and easier donning and doffing of the walker 400 for all users and in particular for infirm or elderly persons.

Additionally, the straps can be set once by a clinician in a controlled setting to a specified tightness such that the patient does not need to further adjust the straps outside of the presence of the clinician. In order to prevent the unauthorized adjustment of the straps outside of the presence of the clinician, a removable and reusable clamp that can only be removed by the clinician can be utilized to engage the straps such that the patient cannot further adjust the length thereof. The straps can also include indicia to track certain settings by way of the length of the strap.

If further adjustment of the strap lengths is necessary in order to accommodate, for example, a decrease in swelling of the lower leg, ankle, and foot, a patient can revisit the clinician for professional adjustment of the strap lengths.

In further variations, the straps can be threaded through slots in the dorsal shell in order to prevent the dorsal shell from migrating along the dorsal aspect of the foot, ankle, and lower leg. Additionally, the straps may be connected to or fed along the interior surfaces of the posterior shell in order to provide a further low profile brace, with even less chance that the straps may inadvertently catch on external objects and become damaged or loosened.

A further variation of the embodiment of FIGS. 1-4 is shown in FIGS. 9-13 utilizing an alternative quick connecting strap configuration. As previously discussed, a circumferential walker 500 includes a dorsal shell (not shown in order to illustrate other features, see dorsal shells in FIGS. 1-4 and 7), a posterior shell 504, side shell portions 510, and an outsole 512. The side shell portions 510 can wrap around the anterior portion of the walker 500 to form a toe protector portion.

Similarly to the above discussed embodiments, a number of quick connect strap assemblies are attached to the walker to provide quick and easy tightening of the straps for providing the desired amount of support to the lower leg, ankle, and foot. The quick connect strap assemblies also make donning and doffing the walker easier for all users, in particular infirm or elderly users.

As shown in FIGS. 9 and 13, each strap 520 includes a first end having a ratchet or toothed portion 534, and a second end that carries a buckle assembly 522. The toothed portion 534 carries teeth that are oriented in a first direction for corresponding engagement with complementary ratchet or toothed portion 546 in a connecting assembly 536, which carries teeth that are oriented in a second, opposed direction to the teeth on the first end of the strap 520.

The connector assembly 536 is shown in FIGS. 9 and 12 and includes the aforementioned toothed portion 546, a connecting element 538 (generally in the form of a plate element) pivotally attached to the connector assembly 536 at pivot point 540, and a gap or slot 544 for receiving the excess strap at the first end of the strap 520.

The first, toothed end 534 of the strap 520 is inserted under the connecting element 538 via the gap or slot 544. The connecting element 538 acts as a lever that pivots about the pivot point 540 and includes an actuation surface or actuation point 542, which can be actuated via the application of pressure to rotate the connecting element 538 about the pivot point 540 in order to increase the size of the gap or slot 544. This actuation of the connecting element 538 can aid with inserting the first toothed end 534 of the strap 520 into the gap or slot 544, or to release the engagement of the toothed portion 534 of the strap 520 with the complementary shaped toothed portion 546 of the connecting assembly 536.

The connecting assembly 536 can be integrally formed with the posterior 504 and side 510 shell portions, or it can be separately formed and attached to the posterior 504 and side 510 shell portions in any suitable manner, such as ultrasonic welding or the use of adhesives.

Referring again to FIGS. 9 and 13, the second end of the strap 520 carries a buckle assembly 522 that includes a pivoting portion 530 that pivots about the end of the strap 520 at pivot point 532. The pivoting portion also includes a first locking protruding portion 524 and a second nose protruding portion 526, each carried along one surface thereof.

The buckle assembly 522 is configured to selectively engage a locking element 514, which is shown in FIGS. 9-11. The locking element 514 can be integrally formed with the posterior 504 and side 510 shell portions, or it can be separately formed and attached to the posterior 504 and side 510 shell portions in any suitable manner, such as ultrasonic welding or the use of adhesives.

The locking element 514 includes nose 516 and locking 518 hooks that provide selective engagement for the corresponding and complementary shaped first locking protruding portion 524 and a second nose protruding portion 526 carried on the buckle assembly 522.

In use, the user places the lower leg into the interior space of the walker 500 defined between the dorsal and posterior 504 shells. Then, the first toothed ends 534 of the straps 520 are inserted a short distance into the gap or slot 544 of the connecting assemblies 536 to engage the straps 520 therewith. Next, the first locking protruding portion 524 and the second nose protruding portion 526 carried on the buckle assemblies 522 are inserted and engaged with the nose 516 and locking 518 hooks of the locking elements 514 such that the pivoting portions 530 are engaged with the locking elements 514 in a flush manner. Lastly, the first toothed ends 534 of the straps 520 are further inserted into the gap or slot 544 of the connecting assemblies 536 in order to provide the appropriate amount of tightening in order to provide the desired amount of support and stabilization to the lower leg, ankle, and foot.

Of course, variations of these steps are contemplated. For example, the first toothed ends 534 of the straps 520 can be further inserted into the gap or slot 544 of the connecting assemblies 536 prior to engaging the pivoting portions 530 with the locking elements 514. If such a step causes the straps 520 to be too tight, the straps 520 may be subsequently loosened a desired amount by actuating the connecting element 538 to release the straps 520 in order to achieve the desired amount of tightening and support.

As previously discussed, the strap lengths can thus be adjusted once, and subsequent donning and doffing of the walker 500 does not require readjustment of the strap lengths, but merely engagement of the pivoting portions 530 with the locking elements 514 to provide a quick connecting strap assembly.

As can be seen from the illustrations and the above discussion, the dorsal and posterior shell configurations utilizing the quick connect strap configurations provide low profile walkers that ease donning and doffing of the walkers, and also eases tightening of the straps for adjustment.

Additional features, such as inflatable liners with integrally attached pumps, which can provide compression therapy and/or aid with properly fitting the walker to the lower leg, a foam midsole to control heel strike and roll over, and or a fabric exterior covering for the shell portions or a sleep cover accessory to aid with preventing undesired contact with the hard surfaces of the walker may also be provided. Further, the midsole can be formed with different materials or geometries to control heel strike, toe off, and energy return. An integrated adjustable heel platform or wedge can also be provided.

Additionally, the shell portions may be formed from appropriately resilient materials or have particular resilient portions that allow the shell portions to better conform to the geometry of the user's lower leg. In such a case, the rigidity and stabilization for the support are provided via the tightening of the quick connect strap configurations about the resilient portions.

C. Detailed Description of a Hinged Circumferential Walker

As shown in FIGS. 14-24, the hinged circumferential, clam-shell like walker 1100 is configured in an essentially two-piece construction to provide a sleek and low profile device for use in stabilizing and supporting the lower leg. Numerous advantages are obtained from such a configuration, such as lower weight, and less opportunity for the device to catch on external objects or clothing. Any weight savings will be a substantial benefit, as a user must swing the mass of the walker, along with the leg, through the gait cycle.

The walker 1100 includes a semi-rigid, or substantially rigid shell configuration as previously described. The walker 1100 includes a posterior shell 1118 that extends from a posterior side of the lower leg and ankle, along the distal surface of the foot, and terminates in a plantar shell portion 1122 that extends along the plantar surface of the foot. The posterior shell 1118 includes lateral and medial (first and second) wing portions 1134 that extend partially around the lower leg, ankle, and foot from the posterior shell 1118 to wrap around the leg in order to at least partially enclose and support the lower leg.

A dorsal shell 1102 is correspondingly shaped to the posterior shell 1118 to at least partially surround or enclose the lower leg, ankle, and foot to provide protection, support, and stabilization thereto. The walker 1100 can thus be formed in a clamshell-like configuration to fully encase and protect the lower leg, ankle, and foot. The dorsal shell 1102 is formed either in a single piece or in multiple shell portions. In the exemplary embodiment, the dorsal shell 1102 includes a proximal shell portion 1104 that is connected to a distal shell portion 1106 via a flexible or resilient portion or hinge connection 1108.

The connecting portion 1108 may be a flexible or resilient material positioned between the proximal and distal shell portions 1104, 1106 along the dorsal surface of the ankle and/or foot of a user in order to provide a comfort fit between the walker and the ridge of the foot and ankle. This connecting portion may be formed via overmolding a different material onto the end portions of the proximal and distal shell portions 1104, 1106 to form a flexible or resilient expansion portion or mechanism. For example, the connecting portion can be formed via a flexible plastic or elastomer, such as, for example, ethylene vinyl acetate (EVA). Of course, any suitable flexible material may be utilized, including silicone or natural or synthetic rubbers. Alternative hinge mechanisms, such as pivot pins and sleeves, or piano or butterfly hinges, can also be used.

Overmolds and overmolding techniques are described in detail in U.S. Pat. No. 5,951,504, granted Sep. 14, 1999, U.S. Pat. No. 7,018,351, granted Mar. 28, 2006, U.S. Pat. No. 7,288,076, granted Oct. 30, 2007, and U.S. Pat. No. 7,311,686, granted Dec. 25, 2007, all commonly owned and incorporated herein in the entirety by reference.

The connecting portion 1108 will reduce or eliminate the formation of a pressure point along the dorsal surface of a user's lower leg, ankle, or foot. Further, due to the flexible nature or resiliency of the connecting portion, when the dorsal shell 1102 is closed around the user's lower leg, ankle, or foot, different sized anatomies can be accommodated using the same sized walker 1100. Additionally, the walker 1100 will automatically expand or contract due to swelling or reduction of swelling of the lower leg, ankle, and foot of a user.

Figure 15:
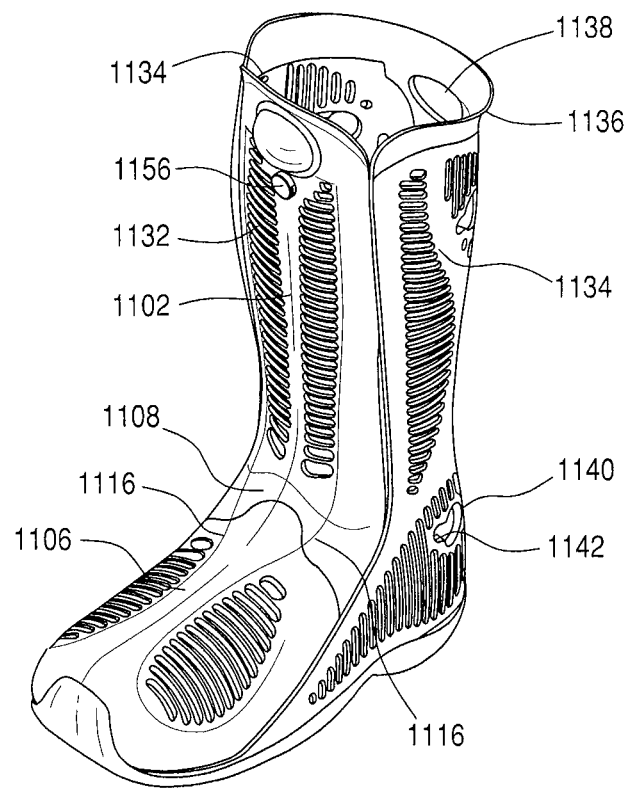
FIG. 15 is a perspective view of the walker of FIG. 14 with the straps removed for clarity.
Figure 16:
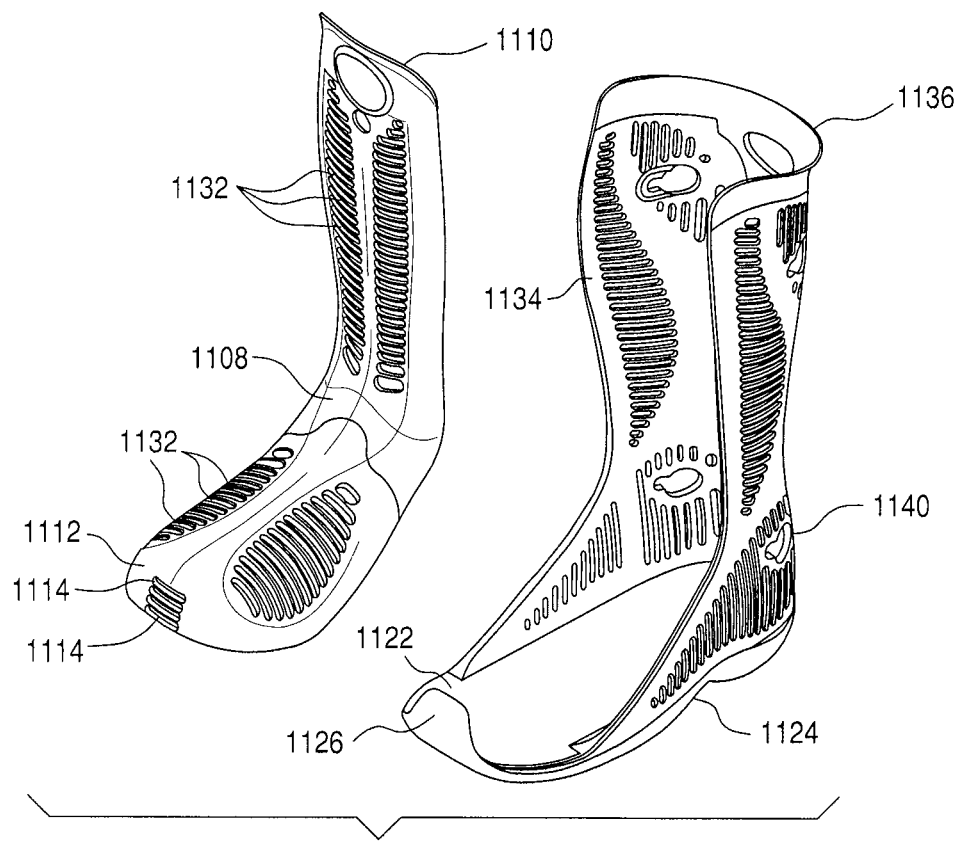
FIG. 16 is an expanded perspective view of the dorsal and posterior shells of the walker of FIGS. 14 and 15 with the straps removed.

As seen best in FIGS. 15 and 16, the proximal portion of the distal shell 1106 extends proximally to create a narrow portion of the connecting portion 1108. In this manner, the distal shell 1106 provides a secure point for a strap (discussed below) to extend over for transferring the closing force of the strap through the distal dorsal shell portion 1106.

As best seen in FIGS. 14, 16, 18, 21, and 22, the proximal portion 1104 of the dorsal shell 1102 includes a flexible or resilient edge 1110 along the terminal portion thereof. The edge 1110 can be formed via overmolding as discussed above. The edge 1110 can therefore act as an expansion mechanism to flex to accommodate different sized lower legs of different users. The edge 1110 also reduces or eliminates pressure points along the edge of the dorsal shell 1102. Therefore, a comfortable fit is achieved for numerous users having different sized anatomies.

Figure 14:
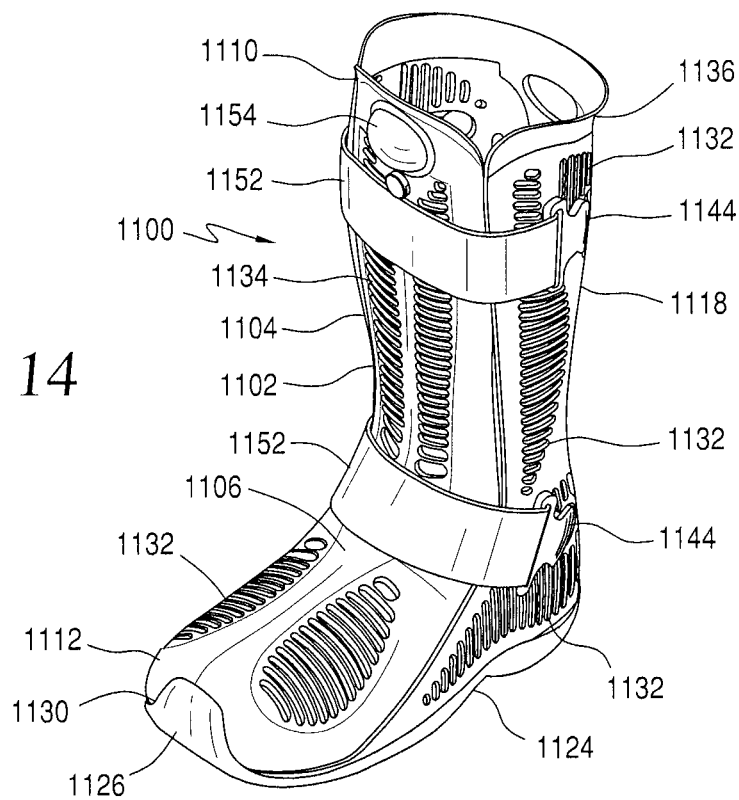
FIG. 14 is a perspective view of an embodiment of a hinged circumferential walker in accordance with the present disclosure.

As shown in FIGS. 14, 15, and 16, the distal portion 1106 of the dorsal shell includes a toe cover or protector portion 1112 that is configured to enclose the foot and toes of a wearer and provide protection thereto. The anterior portion of the toe cover 1112 also includes receiving openings or slots 1114 formed therein to cooperate with one or more projections 1128 formed along an extending toe portion 1126 of an outsole 1124 to form an adjustable hinge point 1130 between the dorsal and posterior shells 1102, 1118. While the projections 1128 and openings 1114 are shown to be elongated, any suitable shape can be utilized. Additionally, while a single projection 1128 and opening 1114 is shown at any particular plane, it will be recognized that a plurality of projections 1128 and openings 1114 can be provided at each plane.

The outsole 1124 can be integrally formed or attached along the plantar shell portion 1122 of the posterior shell 1118, for example, via overmolding as discussed above. The outsole can be formed from any suitable material, for example, a shock absorbing or resilient material.

Figure 17:
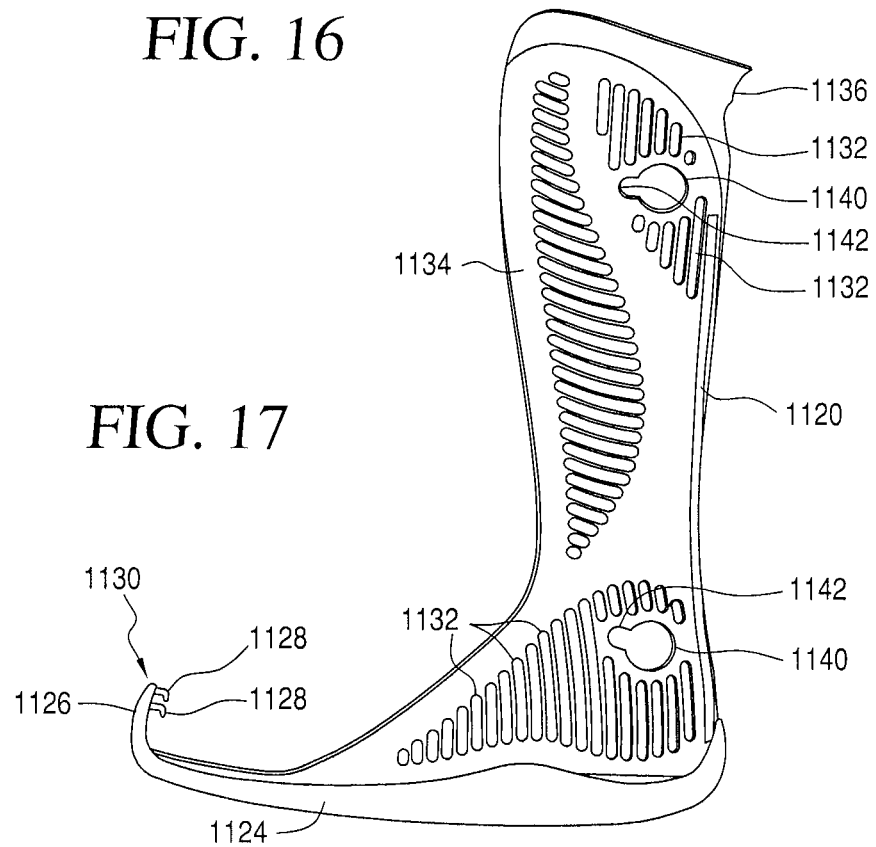
FIG. 17 is a side view of the posterior shell shown in FIGS. 14 and 15 with the straps removed.
Figure 22:
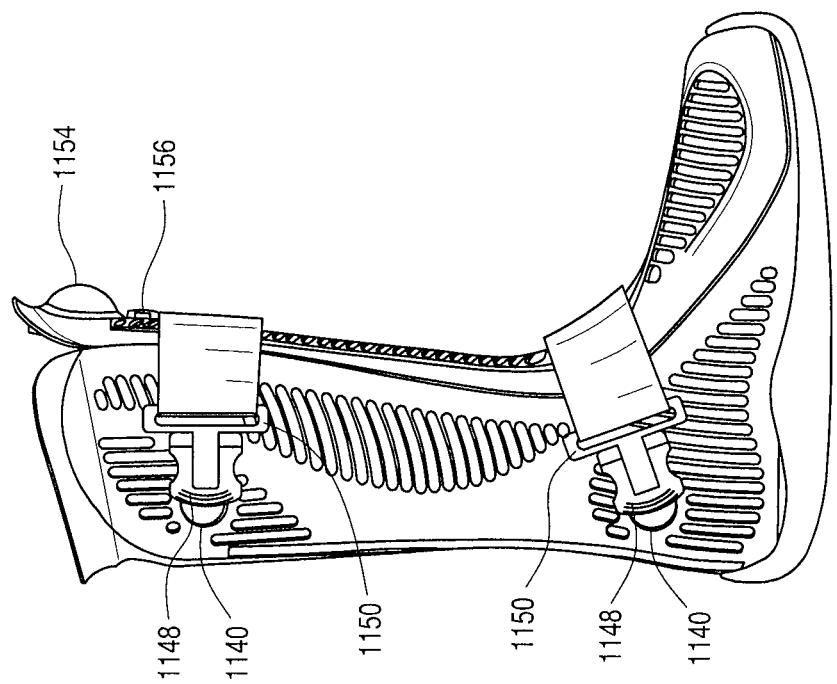
FIGS. 21 and 22 are left and right side views of the walker of FIG. 14 showing the straps and buckle and strap retaining assemblies.
Figure 21:
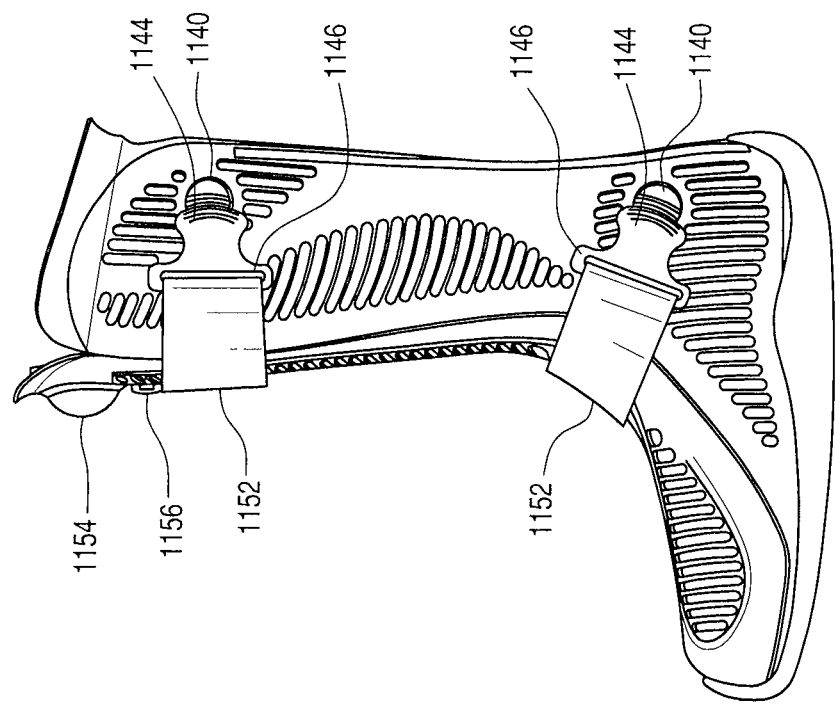

As best seen in FIGS. 17 and 19, two projections 1128 are formed along the extending toe portion 1126. It will be recognized that fewer or more projections can be used to form the adjustable hinge point 1130. The projections 1128 are formed with an enlarged portion and a reduced size portion to have a snap configuration to be selectively engaged and disengaged from the receiving openings 1114.

As best seen in FIGS. 16, 18, and 19, four receiving openings 1114 are formed in the anterior portion of the toe cover 1112 to selectively receive the two projections 1128 therein in a snap configuration. With the configuration of four receiving openings 1114 and two snap projections 1128, a user can selectively reposition the projections 1128 in at least three distinct configurations with the openings 1114 to adjust the height of the dorsal shell 1102 with respect to the plantar shell portion 1122 (a fourth configuration can be formed by inserting the uppermost projection into the lower most opening). Thus, the walker 1100 can be adjusted to accommodate swelling of the lower leg, foot, and ankle, or to accommodate different sized users. As discussed above, different numbers of projections and receiving openings can be utilized to further adapt the walker 1100 to different anatomies.

As will be recognized, the positions of the projections 1128 and openings 1114 can be altered, such that the projections extend from the toe cover 1112 and the openings are formed in the extending toe portion 1126. In an alternative variation, openings and projections can be positioned both on the toe cover 1112 and the extending toe portion 1126 in a suitable corresponding manner. Other various configurations of hinges 1130 are discussed in detail below.

As shown in FIGS. 18, 19, and 20, when the projections 1128 are engaged with the receiving openings 1114, a hinge 1130 is formed to allow the dorsal shell 1102 to be swung away from the posterior shell 1118 in a clamshell-like manner. Due to the use of two projections 1128, and the resiliency of the extending toe portion 1126, the dorsal shell 1102 is biased towards the closed position shown in FIG. 18, such that the walker 1100 will tend to automatically return to a closed configuration from the open configuration shown in FIG. 20. This will aid with donning the walker 1100, especially for infirm users.

It can be seen that a user can pull open the dorsal shell 1102 away from the posterior shell 1118, via the hinge 1130, to allow insertion of the lower leg, ankle, and foot into the walker 1100. Once the user has inserted their lower leg into the walker 1100, they can remove the opening force from the dorsal shell 1102, which will then tend to return to the closed configuration to enclose the lower leg within the walker 1100. The user can then utilize a connecting mechanism discussed below to apply pressure and support and to maintain the walker 1100 in the closed configuration.

It can be seen in FIGS. 14-24 that each of the dorsal and posterior shells 1102, 1118 include clearance holes 1132 defined therein. The clearance holes 1132 can be arranged in any suitable pattern. For example, some of the clearance holes 1132 may be arranged in a substantially horizontal orientation and some of the clearance holes 1132 may be arranged to be oriented substantially in the proximal-distal direction. The clearance holes may be oriented in the same or different directions or at the same angle or different angles. The clearance holes 1132 can also reduce the weight of the walker 1100. Further, the clearance holes 1132 can act as vents to allow heat and perspiration to pass from inside the walker 1100 to the exterior thereof. Additionally, the clearance holes 1132 may also allow the dorsal and posterior shells 1102, 1118 to have some resiliency to accommodate swelling of a limb or users having different sizes of lower legs, ankles, and feet.

As best shown in FIGS. 14, 16, 23, and 24, additional expansion mechanisms are formed in the posterior shell 1118 to reduce or eliminate pressure points and to accommodate users having different sizes of lower legs, ankles, and feet. In particular, a flexible or resilient edge and expansion joint 1136 is formed along the edges of and between the posterior of the wing portions 1134. The expansion joint 1136 can be formed having a larger dimension at the proximal end and tapering down to a smaller dimension at the distal end. The expansion joint 1136 can be overmolded as discussed above. As shown, the expansion joint 1136 includes a number (any desired) of expansion holes 1138 passing therethrough that can be arranged in any suitable manner. The holes 1138 can have any desired shape or size and can also act as vents.

Due to the resiliency or flexibility thereof, the expansion joint can expand to accommodate swelling or different sized anatomies, and can reduce or eliminate pressure points. Additionally, since the expansion joint 1136 extends along the posterior of the posterior shell 1118 between the wing portions 1134, the flexibility or resiliency of the expansion joint, aided by the expansion holes 1138, allows the proximal or upper portions of the wing portions to expand away from each other to accommodate swelling of the limb or users having different sized calves, without losing rigidity in the sagittal plane (the plane dividing the walker 1100 into medial and lateral sides). Due to the larger proximal end, the expansion joint allows more expansion between the proximal portions of the wing portions 1134 than at distally spaced positions of the wing portions 1134. The expansion joint and edges 1136 also reduce or eliminate pressure points.

As shown in FIG. 24, the thickness of the proximal, anterior portions of the wing portions 1134 can also be reduced with respect to the thickness of the rest of the posterior shell 1118 such that the wing portions 1134 may more easily expand to accommodate larger sized calves and lower legs.

Thus, in view of the above description, a walker 1100 has adjustability and expansion capabilities to accommodate users having different sized anatomies or swelling of the limb, and further to reduce or eliminate pressure points to provide a circumferential walker that has a comfortable fit for many different users.

The walker 1100 is also easy to use due to the quick connecting mechanisms, described in detail below, that allow quick and easy engaging and disengaging of straps to don and doff the walker 1100. The wing portions 1134 of the posterior shell 1118 include two pairs of eyelets 1140 that include seats 1142. The eyelets 1140 and seats 1142 selectively engage projections on strap retaining assemblies 1144 or buckle assemblies 1148. In this configuration, with the toe hinge 1130 and a sufficiently rigid distal shell portion 1106, it is only necessary to use two straps to close and secure the walker 1100. Thus, the form of the walker are more low profile to provide a cleaner appearance and to reduce possible contact with foreign objects, and donning and doffing of the walker is made easier since wearers no longer need to stretch and reach all the way to the anterior portion of the walker to apply a "toe" strap. Of course, a third "toe" strap, or any desired number of straps can be provided to add additional compression and support.

Each of the strap retaining assemblies 1144 or buckle assemblies 1148 respectively include a receiving loop or D-ring 1146, 1150 to receive a looped portion of a strap 1152 therethrough. The straps may be conventional hook and loop fastening straps to provide adjustability. As discussed in detail below, the strap length need only be adjusted an initial time (or infrequently to accommodate swelling or reduction of swelling of tissues), and each subsequent donning and doffing of the walker 1100 can be achieved utilizing the quick connecting configuration.

As seen in FIGS. 15, 18, 21, and 22, a pump assembly 1154 and a valve assembly 1156 are integrated with the dorsal shell 1102. The pump assembly 1154 and valve assembly 1156 are connected to bladders discussed in detail below that are retained within the walker 1100 to provide additional compression and support to the lower limb of the user.

The pump assembly 1154 can have any suitable configuration and may include a resilient or flexible diaphragm having an inlet (which may be a one-way inlet) and a one-way outlet to transfer air from the exterior of the pump to the bladders. Any available manual or electric pump may also be utilized or integrated into the walker 1100. The valve assembly 1156 may be a pressure release valve having single or selectable flow paths. Any available release valve and/or selector valve may be used, for example a push button release valve.

As shown in FIGS. 15 and 23, the walker 1100 may have structures designed to selectively strengthen the dorsal or posterior shells 1102, 1118 in a specific direction. In particular, the dorsal shell 1102 can include a reinforcing ridge 1116 that extends generally longitudinally along both lateral and medial sides thereof. Additionally, the posterior shell 1118 can include a reinforcing ridge 1120 positioned to the posterior of the eyelets 1140 and oriented generally in the proximal-distal direction thereof.

In addition to adding structural support, the reinforcing ridges 1116 and 1120 can also enhance the low profile form of the walker. The reinforcing ridges 1116 can further provide additional support for engaging the straps 1152 to provide sufficient support and stabilization to the lower leg of the user.

Variations and further explanations of components for a hinged circumferential walker are provided below.

D. Variation of a Posterior Shell for Use with a Hinged Circumferential Walker

Figure 26:
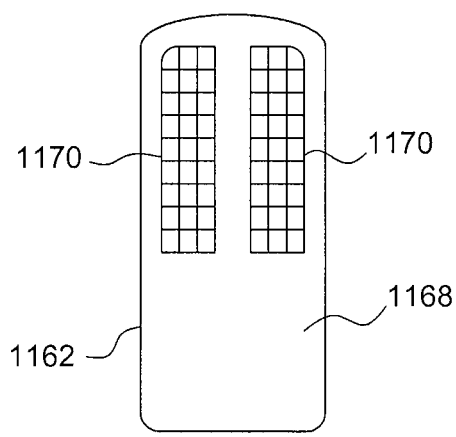
FIG. 26 is a bottom view of the posterior shell of FIG. 25.

A variation of a posterior shell 1160 for use with a hinged circumferential walker is shown in FIGS. 25 and 26. The posterior shell 1160 has generally the same configuration as previously described, including a plantar shell portion 1162.

An indentation or groove 1164 is provided along the medial-lateral axis of a proximal surface 1166 of the plantar shell portion 1162. The indentation or groove 1164 can extend along the entire length of the plantar shell portion 1162 or over only a portion thereof. The indentation may act as a guide for an inflation tube for bladders, as will be discussed in detail below, such that the inflation tube will not be compressed to cause blockage thereof.

The posterior shell 1160 also includes wings 1174, as described above. Eyelets 1176 and seats 1178 are provided in the shell wings 1174 to selectively anchor and retain buckle assemblies and strap retaining assemblies. In this variation, three sets of eyelets 1176 and seats 1178 are positioned in the shell wings 1174 so that three straps can be used to tighten and close the walker. It will be recognized that any desired number of sets of eyelets can be provided to accommodate any desired number of straps.

The posterior shell 1160 and wings 1174 also include clearance holes 1172 to add to the low profile form, to reduce weight, to provide venting of heat and perspiration, and to provide some resiliency to the posterior shell 1160 and wings 1174 in the same manner as discussed above. The clearance holes 1172 may be arranged in any suitable configuration, as previously discussed.

As shown in FIG. 25, each seat 1178 has associated therewith a buckle rotation restriction groove 1180. As will be discussed in detail below, the buckle rotation restriction groove 1180 cooperatively engages with a protrusion on the buckle assembly or strap retaining assembly to limit the amount that the straps can move. Thus, the straps are maintained in position on the walker to provide the appropriate amount of stabilization and support to the user's lower leg.

As also shown in FIG. 25, the posterior shell 1160 also includes reinforcing ridges 1182 positioned in the posterior of the shell and extending in the proximal-distal direction. The reinforcing ridges 1182 function in the same manner as previously discussed.

As also previously discussed, an expansion joint and resilient or flexible edge 1184 is positioned between the posterior of the wing portions 1174 and extending in the proximal-distal direction. In this variation, the expansion joint 184 includes expansion openings 1186 that are horizontally oriented and which provide the same function as the expansion holes 1138 discussed above. The expansion openings 1186 can decrease in length from the proximal end to the distal end of the expansion joint 1184 corresponding to the tapered shape of the expansion joint 184.

As shown in FIG. 26, the plantar shell portion 1162 also includes a distal surface 1168. Protruding ribbing 1170 may be formed on the distal surface 1168 in a length-wise and/or cross-wise manner to create wells, and thus to provide additional support and reinforcement to the toe-off area of the walker. Such ribbing 1170 can be provided to the plantar shell portion of any posterior shell disclosed herein to provide additional support and reinforcement to the toe-off area of the walker. The protruding ribbing can extend over the entire length of the distal surface 1168, or over any desired portion thereof Next, variations of bladders for use with hinged circumferential walkers to apply compression therapy to a limb are discussed.

E. Various Bladder Configurations for Use with a Hinged Circumferential Walker

Figure 27:
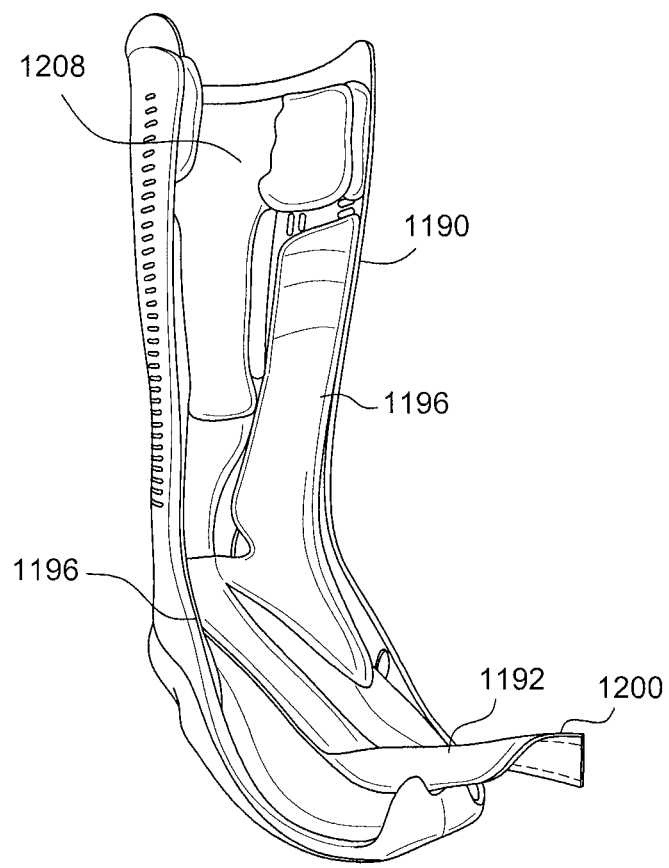
FIG. 27 is a perspective view showing the bladders and padding of a variation of the walker of FIG. 14.
Figure 28:
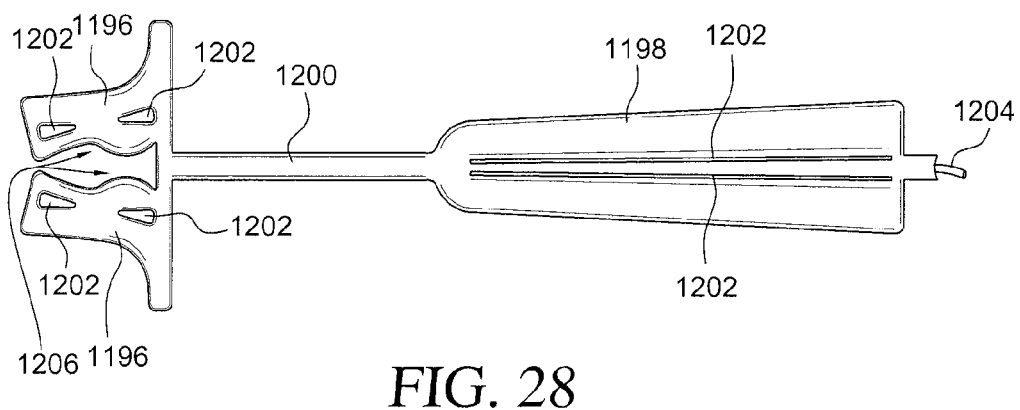
FIG. 28 is a top view of the bladders of FIG. 27.
Figure 29:
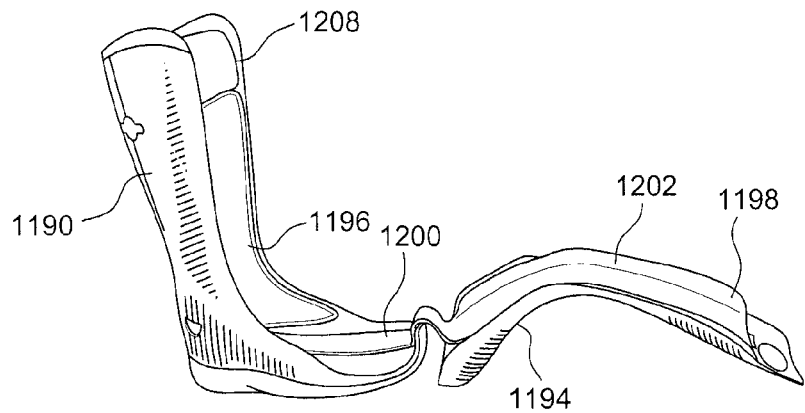
FIG. 29 is a side view of the posterior shell, bladders, and dorsal shell of the variation shown in FIG. 27.

As shown in FIGS. 27-29 a bladder configuration for use with hinged circumferential walkers is illustrated. The walker is constructed in any suitable manner as discussed herein and includes a posterior shell 1190 having a plantar shell portion 1192, and a correspondingly shaped dorsal shell 1194. The bladders can be inflated or deflated via associated inflation ports or integrally carried pumps. The inflation port or pump may be integrally carried in a clearance hole of the walker shells. A single pump can be provided to inflate one or more bladders simultaneously or individually to different pressures, or each bladder may be provided with an associated pump. The pumps are attached or carried by the walker so that they are not easily misplaced. Further, the pumps or inflation ports can be configured to be usable with a fluid or liquid to provide hot and/or cold therapy.

The inflatable bladders can also be configured to be ventilated by having slits passing through welded portions of the bladders. The welded portions can be used to create chambers within the bladders, and the use of more welded portions provides more chambers, as well as more slits to enable greater ventilation.

As shown in FIGS. 27-29, a configuration of medial, lateral, and dorsal bladders 1196, 1198 are shown. The medial and lateral bladders 1196 are generally shaped to correspond to the medial and lateral side portions of the posterior shell 1190. The dorsal bladder 1198 is generally shaped to correspond to the dorsal shell 1194. The medial and lateral bladders 1196 each include a bulged portion 1206 that is arranged to be located in the posterior portion of the walker. The bulged portions 1206 fill in the space around the Achilles tendon so that the lower leg will fit snugly within the walker, and so that the ankle is securely locked in position. The bladder shapes are further optimized to focus compression where it is needed and uniform compression is provided to all areas of the anatomy where the bladders provide compression.

The medial, lateral, and dorsal bladders 1196, 1198 are connected via a connecting portion 1200 that extends from one end of the dorsal bladder 1198 to a central portion of the medial and lateral bladders 1196. The connecting portion 1200 extends from the dorsal bladder 1198 at the dorsal shell hinge portion and along the plantar shell portion 1192 under the arch and plantar surface of the foot (an indentation or groove of the type shown in FIG. 25 can be used to prevent blocking of the connecting portion 1200). Thus, all of the bladders 1196, 1198 can be simultaneously inflated via the inflation tubing 204 connected to an opposed end of the dorsal bladder 1198. The inflation tubing is connected to a pump, such as described above.

The bladders 1196, 1198 can be formed of two sheets of air impervious plastic material that is welded around the edges to create air chambers therebetween. Perspiration wicking material can be applied to the surfaces of the bladders 1196, 1198 that are configured to contact the wearer's anatomy. The bladders 1196, 1198 can be secured to the interior of the walker in any suitable manner, such as, for example, via adhesive, hook and loop fasteners, or snap fasteners.

In addition to the welds forming the bladders, welds and/or holes 1202 are arranged in the bladders 1196, 1198 to serve a number of functions. The welds 1202 in the bladders 1196, 1198 can serve to direct airflow within the bladders and also to provide heat and perspiration wicking channels along the surfaces of the bladders 1196, 1198.

In addition to the bladders 1196, 1198, foam or other types of padding 1208 can be provided to reduce pressure points along the interior of the walker. The padding 1208 can be any suitable padding and can be secured to the interior of the walker in any suitable manner, such as via adhesive, hook and loop fasteners, or snap fasteners.

Figure 30:
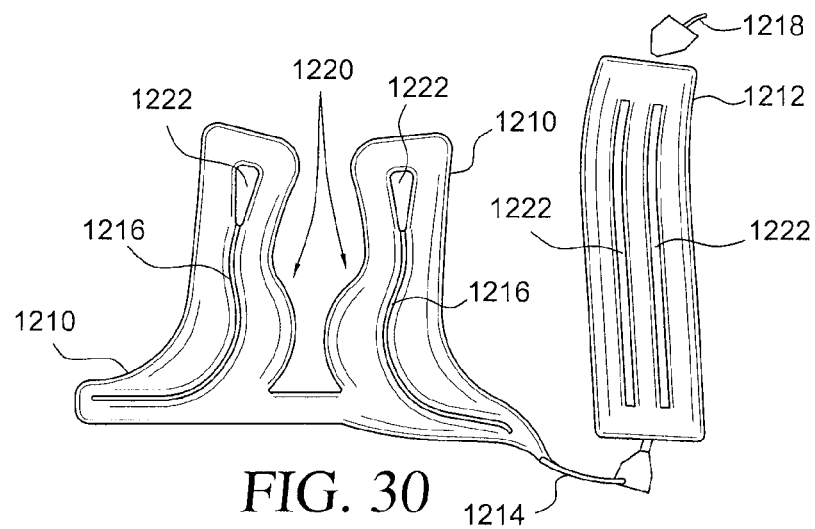
FIG. 30 is a top view of a variation of the bladders shown in FIGS. 27-28.

A further variation of a bladder configuration for use with a hinged circumferential walker is shown in FIG. 30. Medial and lateral bladders 1210 are connected to a dorsal bladder 1212 via a connecting portion or tubing 1214. The medial and lateral bladders 1210 and the dorsal bladder 1212 are shaped in a similar manner as discussed above. The medial and lateral bladders 1210 include the bulged portions 1220 as discussed above to surround and support the area around the Achilles tendon. Additionally, the dorsal bladder includes an inflation tube 1218 connected at one end thereof.

The dorsal bladder 1198 includes longitudinally extending openings 1222 that provide venting for heat and perspiration. The welds that form openings 1222 also form air flow channels and chambers within the dorsal bladder 1198 to guide airflow from the dorsal bladder 1198 to the connecting portion 1214.

The connecting portion 1214 extends along a proximal surface of a plantar shell portion under the arch and plantar surface of the foot and connects to one end of either the medial or lateral bladder 1196. In this manner, the bladders 1196, 1198 can be simultaneously inflated or deflated via the use of a pump assembly and valve assembly as previously discussed.

The medial and lateral bladders 1196 also include a central welded portion 1216 that extends along the bladders 1196 to provide a heat and perspiration dissipation channel. The welded portion 1216 extends to a position near an opening or vent 1222 in the bladders 1196 so that heat and perspiration can rise along the welded portion 1216 to be vented from the openings 1222. The openings 1222 in the bladders 1196 are appropriately shaped to provide breathability to the bladders 1196 without degradation of compression being applied to the lower limb.

Figure 31:
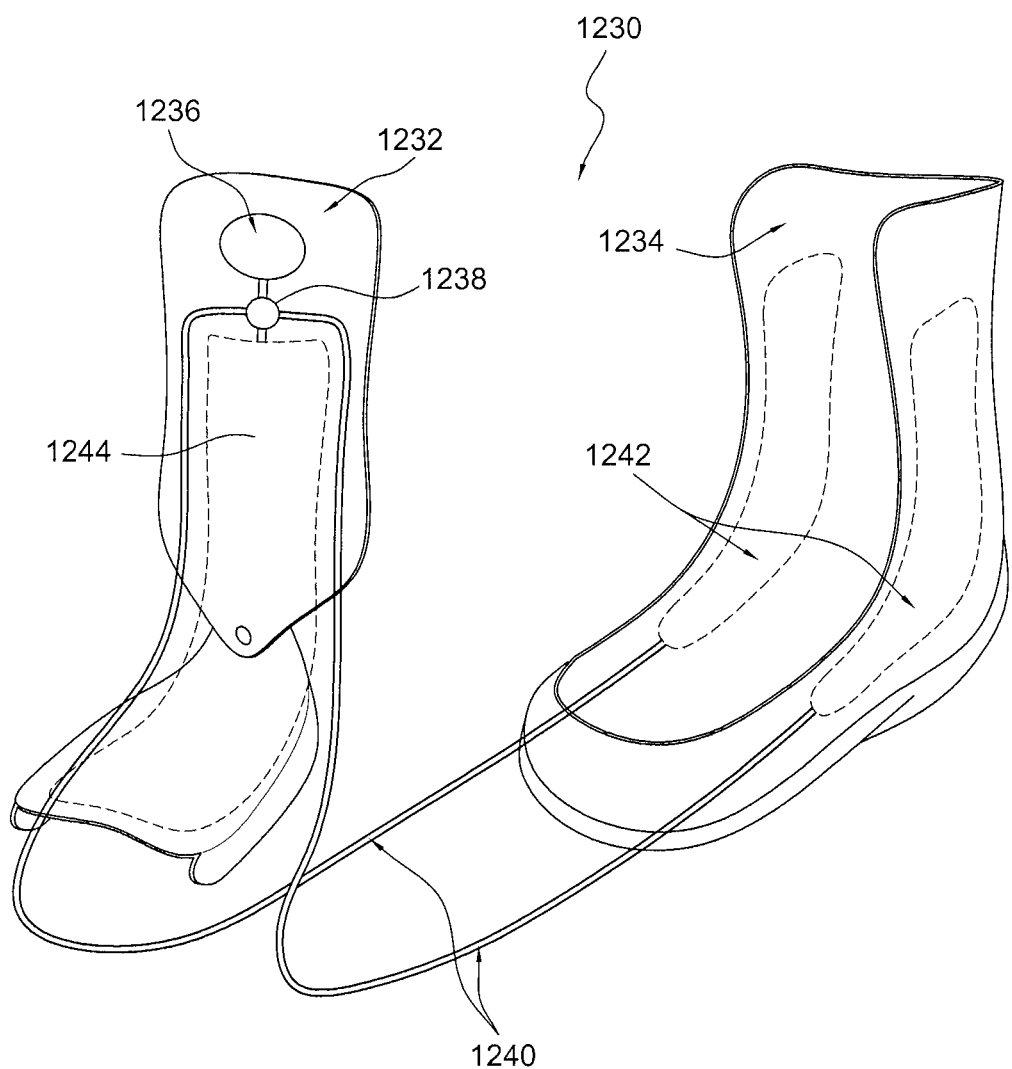
FIG. 31 is a perspective view of a further variation of the bladders for use in a circumferential walker.
Figure 32:
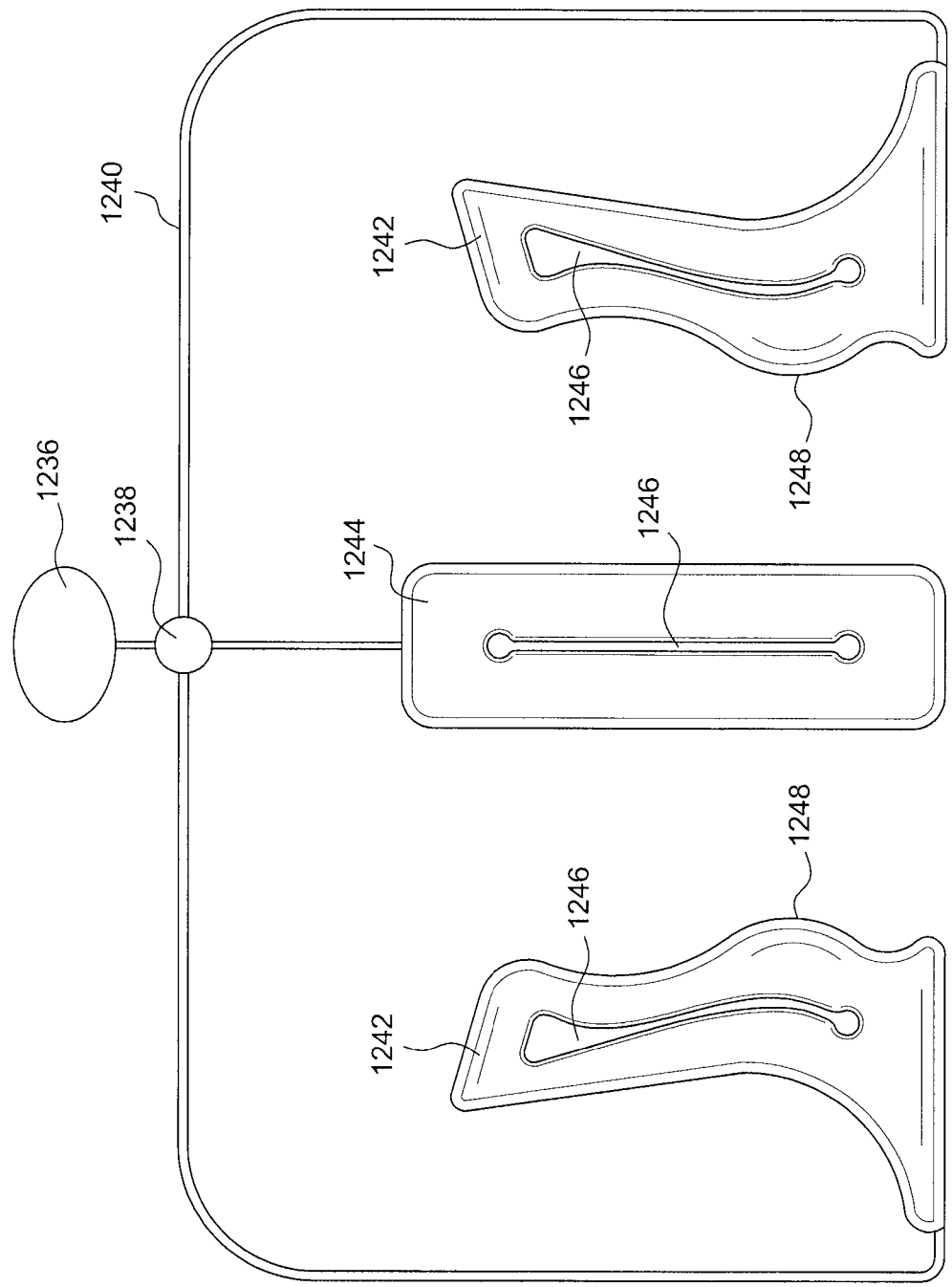
FIG. 32 is a top view of a variation of the bladders shown in FIG. 31.
Figure 33:
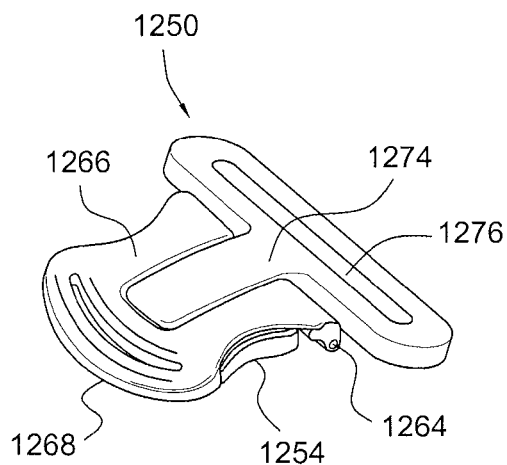
FIG. 33 is a perspective view of a buckle assembly for use with the various embodiments of a walker described herein.

A further variation of a bladder assembly for use with a hinged circumferential walker 1230 is shown in FIGS. 31 and 32. The walker 1230 includes a dorsal shell 1232 and a posterior shell 1234. A pump assembly 1236 is integrated into the proximal portion of the dorsal shell 1232 and is connected to a selector/release valve assembly 1238, which is also integrated into the dorsal shell 1232.

The selector/release valve assembly 1238 is connected to medial and lateral bladders 1242, and a dorsal bladder 1244 via independent inflation tubing 1240. Thus, the selector/release valve assembly 1238 can be used to selectively inflate or deflate different bladders to provide more or less compression to different portions of the anatomy. The inflation tubing 1240 for the medial and lateral bladders 1242 extends along medial and lateral sides of the posterior shell 1234 to one end of the medial and lateral bladders 1242.

As shown in FIG. 32, the dorsal 1244 and medial and lateral bladders 1242 have a similar shape as previously discussed. The medial and lateral bladders 1242 include the bulged portions 1248 to surround and support the Achilles tendon area of the lower leg, as discussed above.

Additionally, each of the bladders 1242, 1244 include weld portions or openings 1246 to act as airflow guides and heat and perspiration dissipation channels or venting openings as previously discussed.

Although medial and lateral bladders 1242 and a dorsal bladder 1244 are illustrated, some of these bladders may be removed, or additional bladders may be added in order to concentrate compression onto specific areas of the anatomy. For example, an additional planter bladder can be positioned under the arch and/or plantar surface of the foot in order to provide arch support.

Next, a buckle assembly for use with circumferential walkers is described.

F. Buckle Assembly for Use with a Hinged Circumferential Walker

The buckle assembly 1250 shown in FIGS. 33-36 has the same configuration as the buckle assembly 1148 mentioned above.

Figure 34:
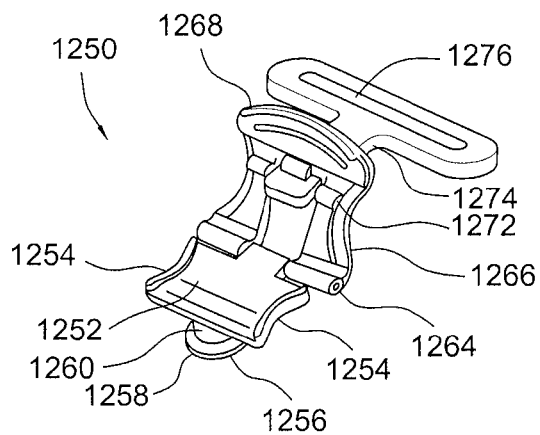
FIG. 34 is a perspective view of the buckle assembly of FIG. 33 shown in an open or release configuration.

As shown in FIG. 34, the buckle assembly 1250 includes a main portion 1252 connected via a first hinge 1264 to a clamping portion 1266. The clamping portion 1266 is connected via a second hinge 1272 to a strap retaining portion 1274.

The main portion 1252 includes ergonomically shaped finger indents or grips 1254 that enhance the wearer's ability to grip and attach the main portion 1252 to the shell of the walker.

Figure 35:
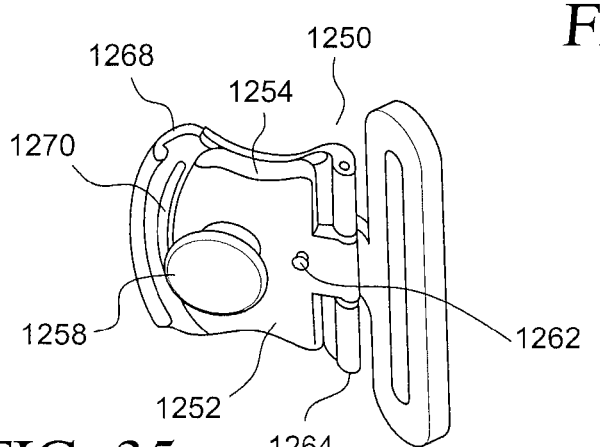
FIG. 35 is a rear view of the buckle assembly shown in FIG. 33.

As shown in FIG. 35, the main portion 1252 also includes a protruding portion 1256 extending from a surface thereof. The protruding portion 1256 includes a head portion 1258 and a reduced size portion 1260. The head portion 1258 and a reduced size portion 1260 are configured to engage the eyelet 1280 and seat 1282 in the posterior shell wing 1278 (FIG. 36) in a recognized manner. Thus, the buckle assembly can be selectively attached and detached from the posterior shell wing 1278.

Figure 36:
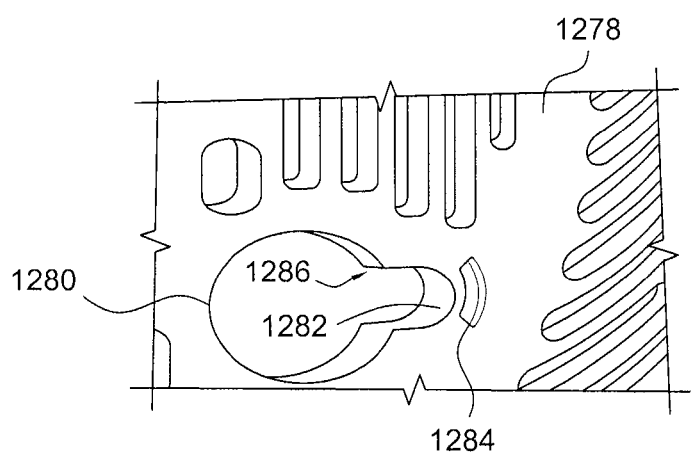
FIG. 36 is a close up view of an eyelet for use with the various embodiments of a walker described herein to connect the buckle assembly shown in FIGS. 33-35 thereto.

As further shown in FIG. 36, a reduced dimension or locking portion 1286 is formed between the eyelet 1280 and the seat 1282. The reduced size portion 1260 of the protruding portion is sized to be slightly larger than the locking portion 1286, such that when the reduced size portion 1260 is seated within the seat 1282, the locking portion 1286 provides a snap engagement thereof to prevent inadvertent removal of the reduced size portion 1260 and the buckle assembly 1250 from the seat 1282.

As further shown in FIG. 35, the main portion 1252 further includes a buckle rotation restriction projection 1262 extending therefrom. The projection 1262 is configured to engage the buckle rotation restriction groove 1284 in the posterior shell wing 1278 (FIG. 36) in the manner previously discussed to prevent rotational movement of the straps. In this manner, a user can easily manipulate the straps and buckle assemblies 1250, which stay in position while a user attempts manipulation.

Returning to FIG. 34, the clamping portion 1266 includes an actuation portion or tab 1268 that can be manipulated by a user to clamp and unclamp the clamping portion 1266 via selective rotation about the first hinge 1264.

As further shown in FIGS. 34 and 35, an engaging portion or snap locking projection 1270 is formed on the clamping portion 1266 to selectively engage the main portion 1252. In this manner, the clamping portion 1266 can be clamped and unclamped from the main portion 1252 to provide quick tightening and loosening of straps once the straps have been initially tightened.

The strap retaining portion 1274 includes a receiving loop or D-ring 1276 to receive a looped end of a strap therethrough. Clamping or unclamping of the clamping portion 1266 is transmitted through the strap retaining portion 1274 via relative rotation at the second hinge 1272. Thus, Clamping or unclamping of the clamping portion 1266 is also transmitted to the strap connected to the strap retaining portion 1274.

As discussed above, the straps need only to be tightened once initially (or infrequently to accommodate swelling or reduction of swelling of tissues) and the buckle assemblies 1250 can be utilized to provide quick connecting and tightening or loosening of the straps. When a user begins the donning process, the straps are initially loosened and the buckle assemblies 1250 are removed from the walker to allow the dorsal shell of the walker to be rotated away from the posterior shell. Thus, an opening between the dorsal and posterior shells allows a wearer to position their lower limb within the walker. As discussed above, the dorsal shell will tend to close when the opening force is removed.

Once the dorsal shell has closed over the posterior shell, the buckle assemblies 1250 are attached to the eyelets and seated in the posterior shell in the unclamped configuration. The clamping portions 1266 are then clamped and the straps are initially tightened to provide the appropriate amount of support and stabilization to the lower leg.

When the user begins the doffing process, the clamping portions 1266 are unclamped, and the buckle assemblies 1250 are removed from the seats and eyelets of the posterior shell. Then, the user can pivot the dorsal shell away from the posterior shell to remove the lower leg from the walker.

To repeat the donning process, the user need only insert the lower leg within the walker, attach the buckle assemblies 1250 to the posterior shell, and clamp the clamping portions 1266. Thus, there is no need to adjust the strap tension each time the user dons the walker. Accordingly, a more convenient and easy to use configuration is provided to assist users that may have trouble manipulating numerous straps every time they need to don and doff the walker.

The configurations of the protruding portion 1256, head portion 1258, reduced size portion 1260, strap retaining portion 1274, and buckle rotation restriction projection 1262 of the buckle assembly 1250 can also be utilized in the strap retaining assembly 1144 discussed above to selectively connect the strap retaining assembly 1144 to the posterior shell wing 1278. In this manner, the buckle assemblies 1250 and the strap retaining assemblies 1144 are interchangeable from one side of the walker to the other. Accordingly, the straps and buckle assemblies 1250 can be easily oriented for manipulation by right or left handed users. Additionally, the straps can be completely removed from the walker for any desired reason, such as replacement of components, or for storage.

Figure 37:
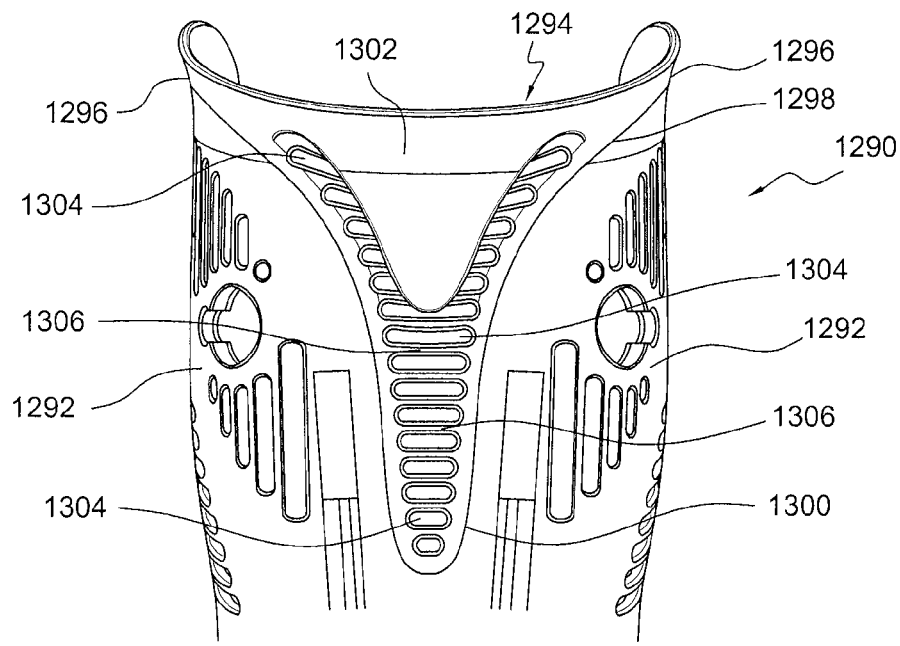
FIG. 37 is a partial rear view of a variation of a posterior shell and expansion mechanism for use with a hinged circumferential walker in accordance with the present disclosure.
Figure 38:
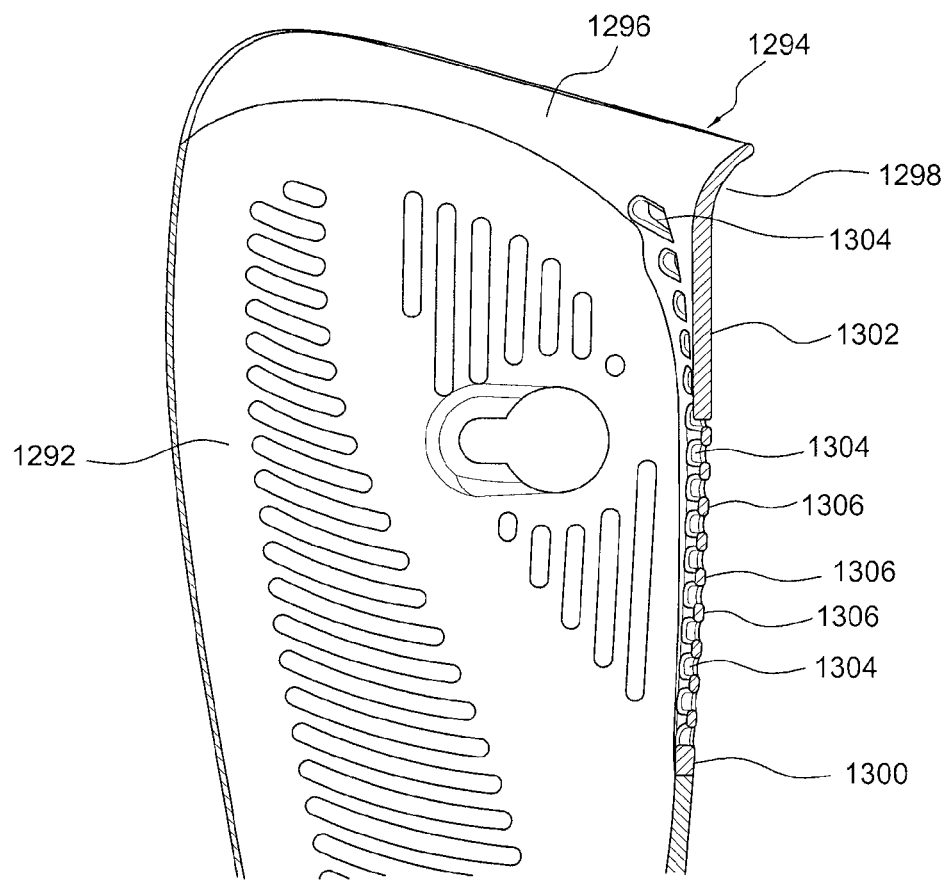
FIG. 38 is a partial cross-sectional view of the posterior shell of FIG. 37.

Further variations of components for use with a hinged circumferential walker are discussed next G. Variations of Components for Use with a Hinged Circumferential Walker A variation of an expansion joint 1294 for use with a circumferential walker is shown in FIGS. 37 and 38.

A posterior shell 1290 generally constructed in accordance with the principles discussed above is shown in FIG. 38. The posterior shell 1290 includes medial and lateral wing portions 1292 that define an opening therebetween in the proximal section of the posterior portion of the posterior shell 1290. An expansion joint 1294 generally of the type described above is situated in the opening between the wing portions 1292. The wing portions 1292 include proximal edges that carry flexible or resilient expansion joint edges 1296 to accommodate various sized anatomies, or swelling, and/or to reduce or eliminate pressure points, in a manner previously discussed.

The expansion joint 1294 includes a proximal portion 1298, a distal portion 1300, and a reinforcing portion 1302 located in the proximal portion 1298. The expansion joint 1294 has a larger dimension in the proximal portion 1298 and tapers to a smaller dimension in the distal portion 1300, in a manner discussed above. The reinforcing portion 1302 has a similarly configured tapering shape from the proximal portion to the distal portion.

Similarly to the expansion joints discussed above, the expansion joint 1294 also includes expansion holes or openings 1304 arranged horizontally, or with a slight angled orientation in the proximal-distal direction. The expansion holes or openings 1304 extend in the proximal-distal direction between the edges of the expansion joint 1394 and between the reinforcing portion 1302 and the edges of the expansion joint 1394. The expansion holes or openings 1304 function as described above. Expansion struts 1306 are defined between the expansion openings 1304.

As can be seen in FIG. 38, the expansion struts 1306 have a smaller thickness than the remaining portions of the expansion joint 1294, such as the reinforcing portion 1302. In this manner, the expansion struts 1306 can more easily expand (in a manner similar to a rubber band) to accommodate various sized anatomies (for example, a larger calf size), or swelling, and/or to reduce or eliminate pressure points, in a manner previously discussed.

Figure 39:
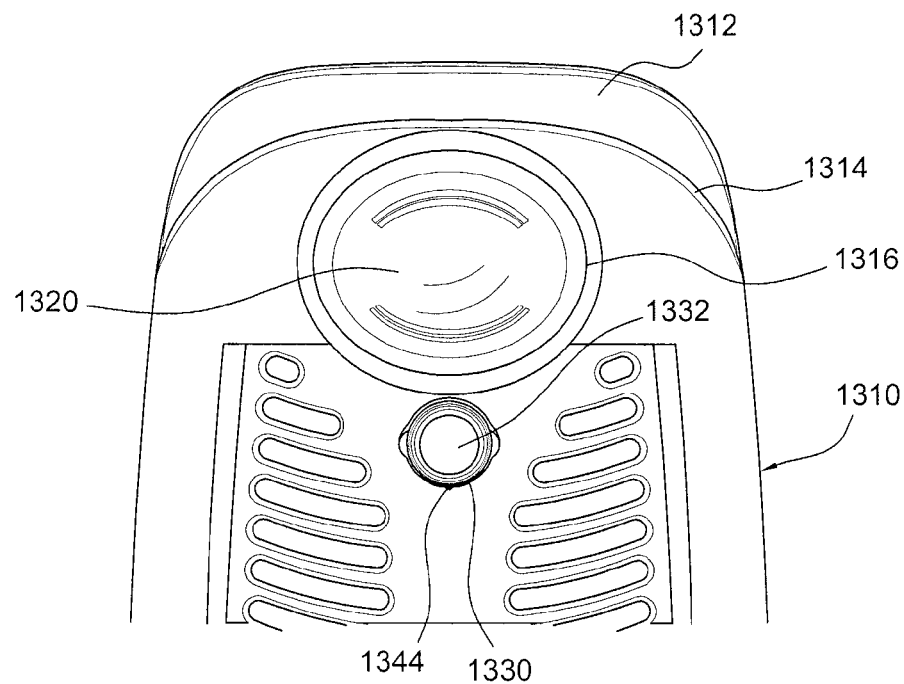
FIG. 39 is a partial front view of a variation of a dorsal shell, pump assembly, and valve assembly for use with a hinged circumferential walker in accordance with the present disclosure.
Figure 40:
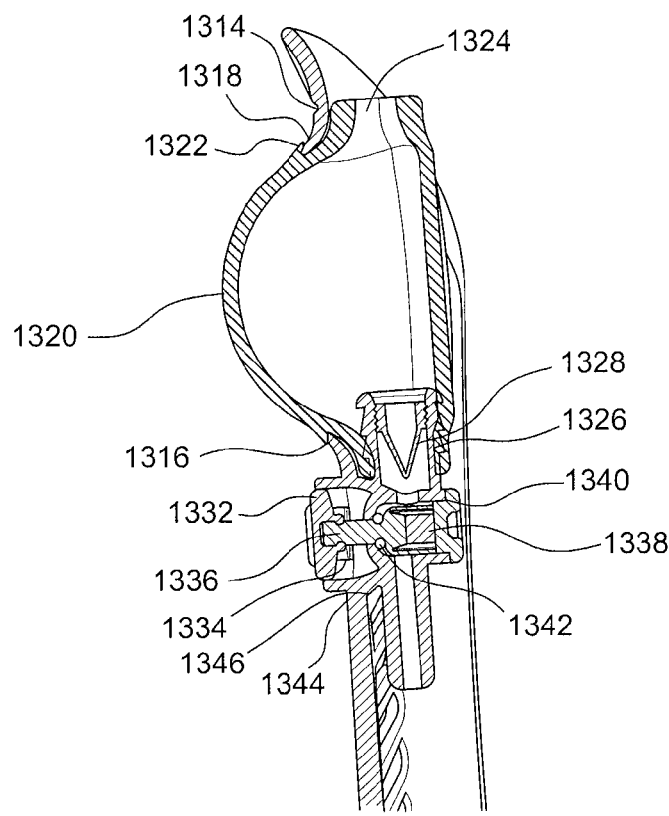
FIG. 40 is a partial cross-sectional view of the dorsal shell of FIG. 39.

A further variation of a dorsal shell 1310 for use with a circumferential walker is shown in FIGS. 39 and 40.

The dorsal shell 1310 generally constructed in accordance with the principles discussed above is shown FIG. 39. The dorsal shell 1310 includes a proximal edge portion 1312 that is shaped to engage the shin of a wearer. In order to accommodate different sized anatomies and/or to reduce or eliminate pressure points, a living hinge 1314 is provided along the proximal edge portion 1312 to allow the proximal edge portion 1312 to flex or bend about the living hinge 1314.

As shown in FIG. 40, the living hinge 1314 is a thin section of material between the proximal edge portion 1312 and the main section of the dorsal shell 1310. The living hinge 1314 has a thickness that is less than the thickness of the rest of the dorsal shell 1310 or the proximal edge portion 1312. Since the living hinge 1314 has a smaller thickness than the dorsal shell 1310 or the proximal edge portion 1312 the proximal edge portion 1312 is able to bend or flex with respect to the dorsal shell 1310 around the living hinge 1314.

The specific construction of the living hinge 1314 is dependent upon the desired amount of flexing, and the direction of flexing. The actual thickness and shape of the living hinge 1314 is dependent upon the thickness of the dorsal shell 1310 and the proximal edge portion 1312. The living hinge 1314 may therefore be formed in any suitable shape, size and orientation, in order to provide the desired flexing characteristics.

For example, the living hinge 1314 may be provided by a recessed line or groove along the anterior surface of the proximal portion of the dorsal shell 1310. The length of the living hinge 1314 may extend substantially along the entire proximal edge portion 1312. Alternatively, the length of the living hinge 1314 may have any suitable length. The actual process of forming the living hinge 1314 will be understood by a skilled artisan.

The dorsal shell 1310 also includes a pump receiving opening 1316. The pump receiving opening 1316 includes a tapered ridge 1318 extending around the periphery of the opening 1316.

As shown in FIG. 40, a flexible bulb type pump 1320 is inserted through the pump receiving opening 1316. The pump 1320 includes a flexible lip 1322 extending around the periphery of the pump 1320 for cooperative engagement with the tapered ridge 1318 to retain the pump 1320 with the pump receiving opening 1316 of the dorsal shell 1310.

The pump 1320 includes an inlet 1324 that allows air to flow into the body of the pump 1320, but is selectively closed when the pump is actuated so that air does not flow out of the pump 1320 through the inlet. The pump 1320 also includes an outlet 1326, opposed to the inlet 1324, and retaining a one-way outlet valve 1326 therein, such that actuation of the pump causes air to flow from the inlet 1324 through the one-way outlet valve 1326 towards the bladders (not shown but described in detail above).

A push button release valve 1330 is incorporated with the pump 1320 to release the pressure within the bladders. An actuation surface 1332 of the release valve 1330 is connected to a valve stem 1336 and is biased toward the unactuated position via a biasing element or spring 1334.

The valve stem 1336 passes through a valve seat 1340 and carries a sealing element 1342 thereon for selective engagement with the valve seat 1340 to open and close the valve 1330. The valve stem 1336 is engaged with a guide post 1338 to guide the reciprocating action of the valve stem 1336 within the valve 1330.

The valve 1330 passes through an opening 1344 in the dorsal shell 1310 to be carried thereon. The opening 1344 includes an anti-rotation cutout 1346 which engages an anti-rotation ridge or projection formed on the body of the valve 1330 to prevent rotation of the valve 1330 within the opening 1344.

While a specific configuration of a pump 1320 and release valve 1330 is described, it will be recognized that any suitable pump and valve arrangement may be utilized.

Figure 41:
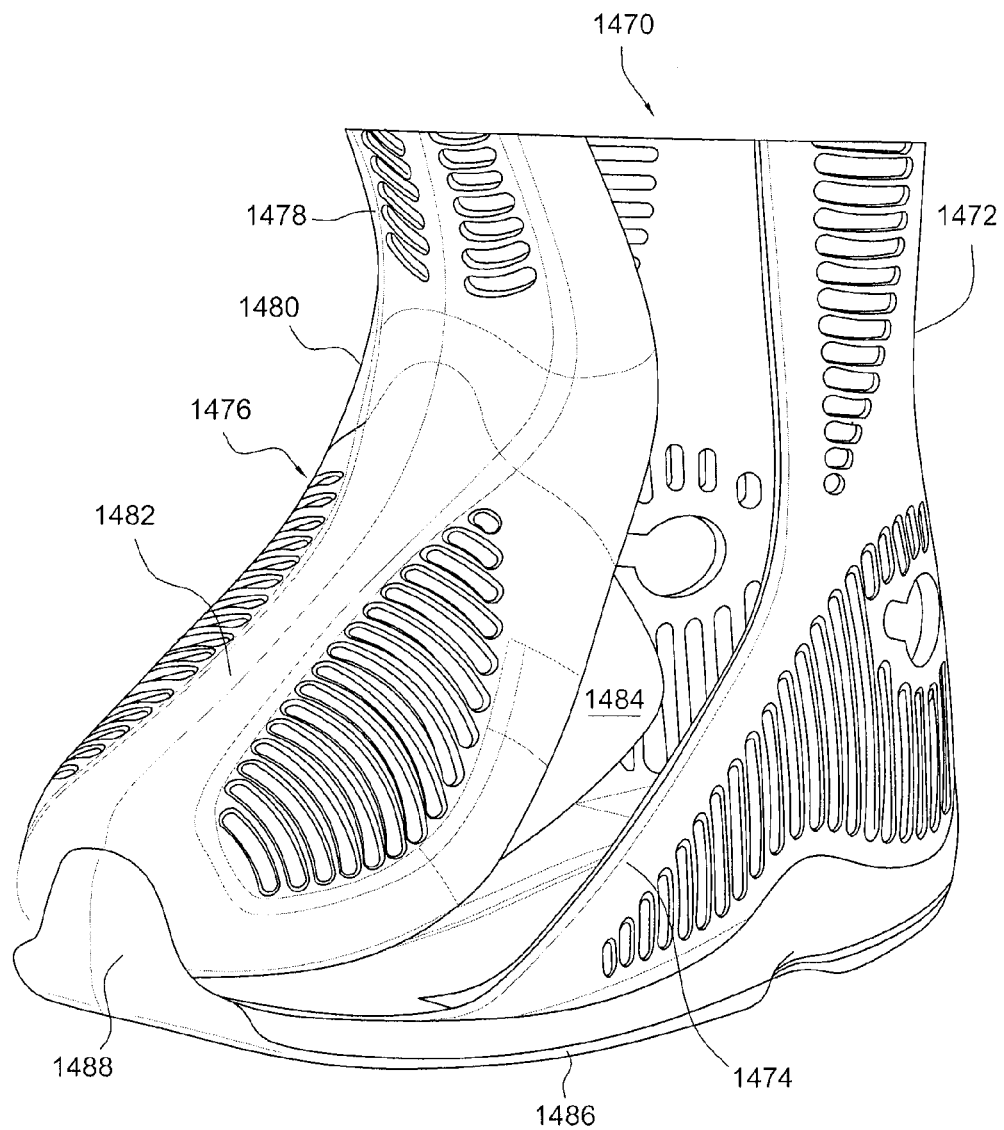
FIG. 41 is a partial perspective view of another variation of a dorsal shell for use with a hinged circumferential walker in accordance with the present disclosure.

A further variation of a dorsal shell 1476 for use with a circumferential walker 1470 is shown in FIG. 41.

The walker 1470 shown in FIG. 41 includes a posterior shell 1472 having lateral and medial side portions 1474 and a dorsal shell 1476. The dorsal shell has proximal 1478 and distal 1482 portions connected to each other via a flexible or hinge portion 1480. The distal shell portion 1482 is connected at an anterior portion thereof to an outsole 1486 (or a planter shell portion) via a hinge 1488 of any type described herein.

The distal dorsal shell portion 1482 also includes lateral and medial flap portions 1484 extending distally therefrom. The flap portions 1484 provide mechanisms to align the dorsal shell 1476 with the posterior shell 1472 during opening and closing of the walker 1470 about the hinge 1488. The flap portions 1484 also aid to retain the distal dorsal shell portion 1482 with the plantar shell of the posterior shell 1472.

Next, variations of hinge configurations for use in a hinged circumferential walker are discussed.

H. Variations of Hinge Configurations for use With a Hinged Circumferential Walker Additional variations of hinge configurations for use with a hinged circumferential walker are shown in FIGS. 42-50.

Figure 42:
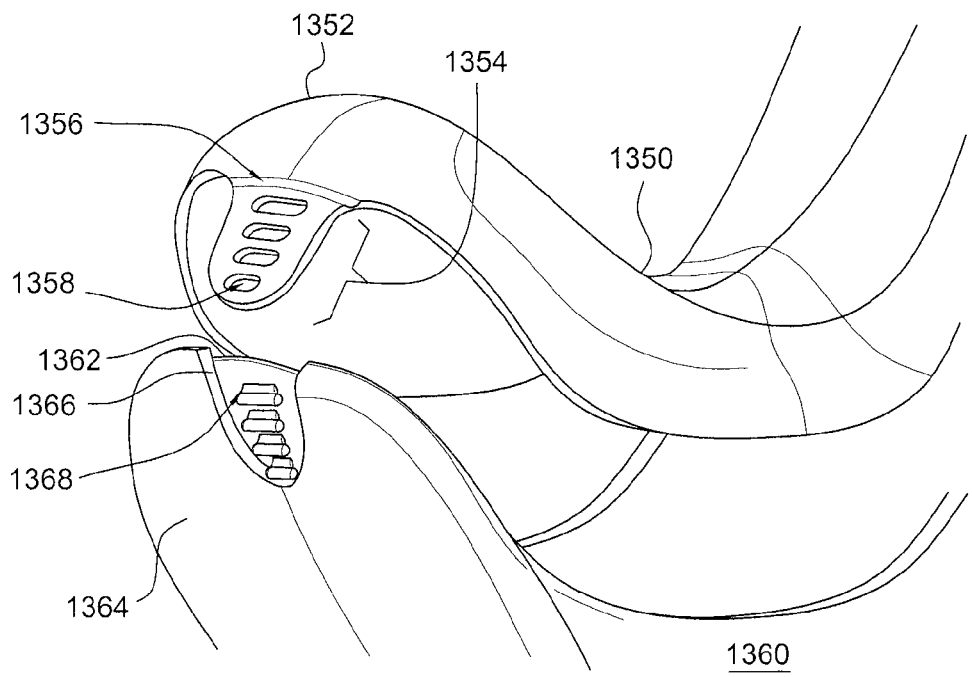
FIG. 42 is a partial perspective view of a variation of a hinge for use with a hinged circumferential walker in accordance with the present disclosure.

In a first variation, shown in FIG. 42, a dorsal shell 1350 includes a toe cover portion 1352 and an extension portion 1354 extending therefrom. A living hinge 1356, as described above, is formed between the extension portion 1354 and the dorsal shell 1350 to allow the extension portion 1354 to flex or bend with respect to the dorsal shell 1350. The extension portion 1354 also includes receiving openings 1358 to selectively engage, in a manner previously discussed, flexible protrusions 1368 positioned on either a plantar shell portion 1362 of a posterior shell 1360 or in a cutout 1366 in an outsole 1364. If the flexible protrusions 1368 are positioned on the plantar shell portion 1362, the cutout 1366 of the outsole 1364 can create a receiving space for the extension portion 1354 to be received therein to maintain a low profile device. Alternatively, the flexible protrusions 1368 can be positioned and formed within the cutout 1366 of the outsole 1364 to create a receiving space for the extension portion 1354 to be received therein to maintain a low profile device.

Figure 43:
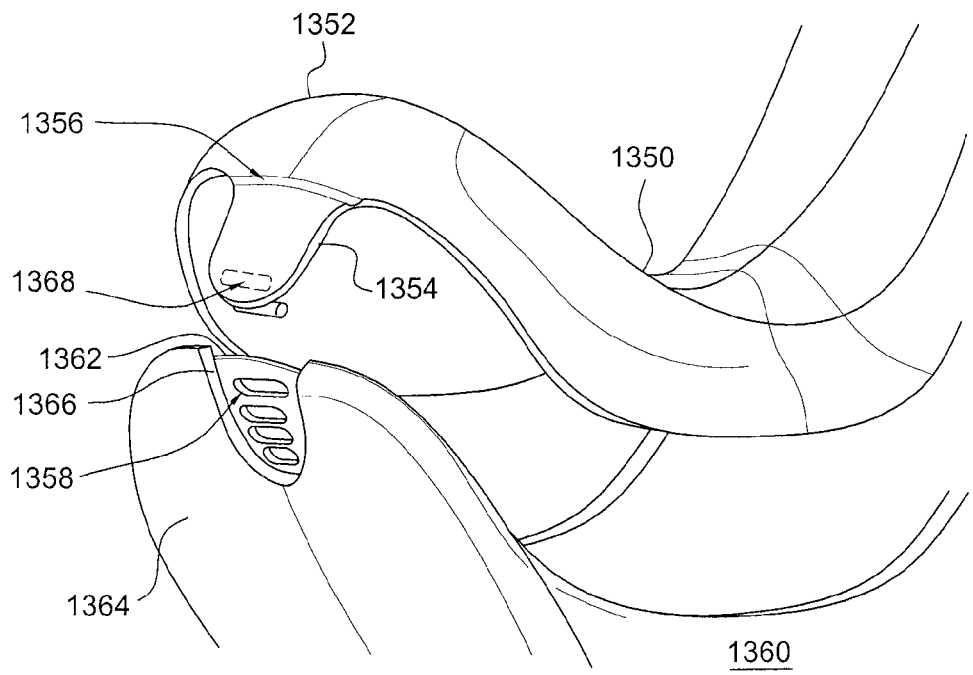
FIG. 43 is a partial perspective view of another variation of a hinge for use with a hinged circumferential walker in accordance with the present disclosure.

In the variation shown in FIG. 43, the location of the flexible protrusions 1368 and receiving openings 1358 is alternated from that shown in FIG. 42, such that the flexible protrusions 1368 are formed on the extension portion 1354 and the receiving openings 1358 are formed in the cutout 1366.

In each case, the living hinge 1356 of the extension portion 1354 allows the dorsal shell 1350 to rotate with respect to the posterior shell 1360 so that the circumferential walker can be opened to allow the wearer to place their lower leg therein. As discussed above, the flexible protrusions 1368 and receiving openings 1358 can be provided in the plurality to allow the wearer to adjust the spacing between the dorsal shell 1350 and the posterior shell 1360 in order to accommodate swelling or different size anatomies. While four protrusions and receiving openings are shown, it will be recognized that more or fewer protrusions and receiving openings can be utilized.

A further variation of a hinge configuration is shown in FIG. 44. As with previous variations, the walker includes a dorsal shell 1370 with a toe cover portion 1372. Receiving openings 1374 are positioned in the distal anterior portion of the toe cover portion 1372.

A posterior shell 1376 has a plantar shell portion 1378 with an extension portion 1380 extending from the anterior portion thereof and an outsole 1386 formed thereon. A living hinge 1382 is formed between the extension portion 1380 and the plantar shell portion 1378 to allow the extension portion 1380 to flex or bend about the plantar shell portion 1378. At least one flexible protrusion 1384 is formed on the extension portion 1380 to selectively engage at least one of the receiving openings 1374. Of course, it will be recognized that the position of the flexible protrusion 1384 and the receiving openings 1374 can be alternated.

As with previous variations, the engagement between the flexible protrusion 1384 and the receiving openings 1374 can be used to adjust the size of the walker. Additionally, the living hinge 1382 allows the dorsal shell 1370 to rotate about the planter shell portion 1378 to allow a user to easily don and doff the walker.

In a further variation shown in FIG. 45, the hinge can be formed by using fasteners. In particular, the dorsal shell 1390 includes a toe cover portion 1392 with a first connector portion 1394 formed at the anterior distal portion thereof.

The posterior shell 1396 includes an outsole 1398 formed thereon. The outsole 1398 includes an extension portion 1400 formed at the anterior portion thereof and carries a second connector portion 1402.

As shown in FIG. 45, the first connector portion 1394 is located on an exterior surface of the dorsal shell 1390 and the second connector portion 1402 is located on an interior surface of the extension 1400 of the outsole 1398. It will be recognized that these locations may be alternated.

The first and second connector portions 1394, 1402 are configured to allow selective and adjustable connection therebetween. Exemplary configurations can include hook and loop fastening material, or a plurality of snap connections. It will be recognized that either the first or second connector portions 1394, 1402 can be formed from hook material and the other formed from loop material, and vice versa. The hook and loop material can be attached to the dorsal shell 1390 and extension 1400 of the outsole 1398 via adhesive or other suitable mechanism. Alternatively, the hook material and loop fabric can be directly injection molded with or into the respective dorsal shell 1390 and extension 1400 of the outsole 1398. Exemplary methods of molding hook material into a shell are described in detail in U.S. Pat. No. 5,368,549, granted Nov. 29, 1994, U.S. Pat. No. 5,656,226, granted Aug. 12, 1997, and U.S. Pat. No. RE37,338, granted Aug. 21, 2001, each incorporated herein in the entirety by reference.

As will be understood, the first and second connector portions 1394, 1402 can be disengaged and engaged to alter the distance between the dorsal shell 1390 and the posterior shell 1396 to accommodate swelling or different size anatomies. Further, when the first and second connector portions 1394, 1402 are engaged, the dorsal shell 1390 can rotate with respect to the posterior shell 1396 to allow a wearer to easily don and doff the device.

A further variation of a hinge arrangement is shown in FIG. 46. In this configuration a dorsal shell 1410 includes a first strap receiving slot or D-ring 1416 at an anterior distal portion thereof.

A posterior shell 1412 includes an outsole 1414 formed thereon that has a second strap receiving slot or D-ring 1418 at an anterior portion thereof. A strap 1420 has one end looped over and secured to itself at the first strap receiving slot 1416. The strap is subsequently threaded through the second strap receiving slot 1418 and threaded up along and through a strap guide 1422 on the proximal surface of the dorsal shell 1410. The strap has a first connector portion 1424 at the end thereof for selective engagement with a second connector portion 1426 on the proximal surface of the dorsal shell 1410.

The first and second connector portions 1424, 1426 can be formed as discussed above from hook and loop fasteners to allow selective engagement therebetween and adjustment of the spacing between the dorsal shell 1410 and the posterior shell 1412 to accommodate swelling or different size anatomies. Further, due to the flexibility of the strap, the dorsal shell 1410 can rotate with respect to the posterior shell 1412 to allow a wearer to easily don and doff the device.

Although not shown, the strap can be secured at a first end to the outsole, threaded through the D-ring on the dorsal shell, and secured to a bottom surface of the outsole. A cutout on the outsole, similar to the cutout described above, can be provided to allow the strap to be secured therein to provide a low profile sole.

Figure 47:
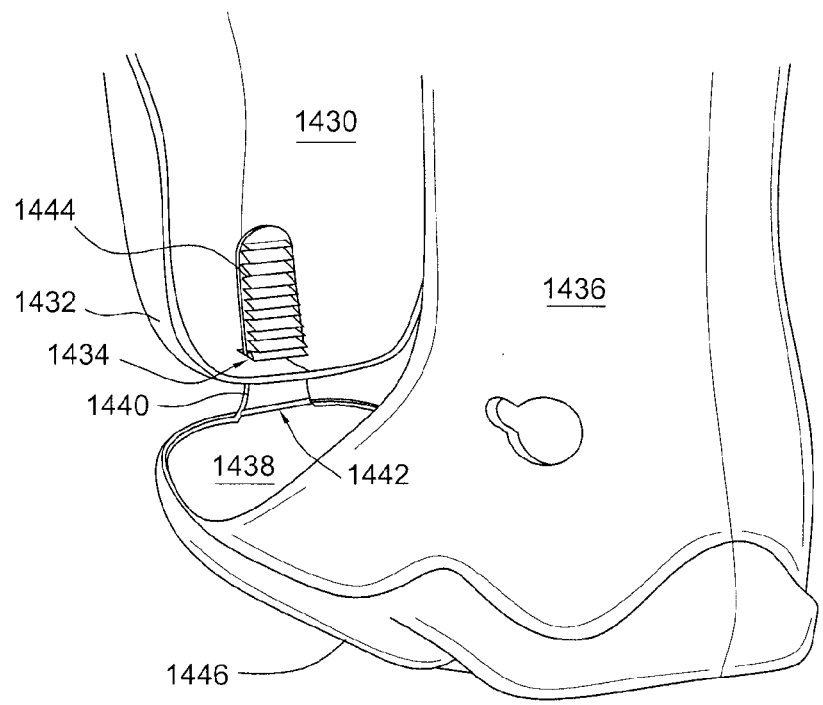
FIG. 47 is a partial perspective view of another variation of a hinge for use with a hinged circumferential walker in accordance with the present disclosure.
Figure 48:
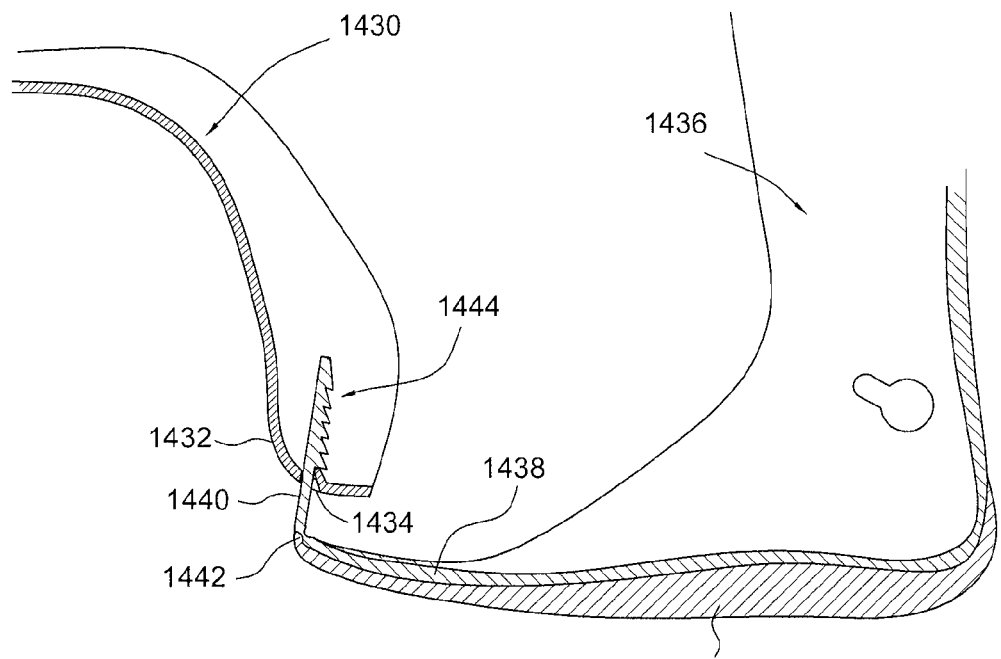
FIG. 48 is a partial cross-sectional view of the arrangement shown in FIG. 47.

A further variation of a hinge configuration is shown in FIGS. 47 and 48. A dorsal shell 1430 includes a toe cover portion 1432 that has as receiving opening 1434 formed at the anterior distal portion thereof.

A posterior shell 1436 includes a plantar shell portion 1438 and an outsole 1446 formed thereon. An extension portion 1440 extends from the plantar shell portion 1438 at an anterior portion thereof. A living hinge 1442 is formed between the extension portion 1440 and the plantar shell portion 1438 in a manner discussed above. Alternatively, the extension portion 1440 can be formed as a separate piece that is attached to the plantar shell portion 1438 in any suitable manner.

The extension portion 1440 includes a ratchet structure 1444 formed on one surface thereof. The extension portion 1440 is arranged to be received through the receiving opening 1434 to connect the dorsal shell 1430 to the posterior shell 1436 so that the dorsal shell 1430 can rotate with respect to the posterior shell 1436 to allow a wearer to easily don and doff the device.

When the dorsal shell 1430 is rotated to an open position with respect to the posterior shell 1436, the ratchet structure 1444 can easily slide within the receiving opening 1434 to adjust the spacing between the dorsal shell 1430 and the posterior shell 1436.

When the dorsal shell 1430 is rotated to a closed position, the extension portion 1440 flexes or bends about the living hinge 1442 and the ratchet structure 1444 engages the edge of the receiving opening 1434 to maintain the dorsal shell 1430 in engagement with the posterior shell 1436.

Figure 49:
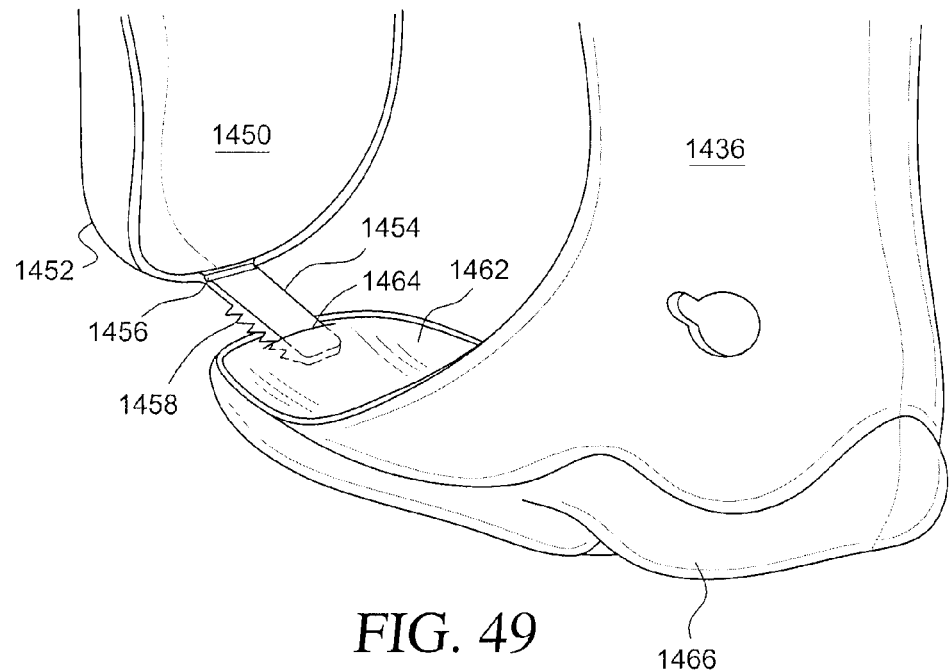
FIG. 49 is a partial perspective view of another variation of a hinge for use with a hinged circumferential walker in accordance with the present disclosure.
Figure 50:
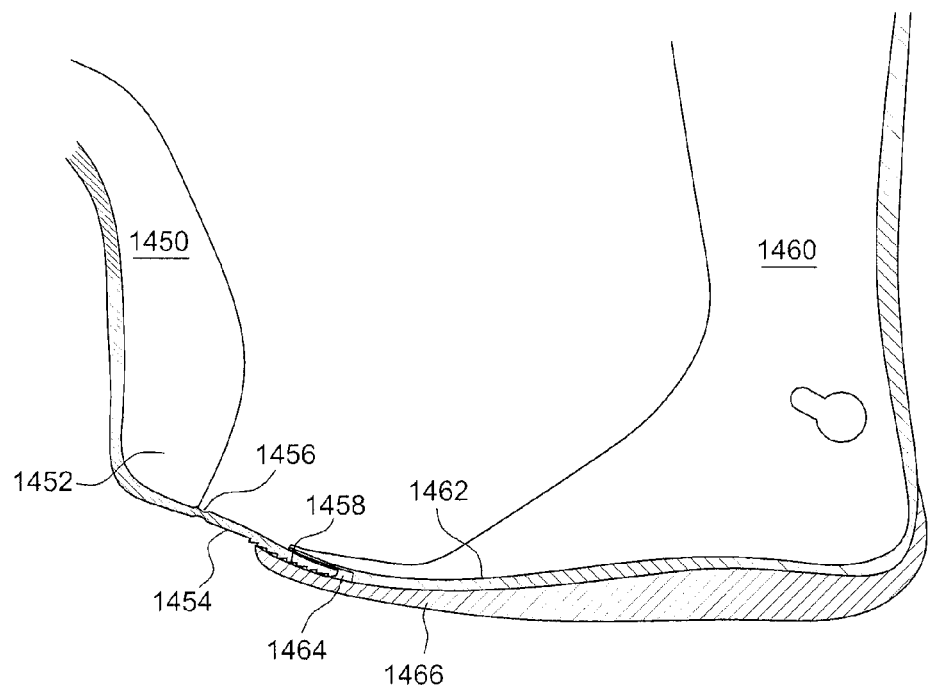
FIG. 50 is a partial cross-sectional view of the arrangement shown in FIG. 49.

In a similar configuration shown in FIGS. 49 and 50, the dorsal shell 1450 includes a toe cover portion 1452 and an extension portion 1454 extending from an anterior distal portion thereof. A living hinge 1456 is formed between the toe cover portion 1452 and an extension portion 1454 to allow the extension portion 1454 to flex or bend about the toe cover portion 1452. A ratchet structure 1458 is formed on a surface of the extension portion 1454. It will be recognized that the extension portion 1454 can be formed as a separate piece that is connected to the dorsal shell 1450 in any suitable manner.

A posterior shell 1460 has a plantar shell portion 1462 having an outsole 1466 formed thereon. A receiving opening 1464 is formed at an anterior portion between the plantar shell portion 1462 and the outsole 1466. The extension portion 1454 is configured to extend into the receiving opening 1464, and functions in a manner previously discussed to allow adjustment of the spacing between the dorsal shell 1450 and the posterior shell 1460 to accommodate swelling and different size anatomies.

Figure 51:
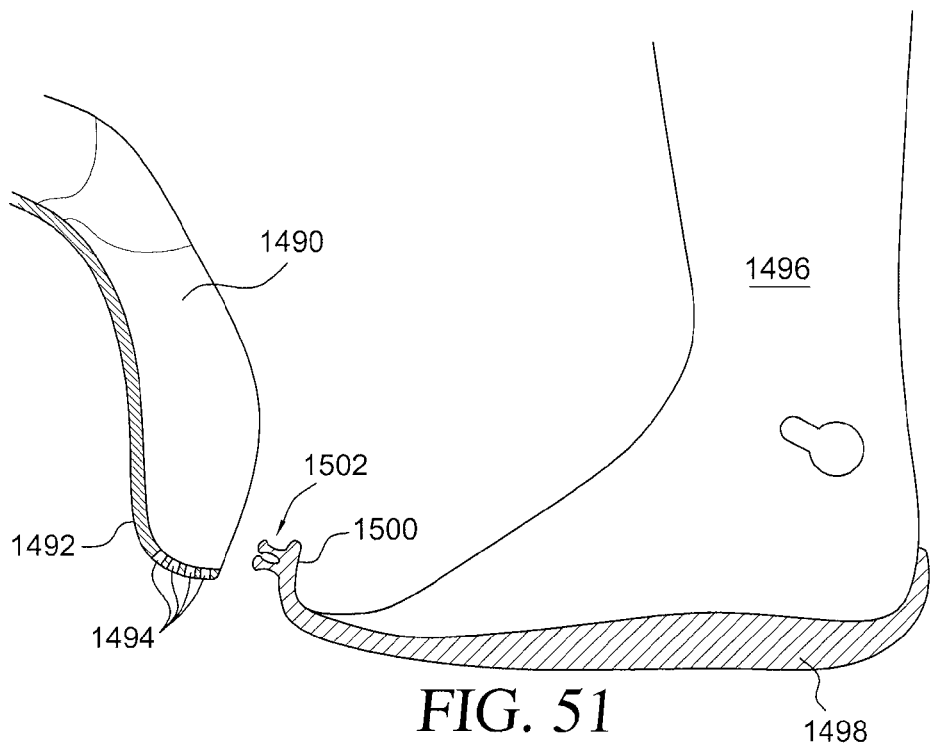
FIG. 51 is a partial cross-sectional side view of another variation of a hinge for use with a hinged circumferential walker in accordance with the present disclosure.

Another variation of a hinge for use with a hinged circumferential walker is shown in FIG. 51. The dorsal shell 1490 includes a toe cover portion 1492 that has receiving openings 1494 formed therein.

The posterior shell 1496 has an outsole 1498 formed thereon or attached thereto. The outsole 1498 includes an extension portion 1500 extending from an anterior portion thereof. Projections 1502 extend from the anterior surface of the extension portion 1500 for selective engagement with the receiving openings 1494 of the dorsal shell 1490.

This configuration prevents accidental disengagement of the projections 1502 from the receiving openings 1494 due to the forward migration of the wearer's foot within the walker during the gait cycle. Since the projections 1502 are formed on the anterior surface of the extension portion 1500, even if the wearer's foot migrates all the way to the anterior portion of the walker, the foot will not cause the projections 1502 to accidentally disengage from the receiving openings 1494.

Figure 52:
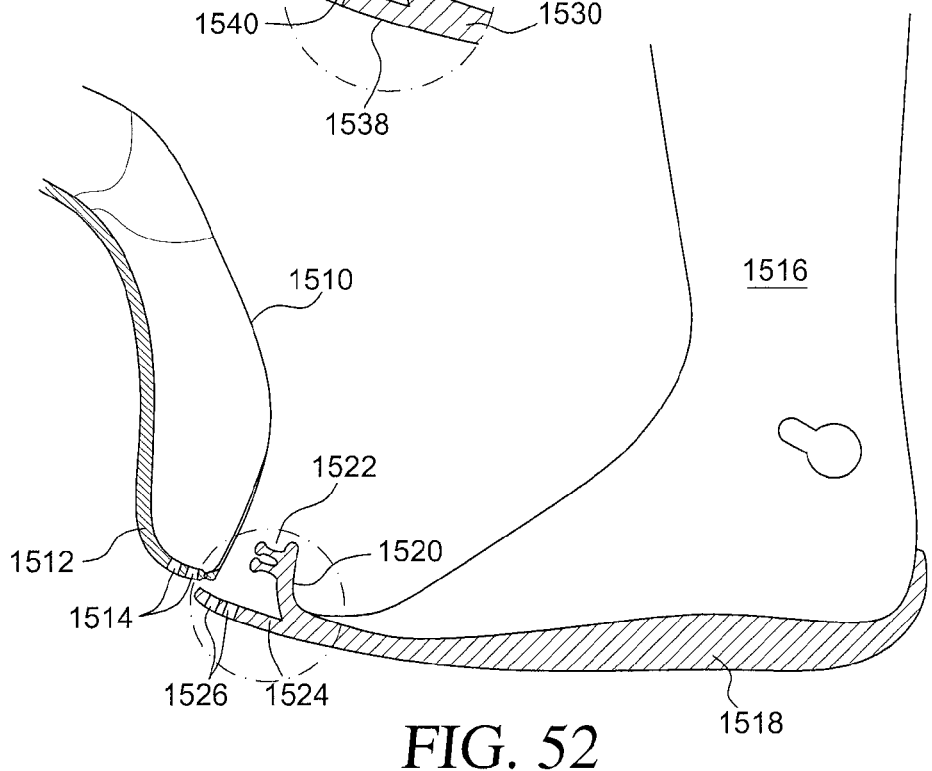
FIG. 52 is a partial cross-sectional side view of another variation of a hinge for use with a hinged circumferential walker in accordance with the present disclosure.

Another variation of a hinge for use with a hinged circumferential walker is shown in FIG. 52. The dorsal shell 1510 includes a toe cover portion 1512 that has receiving openings 1514 formed therein.

The posterior shell 1516 has an outsole (or plantar shell portion) 1518 formed thereon or attached thereto. The outsole 1518 includes first and second extension portions 1520, 1524 extending from an anterior portion thereof.

Projections 1522 extend from the anterior surface of the first extension portion 1520 for selective engagement with the receiving openings 1514 of the dorsal shell 1490 and with receiving openings 1526 formed in the second extension portion 1524.

This configuration provides additional assurance that the projections 1522 will not accidentally disengage from the receiving openings 1514 in the dorsal shell 1510, by providing the second extension portion 1524 covering the receiving openings 1514.

Figure 53:
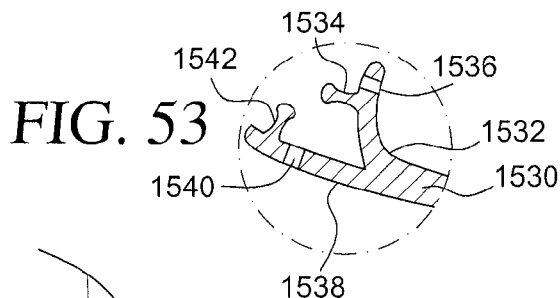
FIG. 53 is an expanded partial cross-sectional side view of a variation of the hinge shown in FIG. 52.

In an alternate configuration of the hinge shown in FIG. 52, the hinge shown in FIG. 53 includes an outsole (or plantar shell portion) 1530 having first and second extension portions 1532, 1538 extending from an anterior portion thereof. Each of the first and second extension portions 1532, 1538 includes at least one projection 1534, 1542 extending therefrom and at least one receiving opening 1536, 1540 formed therein. The projections 1534, 1542 are respectively formed on the anterior and posterior surfaces of the first and second extension portions 1532, 1538.

The dorsal shell (not shown, see FIG. 52) includes a plurality of receiving openings. As will be understood, the receiving openings of the dorsal shell are sandwiched between the projections 1534, 1542 and receiving openings 1536, 1540 of the first and second extension portions 1532, 1538, such that the projections 1534, 1542 extend through the receiving openings in the dorsal shell to retain the dorsal shell in connection with the posterior shell.

This configuration provides yet another mechanism to ensure that the dorsal shell does not accidentally disengage from the posterior shell of the walker.

Various other hinge configurations that allow selective adjustment of the spacing between the dorsal shell and the posterior shell can be provided to accommodate swelling and different size anatomies.

I. Variation of a Circumferential Walker

As shown in FIGS. 54-63, a variation of a circumferential walker 2100 is configured in an essentially two-piece construction to provide a lightweight, sleek, and low profile device for use in stabilizing, immobilizing, and supporting the lower leg. Numerous advantages are obtained from such a configuration, as discussed above.

The walker 2100 includes a semi-rigid, or substantially rigid shell configuration as previously described. The walker 2100 includes a posterior shell 2120 that extends from a posterior side of the lower leg and ankle, along the distal surface of the foot, and terminates in a plantar shell portion 2144 that extends along the plantar surface of the foot. The posterior shell 2120 includes lateral and medial (first and second) wing portions 2122 that extend partially around the lower leg, ankle, and foot from the posterior shell 2120 to wrap around the leg in order to at least partially enclose and support the lower leg. The posterior shell 2122 also defines side shell portions 2310, 2311 extending along the lateral and medial sides of the plantar shell portion 2144, and being spaced apart by the plantar shell portion 2144 so as to define a clearance 2312 between each of the side shell portions 2310, 2311. The posterior shell 2122 also defines a closed-ended heel portion 2314 and an open-ended toe portion 2316. The side shell portions 2310 terminate before the toe end 2316, leaving an open section 2320 at the toe end 2316. The plantar shell portion 2144 defines a bottom or outer surface 2318 that secures adjacently to the outsole 2148.

A dorsal shell 2102 is generally complementary shaped to the posterior shell 2120 to at least partially surround or enclose the lower leg, ankle, and foot to provide protection, support, and stabilization thereto. The walker 2100 can thus be formed in a general configuration to fully encase and protect the lower leg, ankle, and foot.

Figure 54:
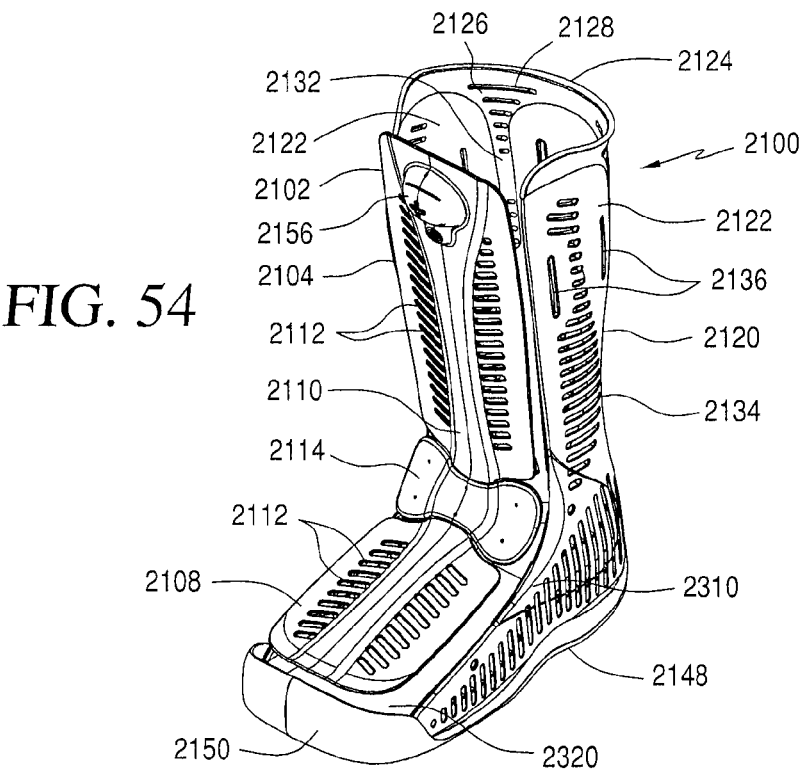
FIG. 54 is a perspective view of another embodiment of a circumferential walker in accordance with the present disclosure.
Figure 55:
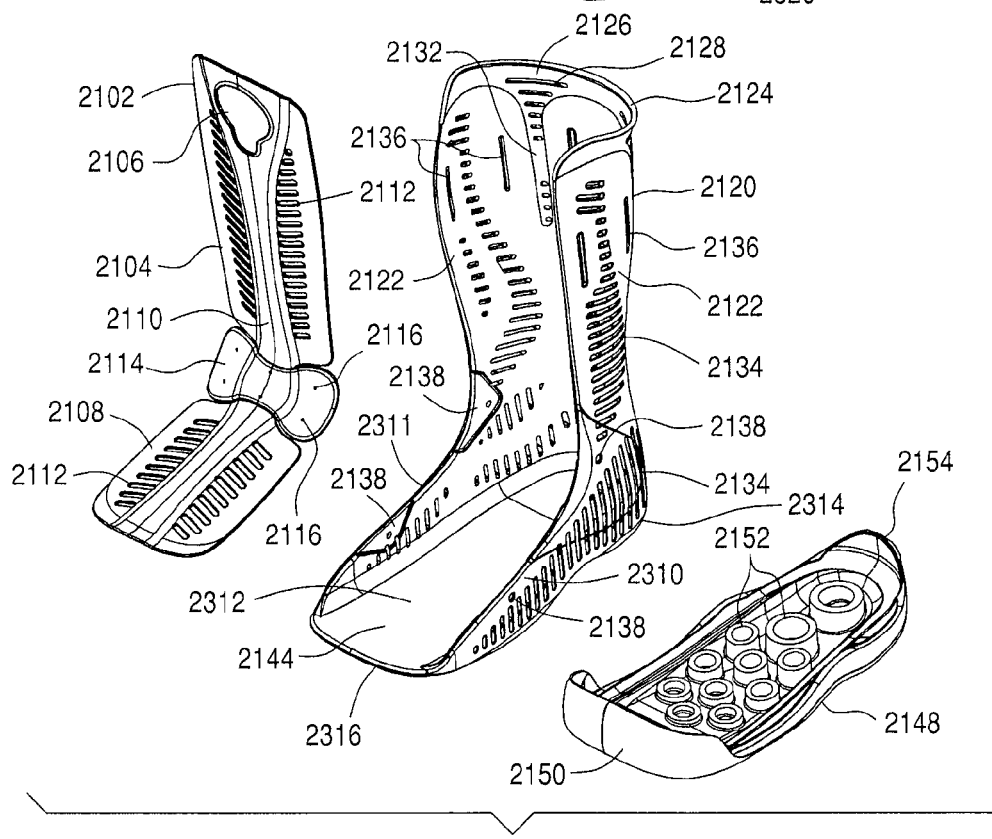
FIG. 55 is an expanded view of the components of the circumferential walker shown in FIG. 54.
Figure 60:
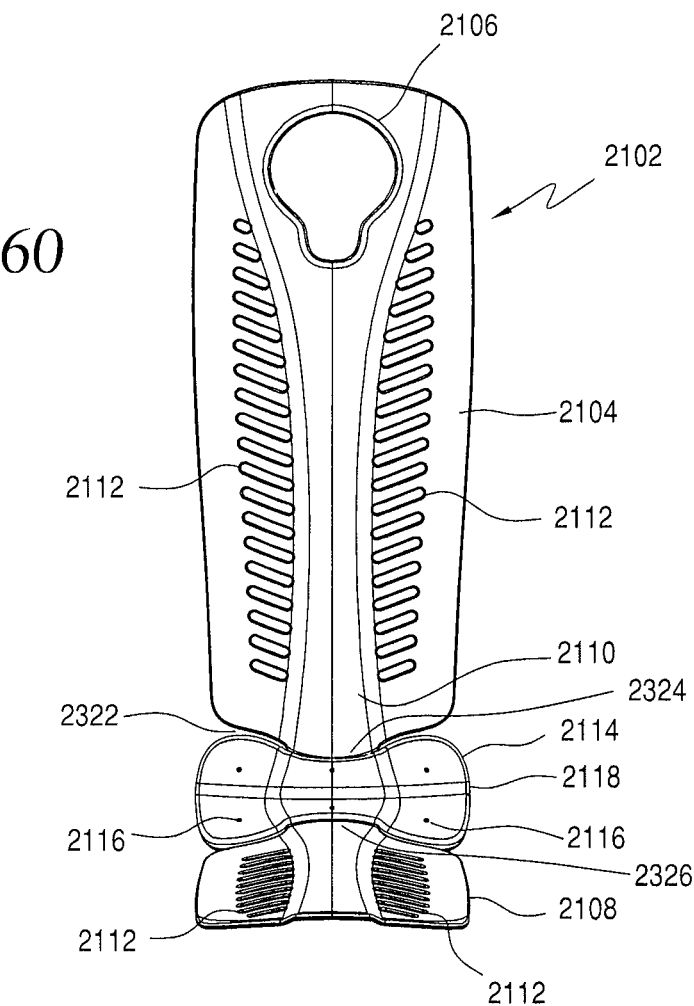
FIG. 60 is a rear view of the dorsal shell component of the circumferential walker shown in FIG. 54.

As best seen in FIGS. 54, 55, and 60, the dorsal shell 2102 is formed either in a single piece or in multiple shell portions. The dorsal shell can include a raised reinforcing ridge 2110 running along the proximal surface thereof and may also include clearance holes 2112 in accordance with the discussion above. The dorsal shell 2102 also includes a pump assembly receiving opening 2106 which can be configured in a similar manner as previously discussed, or may simply be provided as a clearance opening through the dorsal shell 2102. The position of the pump assembly receiving opening 2106 can be varied to accommodate numerous locations a pump assembly.

In the exemplary embodiment, the dorsal shell 2102 includes a proximal shell portion 2104 that is connected to a distal shell portion 2108 via a flexible or resilient portion or hinge connection 2114. The proximal and distal shell portions 2104, 2108 connect to the hinge connection 2114 at narrowed central portions 2324, 2326. A gap 2322 is at least formed between the proximal shell portion 2104 and the hinge connection 2114 outside of the narrowed central region 2324.

The connecting portion 2114 may be formed as a flexible or resilient material positioned between the proximal and distal shell portions 2104, 2108 and encompassing a connecting shell portion between the proximal and distal shell portions 2104, 2108. This connecting portion may be formed via overmolding a different material over the connecting shell portion to form a flexible or resilient expansion portion or mechanism, in a manner discussed above. The connecting portion 2114 can be positioned so as to be located between the anatomical portion of the wearer and a strap used to retain the walker 2100 thereon. In this manner, the possibility of pressure points being caused by such a strap is greatly reduced or eliminated.

The connecting portion 2114 can include holes 2216 passing therethrough, which may function as ventilation holes and/or which may increase the flexibility of the connecting portion 2114.

As best seen in FIG. 60, the connecting portion 2114 can include a gap 2118 formed along one surface thereof. The presence of the gap 2118 will help to reduce or eliminate the formation of a pressure point along the dorsal surface of a user's lower leg, ankle, or foot. Further, due to the flexible nature or resiliency of the connecting portion 2114, and the additional presence of the gap 2118, when the dorsal shell 2102 is closed around the user's lower leg, ankle, or foot, different sized anatomies can be accommodated using the same sized walker 2100. Additionally, the walker 2100 will automatically expand or contract due to swelling or reduction of swelling of the lower leg, ankle, and foot of a user. Of course, it will be recognized that the gap 2118 is not a required feature, and the connecting portion 2114 can accomplish the above functions without the use of such a gap.

Figure 57:
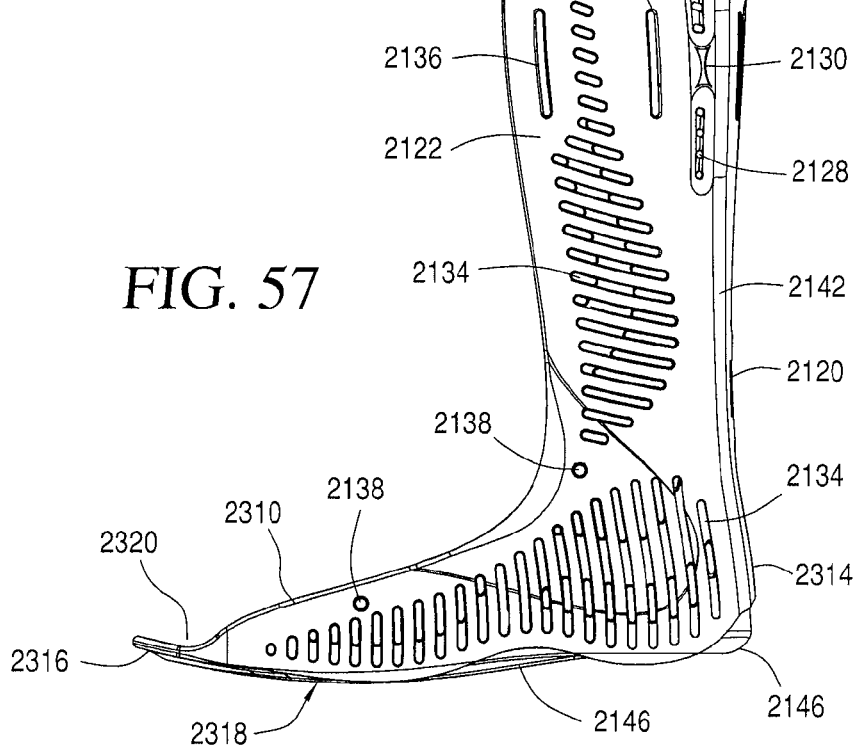
FIG. 57 is a side view of the posterior and plantar shell components of the circumferential walker shown in FIG. 54.
Figure 58:
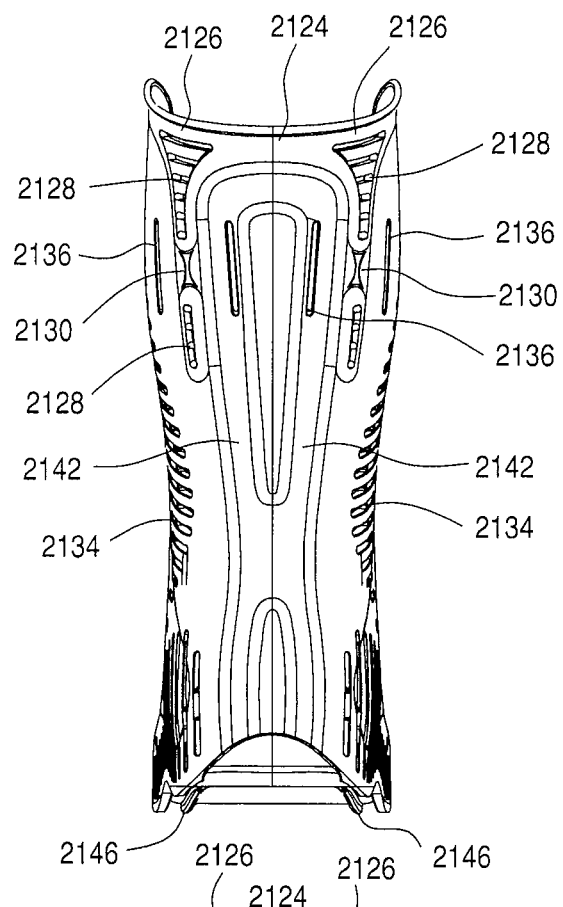
FIG. 58 is a rear view of the posterior and plantar shell components of the circumferential walker shown in FIG. 54.
Figure 59:
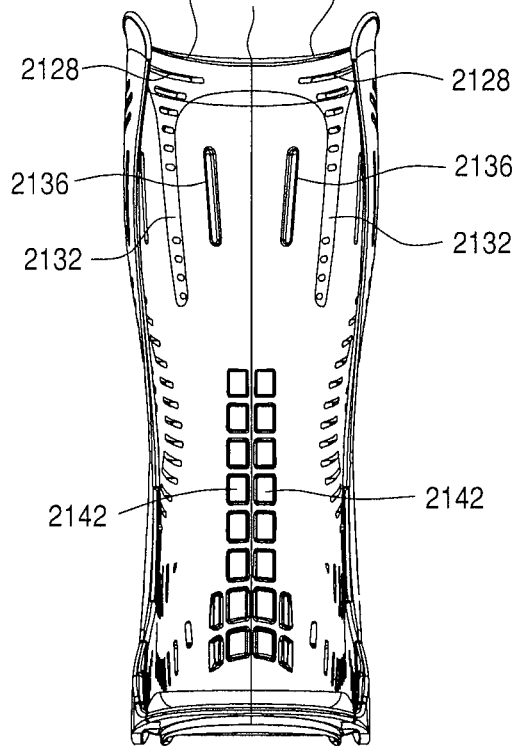
FIG. 59 is a front view of the posterior and plantar shell components of the circumferential walker shown in FIG. 54.

As best seen in FIGS. 54-59, the posterior shell 2120 has generally the same configuration as discussed above, including clearance holes 2134, and reinforcing or strengthening structures 2142. Such reinforcing or strengthening structures 2142 can extend over a portion of the height of the posterior shell 2120, as shown in FIG. 59, or over substantially the entire height of the posterior shell 2120. Also, as previously discussed, the posterior shell 2120 can include a flexible or compliant proximal edge 2124, which can be overmolded. A portion of the flexible or compliant edge 2124 can also be trimmed to accommodate users having shorter legs, in order to avoid the creation of pressure points from the edge being too large. This allows the user to adjust the fit of the walker 2100, without the creation of hard edges.

Figure 56:
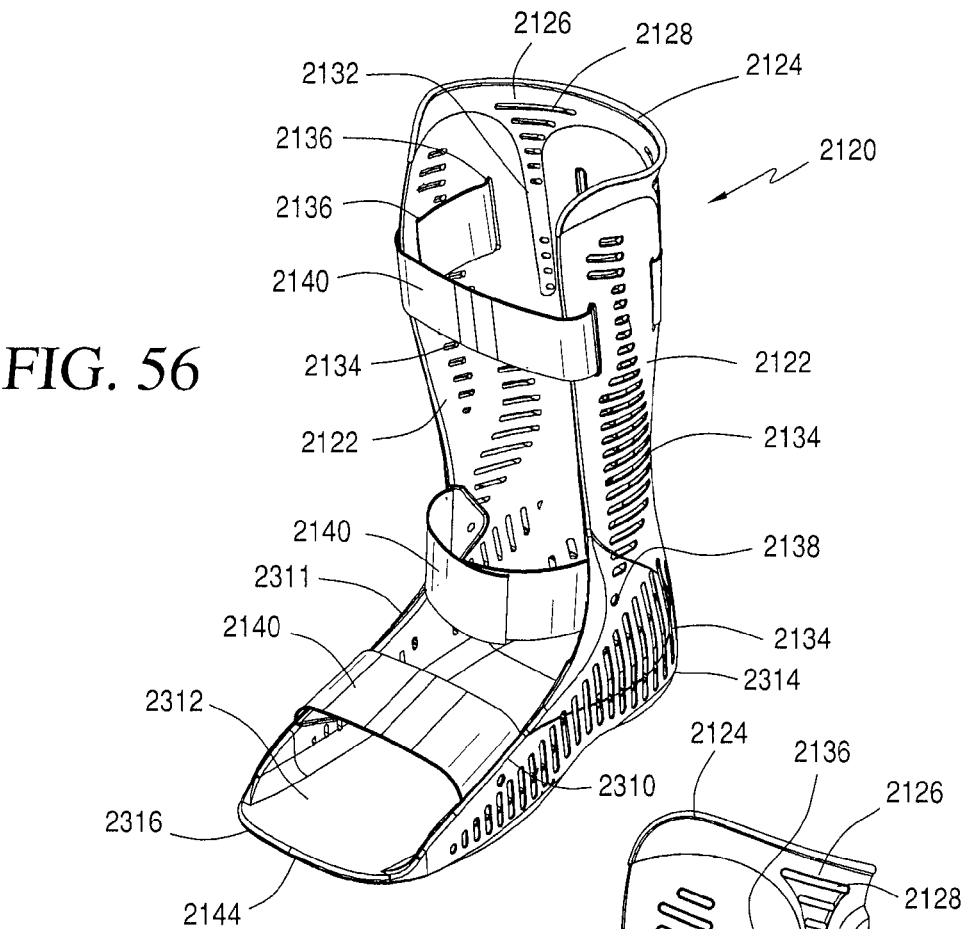
FIG. 56 is a perspective view showing a strapping configuration for use with the circumferential walker shown in FIG. 54.

As best seen in FIGS. 55, 56, and 59, strap slots 2136 are positioned in the proximal portion of the posterior shell 2120 for receiving a strap 2140 therein. The strap 2140 can include suitable connecting structures, for example corresponding hook and loop fasteners at respective ends thereof so that the ends of the strap can be connected to each other. In a variation, a loop or D-ring can be attached at one end of the strap 2140 so that the strap can be looped through the loop or D-ring and attached to itself via suitable fasteners. Strap connecting portions 2138, such as reduced thickness portions and/or holes for rivet connections are also provided in the posterior shell wings 2122 to selectively anchor and retain strap assemblies. If holes and rivet connections are used, then the connection points for the straps are pivotable and can allow some rotation or adjustability of the straps. In this variation, two sets of strap connecting portions 2138 are positioned in the posterior shell wings 2122 so that two straps can be used to tighten and close the walker. It will be recognized that any desired number of sets of strap connecting portions can be provided to accommodate any desired number of straps. For example, loops or D-rings can be attached, for example via loops of fabric, to the strap connecting portions 2138 at both lateral and medial sides, along with a strap 2140 connected at one end to the strap connecting portion 2138. The other end of the strap 2140 can be looped through one or both of the loops or D-rings and connected to itself via suitable fasteners, such as hook and loop fasteners.

For ease of simplicity, a strap configuration is shown in FIG. 56, without the dorsal shell 2102 present. It can be seen that the ends of the straps 2140 can be attached at the anterior portion of the walker 2100. Since the Straps 2140 are positioned at the front of the walker 2100 this configuration allows easier access to the straps 2140 to allow wearers to adjust the fit of the walker 2100. The ends of the straps can be connected in any suitable manner, such as hook and loop, or snap fasteners.

It will be recognized that, in use, the straps 2140 are disengaged and the dorsal shell 2102, which is positioned under the straps when the walker 2100 is worn, is removed to allow the wearer to place the lower leg, ankle, and foot within an interior space defined among the dorsal shell 2102, the posterior shell 2120, and the plantar shell portion 2144.

Once the anatomical portion of the wearer is positioned within the interior space, the dorsal shell 2102 can be positioned along the dorsal surfaces of the lower leg, ankle, and foot and the straps 2140 can be engaged over the dorsal shell 2102 to retain the dorsal shell in place to provide the desired amount of support and stabilization to the lower leg, ankle, and foot. It will be recognized that other suitable attachment mechanisms, such as quick connect strapping mechanisms discussed herein, can be used to secure the dorsal shell 2102 in place.

As best seen in FIGS. 55 and 57-59, the plantar shell portion 2144 includes reinforcing, connecting, or guide ridges 2146 positioned along the distal surface thereof for guiding placement of and/or providing connection for an outsole 2148. Additionally, reinforcing ribs or structures can be provided along the proximal surface of the plantar shell portion 2144 if needed. The outsole 2148 can be formed in any manner previously discussed, either as a separate element or integrally with the plantar shell portion 2144. The outsole 2148 can include a heel protector 2154 and a toe protector portion 2150 that is configured to cover and protect the toes of a wearer when the walker 2100 is worn. The toe protector 2150 extends around a section of the side shell portions 2310, 2311 of the posterior shell at the toe end 2316. However, if necessary to accommodate larger sized anatomies, or to accommodate swollen toes, the toe protector portion 2150 can be trimmed down or trimmed completely away.

As best seen in FIG. 55, the outsole 2148 can also include cushioning structures 2152 formed therein to provide appropriate biomechanical functions. In particular, the cushioning structures 2152 can be configured to adjust heel strike and rollover properties of the walker 2100. The outsole 2148 can be formed as a full rocker bottom to provide the associated benefits to the wearer's gait.

Returning to the posterior shell 2120, as best shown in FIGS. 57-59, additional expansion mechanisms are formed in the posterior shell 2120 to reduce or eliminate pressure points and to accommodate users having different sizes of lower legs, ankles, and feet. As previously discussed, a flexible or resilient edge 2124 can be formed along the edges of the posterior shell 2120 of the wing portions 2122 to accommodate different sized anatomical portions of different wearers.

Additionally, expansion joints 2126 can be provided between a posterior portion of the posterior shell 2120 and the posterior shell wings 2122. The expansion joints 2126 can be similarly formed and function in a manner as discussed above. The expansion joints 2126 allow the posterior shell 2120 to automatically stretch or compress to accommodate different sized wearers.

In particular, the expansion joints 2126 can be formed having a larger dimension at the proximal end and tapering down to a smaller dimension at the distal end. In a variation from previously discussed expansion joints, the expansion joints 2126 can include a bridge 2130 spanning across the expansion joint 2126, although such a bridge is not necessary. The function of the bridge 2130 will be discussed in more detail below.

The expansion joints 2126 can be overmolded as previously discussed and can includes a number (any desired) of expansion holes 2128 passing therethrough that can be arranged in any suitable manner. The expansion holes 2128 can have any desired shape or size and can also act as vents. Additionally, the overmolded sections between the expansion holes 2128 can be thinner than the overmolded portions that contact the edges of the posterior shell and wing portions 2120, 2122. The reduced thickness sections can thus allow easier stretching of the expansion joints 2126.

Due to the resiliency or flexibility thereof, the expansion joints 2126 allow the posterior shell wing portions 2122 to expand away from each other or contract towards each other in order to accommodate swelling or different sized anatomies, such as larger or smaller calves, and can reduce or eliminate pressure points. Thus, the walker 2100 can accommodate swelling of the limb or users having different sized calves, without losing rigidity in the sagittal plane (the plane dividing the walker 2100 into medial and lateral sides). Due to the larger proximal end, the expansion joint allows more expansion between the proximal portions of the wing portions 2122 than at distally spaced positions of the wing portions 2122.

If greater expansion is necessary, for example, in order to accommodate even larger calf sizes, the overmolded portion of the expansion joints 2126 can be cut or torn to allow the wing portions 2122 to be able to move further from the posterior portion of the posterior shell 2120. Due to the flexibility or compliance of the overmolded portion of the expansion joints 2126, this portion is relatively easy to cut or tear, and does not leave sharp edges that can cause injury.

In the case that the overmolded portion of the expansion joints 2126 is to be cut or torn, the expansion holes 2128 can act as stopping points for the cut or tear, so that the cut or tear does not extend further than is desired. In this manner, incremental adjustments can be achieved. The cutting or tearing of the overmolded portion of the expansion joints 2126 can extend all the way to the bridge 2130 positioned in the expansion joint 2126, and the bridge 2130 can then act as a stopping point.

As best seen in FIGS. 55 and 59, overmolding 2132 can be provided on the bridge 2130 in the interior space of the walker 2100. If even more expansion is needed, the bridge 2130 can be cut or broken, and the overmolding 2132 serves the function of preventing sharp edges from the cut or broken bridge 2130. The bridge 2130 can include a weakened or frangible portion to aid with cutting or breaking the bridge, in a manner that will be recognized by a skilled artisan.

If even more expansion is needed, the expansion holes 2128 positioned below the bridge 2130 can also be cut, similarly as discussed above. In this manner, there is a large amount of adjustability provided in the walker 2100, such that many wearers having different sizes and shapes of anatomical portions can utilize a generally one size fits all walker.

Figure 63:
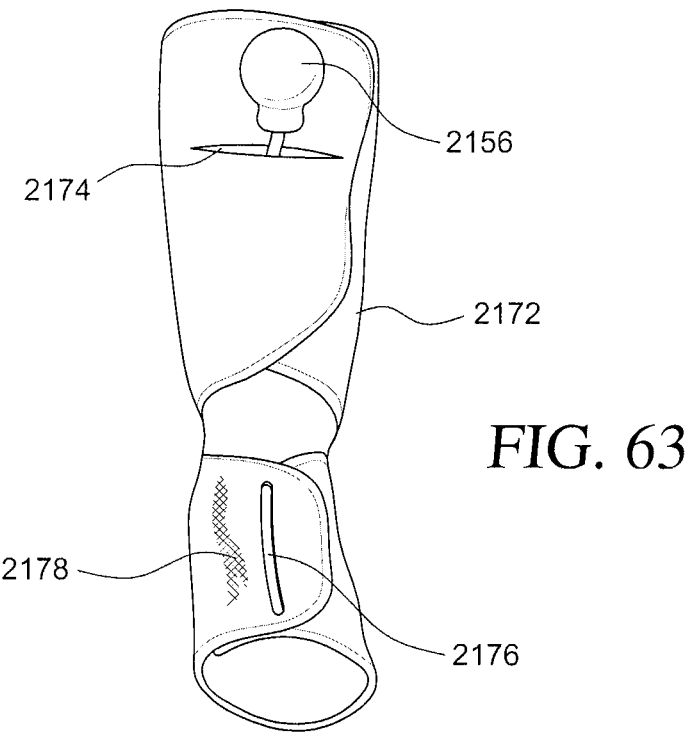
FIG. 63 is a front view of a liner for use with the circumferential walker shown in FIG. 54.

To further provide a generally one size fits all walker, as shown in FIG. 63, a liner 2172 having inflatable bladders and foam padding can be provided as an interface between the wearer's anatomy and the walker 2100. It will be recognized that additional cushioning, such as provided by insoles or separate heel cushions positioned behind the Achilles tendon, can also be provided. The liner 2172 can have any suitable configuration, such as any of those previously discussed, including linked medial and lateral bladders. The liner 2712 can include a covering material, such as softgood, that can be used to engage hook fasteners positioned on opposed flaps thereof, such that the liner 2172 can be positioned and secured to the lower leg, ankle, and foot of the wearer. Additional perspiration wicking material 2178 can be positioned on or in the liner 2172. The liner 2172 can also include a strategically placed spacer element 2176 that can aid with heat and moisture dissipation. For example, the spacer element 2176 can be positioned along the dorsal aspect of the liner 2172 above the foot of the wearer.

As discussed above, the liner 2172 can include inflatable bladders, which can be inflated or deflated to accommodate different sized anatomies or to accommodate swelling, and to provide a desired amount of support and stabilization to the lower leg, ankle, and foot. The bladders can be inflated via an inflation tube, which is connected to a pump assembly 2156.

As shown in FIG. 63, the pump assembly 2156 is connected to the inflation tube, and is carried by the liner 2172. The liner 2172 includes a sliding slot 2174 through which the inflation tube can slightly extend. In this manner, the pump assembly 2156 can be slid in the lateral-medial direction. When the liner 2172 is placed within the interior space of the posterior shell 2120, and secured about the wearer's anatomy, the pump assembly 2156 can thus be slid in the lateral-medial direction in order to aid with aligning the pump assembly 2156 with the pump assembly receiving opening 2106 in the dorsal shell 2102. Thus, donning of the walker 2100 is made easier.

Figure 61:
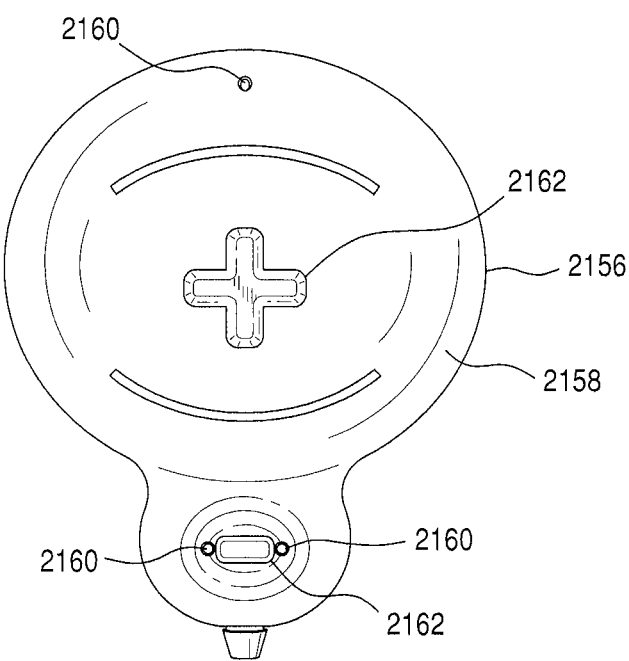
FIG. 61 is a front view of a pump assembly for use with the circumferential walker shown in FIG. 54.
Figure 62:
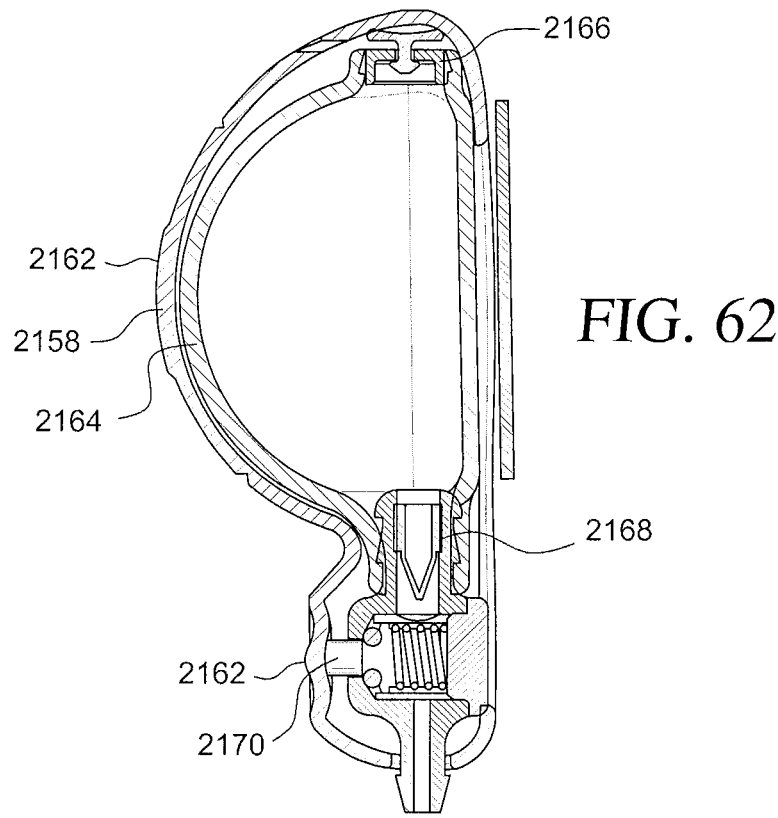
FIG. 62 is a cross-sectional view of the pump assembly shown in FIG. 61.

As shown in FIGS. 61 and 62, the pump assembly 2156 includes an assembly cover 2158, which is made from any suitable flexible, resilient, or compliant material, and which covers the pump 2164 and release valve 2170 assemblies. The assembly cover 2158 includes vent openings 2160 to allow air vented from deflating the bladders to pass through the assembly cover 2158 to atmosphere. The assembly cover 2158 can also include actuation enhancement features 2162, such as raised portions or ridges, which may be configured in any suitable design, such as a cross or an elongated portion. The actuation enhancement features 2162 provide features to enhance friction or gripping for allowing the user to more easily actuate the pump 2164 and the release valve 2170.

As best shown in FIG. 62, the pump assembly 2156 is similarly configured to the pump assembly previously discussed, and includes an inlet valve 2166, which may be a one-way valve that can also function as a release valve, positioned at one end of the pump 2164, which may be a diaphragm pump, and a one-way outlet valve 2168 positioned at a second end of the pump 2164. The one-way outlet valve 2168 communicates through the release valve 2170, which can be of any suitable type, including the release valve previously discussed, with the bladder inflation tube for inflating the bladders. The remaining features of the pump assembly 2156 function in a similar manner as discussed above.

Once the liner 2172 is positioned about and secured to the lower leg, and is positioned within the walker 2100, the pump 2164 can be actuated to inflate the bladders therein to provide an appropriate amount of compression, support, and stability to the lower leg, ankle, and foot.

In view of the above discussed embodiments, it can be seen that a highly adjustable circumferential walker is disclosed, which can accommodate a large variation of sizes of anatomies or swelling of the anatomical portions.

J. Conclusion

The disclosed embodiments of a circumferential walker provide many improvements and allow easy insertion or removal of the lower leg into the walker. Additionally, the quick connect strap tightening mechanisms allow quick and easy tightening of the walker around the lower leg in order to provide the necessary support and stabilization of the lower leg, ankle, and foot. Accordingly, the disclosed embodiments of a circumferential walker are easier to don and doff, which will be advantageous to numerous users, including the elderly or infirm.

It is understood that the size of the disclosed embodiments and the components thereof can be adjusted so that different users having different sized legs, ankles, and feet may benefit from the present design. Specifically, the width, thickness and length of the shells and sole members may be varied to accommodate different sized users.

It is also understood that the locations and numbers of the various straps and connection points can be alternated from those shown, such that the number of straps and connection points, and their respective positions may be altered from the numbers and positions as illustrated herein.

Of course, it is to be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The skilled artisan will recognize the interchangeability of various disclosed features from the disclosed embodiments and variations. For example different connecting mechanisms may be freely changed and substituted. Additionally, any suitable tightening mechanism may be utilized, such as lacing or hook and loop strap fasteners. In addition to the variations described herein, other known equivalents for each feature can be mixed and matched by one of ordinary skill in this art to construct a circumferential walker in accordance with principles of the present invention.

Although this invention has been disclosed in the context of exemplary embodiments and examples, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above.

The invention claimed is:

1. An orthopedic walker, comprising:
    a semi-rigid or rigid posterior shell arranged to extend from a posterior side of a lower leg and ankle, along a distal surface of a foot, and terminating in a plantar shell portion arranged to extend along the plantar surface of the foot, the posterior shell including first and second wing portions arranged to extend partially around the lower leg and ankle to at least partially enclose, protect, and support the lower leg;
    a plurality of clearance holes formed along and oriented toward an anterior edge portion of the first and second wing portions, at least some of the clearance holes having a slotted configuration providing some resiliency to the first and second wing portions to accommodate swelling of a limb or limbs of different sizes;
    a dorsal shell selectively engageable with the posterior shell, the dorsal shell having a semi-rigid or substantially rigid proximal shell portion and a semi-rigid or substantially rigid distal shell portion connected to the proximal shell portion via a connecting portion to permit movement of the proximal and distal shell portions relative to one another; and
    a raised reinforcing portion protruding from and running longitudinally along a length of the proximal shell portion defined between proximal and distal ends of the proximal shell portion, the raised reinforcing portion formed in a single piece with the proximal shell portion, and arranged to strengthen the proximal shell portion and provide support and stabilization to a lower leg of a user when the raised reinforcing portion is engaged with at least one tightening member extending over the proximal shell portion.

2. The orthopedic walker of claim 1, wherein the posterior shell defines at least one eyelet formed through a thickness of the posterior shell, the at least one eyelet having a width or diameter greater than at least one of the clearance holes.

3. The orthopedic walker of claim 2, wherein the at least one eyelet is formed at a lower portion corresponding to an ankle portion of the posterior shell.

4. The orthopedic walker of claim 2, wherein the at least one eyelet comprises first and second eyelets formed on opposed sides of a lower portion of the posterior shell.

5. The orthopedic walker of claim 2, wherein an elongate seat opening depends from a side of the eyelet.

6. The orthopedic walker of claim 1, wherein the posterior shell defining a pair of elongate slots extending longitudinally along a length of the posterior shell, the pair of slots are formed along a first side of the posterior shell, a section of the semi-rigid or rigid material segment forming the posterior shell defined between the pair of slots.

7. The orthopedic walker of claim 6, further comprising a strap extending through the pair of slots and retained from longitudinal movement relative to the length of the posterior shell by the semi-rigid or rigid material segment.

8. The orthopedic walker of claim 1, wherein the dorsal shell defines a pump receiving opening arranged to receive a pump.

9. An orthopedic walker, comprising:
a semi-rigid or rigid posterior shell arranged to extend from a posterior side of a lower leg and ankle, along a distal surface of a foot, and terminating in a plantar shell portion arranged to extend along the plantar surface of the foot, the posterior shell including first and second wing portions arranged to extend partially around the lower leg and ankle to at least partially enclose, protect, and support the lower leg;

a plurality of clearance holes formed along and oriented toward an anterior edge portion of the first and second wing portions, at least some of the clearance holes having a slotted configuration providing some resiliency to the first and second wing portions to accommodate swelling of a limb or limbs of different sizes;

a plurality of tightening members secured to the posterior shell; and a dorsal shell selectively engageable with the posterior shell, the dorsal shell having a semi-rigid or substantially rigid proximal shell portion and a semi-rigid or substantially rigid distal shell portion connected to the proximal shell portion via a connecting portion to permit movement of the proximal and distal shell portions relative to one another, the dorsal shell defining a pump receiving opening arranged to receive a pump and a raised reinforcing portion protruding from and running longitudinally along a length the proximal shell portion defined between proximal and distal ends of the proximal shell portion, the raised reinforcing portion formed in a single piece with the proximal shell portion, and arranged to strengthen the proximal shell portion and provide support and stabilization to a lower leg of a user when the raised reinforcing portion is engaged with at least one of the tightening members extending from the posterior shell and over the proximal shell portion.

* * * * *